(12) United States Patent
Karjala et al.

(10) Patent No.: US 7,524,911 B2
(45) Date of Patent: Apr. 28, 2009

(54) ADHESIVE AND MARKING COMPOSITIONS MADE FROM INTERPOLYMERS OF ETHYLENE/α-OLEFINS

(75) Inventors: Teresa P. Karjala, Lake Jackson, TX (US); Selim Yalvac, Pearland, TX (US); Charles F. Diehl, Lake Jackson, TX (US); Yunwa W. Cheung, Lake Jackson, TX (US); Cynthia L. Rickey, Lake Jackson, TX (US)

(73) Assignee: Dow Global Technologies Inc., Midland, MI (US)

( * ) Notice: Subject to any disclaimer, the term of this patent is extended or adjusted under 35 U.S.C. 154(b) by 492 days.

(21) Appl. No.: 11/376,957

(22) Filed: Mar. 15, 2006

(65) Prior Publication Data
US 2006/0199897 A1    Sep. 7, 2006

Related U.S. Application Data

(63) Continuation-in-part of application No. PCT/US2005/008917, filed on Mar. 17, 2005.

(60) Provisional application No. 60/718,000, filed on Sep. 16, 2005, provisional application No. 60/553,906, filed on Mar. 17, 2004.

(51) Int. Cl.
*C08F 4/44* (2006.01)
*A61K 9/16* (2006.01)

(52) U.S. Cl. ............ 526/348; 526/348.2; 526/348.6; 526/161; 526/171; 525/242; 525/240; 524/543

(58) Field of Classification Search ............. 526/348, 526/348.2, 348.6, 161, 171; 525/242, 240; 524/543
See application file for complete search history.

(56) References Cited

U.S. PATENT DOCUMENTS

| | | | |
|---|---|---|---|
| 3,873,642 A | 3/1975 | Jezl | |
| 5,468,810 A | 11/1995 | Hayakawa et al. | |
| 5,594,080 A | 1/1997 | Waymouth et al. | |
| 5,610,253 A | 3/1997 | Hatke et al. | |
| 5,733,980 A | 3/1998 | Cozewith et al. | |
| 5,798,420 A | 8/1998 | Cozewith et al. | |
| 5,969,070 A | 10/1999 | Waymouth et al. | |
| 6,114,457 A | 9/2000 | Markel et al. | |
| 6,147,180 A | 11/2000 | Markel et al. | |
| 6,262,203 B1 | 7/2001 | Chien et al. | |
| 6,566,544 B1 | 5/2003 | Waymouth et al. | |
| 2004/0024814 A1* | 2/2004 | Takeo et al. | 709/203 |
| 2004/0048019 A1* | 3/2004 | Ohlsson | 428/35.7 |
| 2004/0081795 A1 | 4/2004 | Wang et al. | |
| 2004/0121922 A1 | 6/2004 | Okada et al. | |
| 2004/0236002 A1 | 11/2004 | Hassan et al. | |

FOREIGN PATENT DOCUMENTS

| | | |
|---|---|---|
| EP | 0 274 906 A2 | 7/1988 |
| EP | 0 958 313 B1 | 9/2002 |
| EP | 1 262 498 A2 | 12/2002 |
| JP | 2002-206007 A | 7/2002 |
| JP | 2004-204058 A | 7/2004 |
| WO | WO 98/49211 A1 | 11/1988 |
| WO | WO 95/27745 A1 | 10/1995 |
| WO | WO 95/27746 A1 | 10/1995 |
| WO | WO 98/34970 A1 | 8/1998 |
| WO | WO 99/35171 A1 | 7/1999 |
| WO | WO 00/37514 A1 | 6/2000 |
| WO | WO 02/066540 A2 | 8/2002 |
| WO | WO 03/014046 A1 | 2/2003 |
| WO | WO 2004/046214 A2 | 6/2004 |
| WO | WO 2005/090425 A1 | 9/2005 |
| WO | WO 2005/090426 A1 | 9/2005 |
| WO | WO 2005/090427 A1 | 9/2005 |

* cited by examiner

*Primary Examiner*—Robert D. Harlan

(57) ABSTRACT

An adhesive composition comprises: (i) at least one ethylene/α-olefin interpolymer, (ii) at least one tackifier; and (iii) optionally at least one additive, such as a plasticizer, wax and antioxidant. Preferably, the ethylene/α-olefin interpolymer has a $M_w/M_n$ from about 1.7 to about 3.5, at least one melting point, $T_m$, in degrees Celsius, and a density, d, in grams/cubic centimeter, wherein the numerical values of $T_m$ and d correspond to the relationship: $T_m \geq 858.91 - 1825.3(d) + 1112.8(d)^2$. The composition has relatively higher SAFT temperature and can be used in hot melt adhesives pressure-sensitive adhesives, and thermoplastic marking paints.

47 Claims, 12 Drawing Sheets

ADHESIVE AND MARKING COMPOSITIONS MADE FROM INTERPOLYMERS OF ETHYLENE/α-OLEFINS

CROSS-REFERENCE TO RELATED APPLICATIONS

This application claims priority to U.S. Provisional Application No. 60/718,000, filed Sep. 16, 2005, which further claims priority to PCT Application No. PCT/US2005/008917, filed on Mar. 17, 2005, which claims priority to U.S. Provisional Application No. 60/553,906, filed Mar. 17, 2004. For purposes of United States patent practice, the contents of the provisional applications and the PCT application are herein incorporated by reference in their entirety.

FIELD OF THE INVENTION

This invention relates to compositions comprise at least one ethylene/α-olefin interpolymers, methods of making the compositions, and methods of using the compositions in applications, such as hot melt adhesives, pressure sensitive adhesives, and thermoplastic marking compositions.

BACKGROUND OF THE INVENTION

An adhesive is a substance capable of holding solid materials (e.g., adherents or substrates) together by surface attachment. Adhesives have been widely used since ancient times. Archaeologists have found evidence of substances being used as adhesives in Babylon dating back to 4000 B.C. and in Egypt between 1500-1000 B.C. The first adhesive patent was issued in about 1750 in Britain for a glue made from fish. Later, patents were issued for adhesives using natural rubber, animal bones, fish, starch, milk protein or casein. The development of synthetic adhesives from the late 19th century has led to many synthetic adhesives, such as nitrocellulose, phenol-formaldehyde resins, urea-formaldehyde resins, epoxy resins, bismaleimide resins, polysiloxanes, polychloroprene, polyacrylates, polymethacrylates, polyurethanes, polycyanoacrylates, hot melt adhesives and pressure sensitive adhesives.

Pressure sensitive adhesives (PSAs) generally are adhesive materials which bond to adherents when a required pressure is applied to effect an adhesion to the adherents. PSAs can be permanent or removable. Removable PSAs have been widely used in re-positionable applications, such as post-it notes. Pressure sensitive adhesives are generally based on a polymer, a tackifier and an oil. Some common PSAs are based on polymers such as natural rubbers, synthetic rubbers (e.g., styrene-butadiene rubber (SBR) and SIS), polyacrylates, polymethacrylates, and poly-alpha-olefins. The PSAs can be solvent-based, water-based, or hot melt systems.

Hot-melt adhesives at ambient temperature are generally solid materials that can be heated to a melt to hold adherents or substrates together upon cooling and solidifying. In some applications, the bonded substrates can be detached by remelting the hot melt adhesive if the substrates can withstand the heat. The hot melt adhesives can be used in paper products, packaging materials, laminated wood panels, kitchen countertops, vehicles, tapes, labels, and a variety of disposable goods such as disposable diapers, hospital pads, feminine sanitary napkins, and surgical drapes. These hot melt adhesives are generally based on a polymer, tackifier, and a wax. Some common hot melt adhesives are based on polymer components including ethylene based semi-crystalline polymers such as ethylene-vinyl acetate copolymer (EVA) and linear low density polyethylene (LLDPE), styrene block copolymers (SBC) such as styrene-isoprene-styrene (SIS) copolymer and styrene-butadiene-styrene (SBS) copolymer, ethylene ethyl acrylate copolymers (EEA), and polyurethane reactive adhesives (PUR). One desirable property of hot melt adhesives is the absence of a liquid carrier, thereby eliminating the costly process associated with solvent removal.

Some compositions that contain a polymer, a tackifier and optionally at least a filler or a pigment may be used as thermoplastic marking compositions. The polymer can be a silane-modified petroleum resin, an ethylene-vinyl acetate copolymer, an atactic polypropylene; a carboxy-modified hydrocarbon resin, an ester-modified hydrocarbon resin, a polyolefin copolymer, or a combination thereof.

Despite the availability of a variety of hot melt adhesives, pressure sensitive adhesives, and road paints, there are still needs for new adhesive compositions with improved properties.

SUMMARY OF INVENTION

The aforementioned needs can be met by various aspects of the invention. In one aspect, the invention relates to adhesive compositions comprising at least one ethylene/α-olefin interpolymer and a tackifier. In certain embodiments, the ethylene/α-olefin interpolymer has a $M_w/M_n$ from about 1.7 to about 3.5, at least one melting point, $T_m$, in degrees Celsius, and a density, d, in grams/cubic centimeter, wherein the numerical values of $T_m$ and d correspond to the relationship:

$$T_m > -2002.9 + 4538.5(d) - 2422.2(d)^2.$$

In certain embodiments, ethylene/α-olefin interpolymer in the adhesive compositions provided herein has a $M_w/M_n$ from about 1.7 to about 3.5, and is characterized by a heat of fusion, $\Delta H$ in J/g, and a delta quantity, $\Delta T$, in degrees Celsius defined as the temperature difference between the tallest DSC peak and the tallest CRYSTAF peak, wherein the numerical values of $\Delta T$ and $\Delta H$ have the following relationships:

$\Delta T > -0.1299(\Delta H) + 62.81$ for $\Delta H$ greater than zero and up to 130 J/g, $\Delta T \geq 48°$ C. for $\Delta H$ greater than 130 J/g, wherein the CRYSTAF peak is determined using at least 5 percent of the cumulative polymer, and if less than 5 percent of the polymer has an identifiable CRYSTAF peak, then the CRYSTAF temperature is 30° C.

In certain embodiments, ethylene/α-olefin interpolymer in the adhesive compositions provided herein is characterized by an elastic recovery, Re, in percent at 300 percent strain and 1 cycle measured with a compression-molded film of the ethylene/α-olefin interpolymer, and a density, d, in grams/cubic centimeter, wherein the numerical values of Re and d satisfy the following relationship when ethylene/α-olefin interpolymer is substantially free of a cross-linked phase:

Re>1481−1629(d), Re>1491−1629(d), Re>1501−1629(d) or Re>1511−1629(d).

In certain embodiments, ethylene/α-olefin interpolymer in the adhesive compositions provided herein has a molecular fraction which elutes between 40° C. and 130° C. when fractionated using TREF, characterized in that the fraction has a molar comonomer content of at least 5 percent higher than that of a comparable random ethylene interpolymer fraction eluting between the same temperatures, wherein said comparable random ethylene interpolymer has the same comonomer(s) and has a melt index, density, and molar comonomer content (based on the whole polymer) within 10 percent of that of the ethylene/α-olefin interpolymer.

In certain embodiments, ethylene/α-olefin interpolymer in the adhesive compositions provided herein has a storage modulus at 25° C., G'(25° C.), and a storage modulus at 100° C., G'(100° C.), wherein the ratio of G'(25° C.) to G'(100° C.) is in the range of about 1:1 to about 9:1.

In certain embodiments, ethylene/α-olefin interpolymer in the adhesive compositions provided herein has a molecular fraction which elutes between 40° C. and 130° C. when fractionated using TREF, characterized in that the fraction has a block index of at least 0.5 and up to about 1.

In certain embodiments, ethylene/α-olefin interpolymer in the adhesive compositions provided herein has an average block index greater than zero and up to about 1.0 and a molecular weight distribution, Mw/Mn, greater than about 1.3.

In certain embodiments, the adhesive composition provided herein is a hot melt adhesive, a pressure sensitive adhesive or a thermoplastic marking composition.

In certain embodiments, the α-olefin in the ethylene/α-olefin interpolymer is styrene, propylene, 1-butene, 1-hexene, 1-octene, 4-methyl-1-pentene, norbornene, 1-decene; 1,5-hexadiene or a combination thereof.

In certain embodiments, the ethylene/α-olefin interpolymer in the compositions provided herein has a number average molecular weight, $M_n$, of from about 500 to about 500,000.

In certain embodiments, the ethylene/α-olefin interpolymer has a melt index in the range of about 1 to about 5000 g/10 minutes, about 2 to about 2000 g/10 minutes or about 5 to about 1500 g/10 minutes measured according to ASTM D-1238, Condition 190° C./2.16 kg. In other embodiments, the ethylene/α-olefin interpolymer has a melt index in the range of about 0.1 to about 2000 g/10 minutes measured according to ASTM D-1238, Condition 190° C./2.16 kg. In certain embodiments, the ethylene/α-olefin interpolymer has a melt index in the range of about 1 to about 1500 g/10 minutes, about 2 to about 1000 g/10 minutes or about 5 to about 500 g/10 minutes measured according to ASTM D-1238, Condition 190° C./2.16 kg. In certain embodiments, the ethylene/α-olefin interpolymer has a melt index in the range of about 5 to about 50 g/10 minutes or about 10 to about 30 g/10 minutes measured according to ASTM D-1238, Condition 190° C./2.16 kg.

In one embodiment, the overall density of the ethylene/α-olefin interpolymer is from about 0.85 to 0.88 g/cc or from about 0.86 to 0.875 g/cc.

In certain embodiments, the range of the ethylene/α-olefin interpolymer in the compositions provided herein is from about 10% to about 50% by weight of the total composition. In certain embodiments, the ethylene/α-olefin interpolymer is in the range from about 15% to about 30% by weight of the total composition.

In certain embodiments, the amount of tackifier in the adhesive compositions is in the range from about 5% to about 70% by weight of the total composition. In certain embodiments, the tackifier is present in the range from about 20% to about 70% by weight of the total composition.

In certain embodiments, the tackifier is at least one of a natural and modified resin; a glycerol or pentaerythritol ester of natural or modified rosin; a copolymer or terpolymer of natured terpene; a polyterpene resin or a hydrogenated polyterpene resin; a phenolic modified terpene resin or a hydrogenated derivative thereof; an aliphatic or cycloaliphatic hydrocarbon resin or a hydrogenated derivative thereof; an aromatic hydrocarbon resin or a hydrogenated derivative thereof; an aromatic modified aliphatic or cycloaliphatic hydrocarbon resin or a hydrogenated derivative thereof; or a combination thereof. When the tackifier is an aliphatic hydrocarbon resin, it can have at least five carbon atoms. In certain embodiments, the tackifier has a R&B softening point equal to or greater than 80° C.

In certain embodiments, the adhesive compositions provided herein comprise an additive selected from the group consisting of plasticizers, oils, waxes, antioxidants, UV stabilizers, colorants or pigments, fillers, flow aids, coupling agents, crosslinking agents, surfactants, solvents, and combinations thereof. In certain embodiments, the additive is plasticizer, such as a mineral oil, liquid polybutene or a combination thereof.

In certain embodiments, the compositions, further comprise a wax, such as a petroleum wax, a low molecular weight polyethylene or polypropylene, a synthetic wax, a polyolefin wax, a beeswax, a vegetable wax, a soy wax, a palm wax, a candle wax or an ethylene/α-olefin interpolymer having a melting point of greater than 25° C. In certain embodiments, the wax is a low molecular weight polyethylene or polypropylene having a number average molecular weight of about 400 to about 6,000 g/mole. The wax can be present in the range from about 10% to about 50% or 20% to about 40% by weight of the total composition.

In certain embodiments, the composition further comprises an antioxidant. The antioxidant can be present in the range from greater than 0% to about 1% or about 0.05% to about 0.75% by weight of the total composition.

In certain embodiments, the composition further comprises a filler. The filler can be in the amount up to 80% by weight of the total composition. The filler can be selected from sand, talc, dolomite, calcium carbonate, clay, silica, mica, wollastonite, feldspar, aluminum silicate, alumina, hydrated alumina, glass bead, glass microsphere, ceramic microsphere, thermoplastic microsphere, barite, wood flour, or a combination thereof.

In certain embodiments, the compositions provided herein have a shear adhesion failure temperature of at least 32° C., 43° C., 54° C. or 66° C.

In certain embodiments, the composition has a 180° peel adhesion to a polyester substrate of at least about 100 N/dm. In certain embodiments, the composition has a 180° peel adhesion to a stainless substrate greater than 0.1 lbs, greater than 1.5 lbs or greater than 3 lbs. In certain embodiments, the composition has a 180° peel adhesion to a polypropylene substrate greater than 0.1 lbs, greater than 1.5 lbs or greater than 3 lbs.

In certain embodiments, the composition has a Brookfield viscosity from about 500 and 50,000 cp at 177° C. In certain embodiments, the composition has the G'(25° C.) from about $1 \times 10^3$ to about $1 \times 10^6$ Pa, from about $2 \times 10^3$ to about $5 \times 10^5$ Pa, or from about $1 \times 10^4$ to about $5 \times 10^5$ Pa.

In certain embodiments, the ratio of G'(25° C.) to G'(75° C.) in the compositions provided herein is from about 1:1 to about 110:1, from about 1:1 to about 75:1, from about 1:1 to about 25:1, from about 1:1 to about 20:1, from about 1:1 to about 15:1, from about 1:1 to about 10:1, from about 1:1 to about 9:1, from about 1:1 to about 8:1, from about 1:1 to about 7:1, from about 1:1 to about 6:1, from about 1:1 to about 5:1, or from about 1:1 to about 4:1.

In certain embodiments, the loop tack of the adhesive compositions provided herein is greater than about 0.5 lb, greater than about 1 lb, or greater than about 2 lb.

In certain embodiments, the compositions have a SAFT of the hot melt adhesive composition that is greater than about 130° F., greater than about 140° F., or greater than about 150°

F. Certain of the composition herein have a SAFT greater than about 180° F., greater than about 190° F., or greater than about 200° F. In certain embodiments, the SAFT of the pressure sensitive adhesive composition is greater than 54° C. In certain embodiments, the SAFT of the pressure sensitive adhesive compositions provided herein is greater than or equal to 90° F., greater than or equal to 110° F., greater than or equal to 130° F. or greater than or equal to 150° F. In certain embodiments, the fiber tear of the pressure sensitive adhesive composition is 100% at a temperature from about 25 to about 60° C.

In certain embodiments, the thermoplastic marking compositions provided herein further comprise a filler and a pigment. The filler can comprise glass microspheres or glass beads. In certain embodiments, the thermoplastic marking composition is in the form of a hot melt extrusion road marking, hot melt spray road marking, hot melt hand applied road marking, colored hot melt marked bicycle lane, simulation or training road marking, preformed extruded traffic symbol or tape, flexible and soft sports/playground surface marking, safety marking on a ship, or a reflective traffic safety coating.

In certain embodiments, an article comprising a substrate coated with the composition described herein is provided. The article is selected from a tape, a label, a decal, a case, a carton, a tray, a medical device, a bandage and a hygiene article.

In another aspect, the invention relates to methods of making a composition, comprising: blending the ethylene/α-olefin interpolymer with a tackifier. The ethylene/α-olefin interpolymer is described above and elsewhere herein. In certain embodiments, the method further comprises blending an additive selected from the group consisting of plasticizers, oils, waxes, antioxidants, UV stabilizers, colorants or pigments, fillers, flow aids, coupling agents, crosslinking agents, surfactants, solvents, and combinations thereof. In certain embodiments, the additive is a plasticizer or an oil. In certain embodiments, the additive is a wax. In certain embodiments, the additive is an antioxidant. In certain embodiments, the additive is a pigment. In certain embodiments, the additive is a filler. In certain embodiments, the filler comprises glass beads or glass microspheres.

Additional aspects of the invention and characteristics and properties of various embodiments of the invention become apparent with the following description.

DETAILED DESCRIPTION OF THE INVENTION

General Definitions

Figure 1:
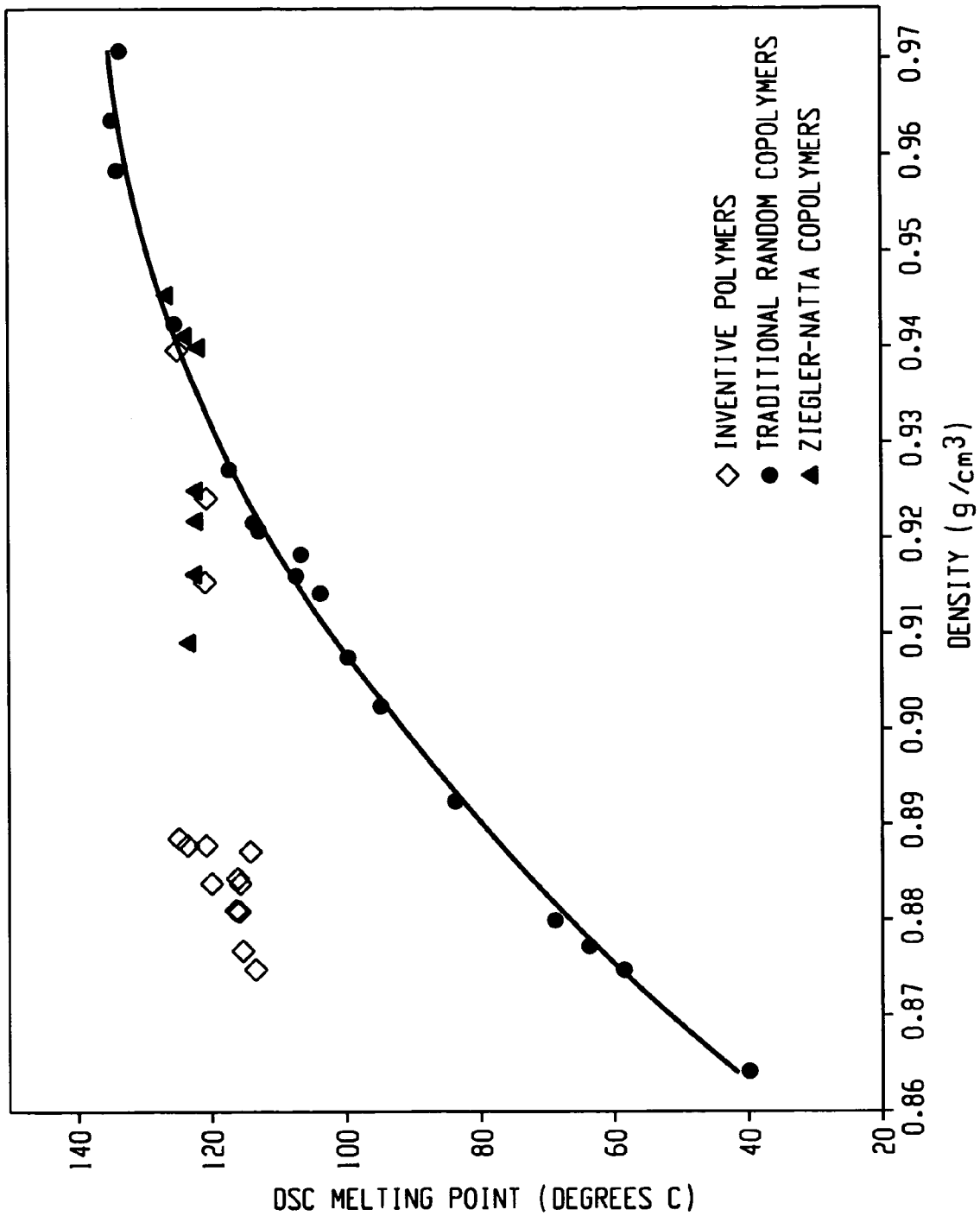
FIG. 1 shows the melting point/density relationship for the inventive polymers (represented by diamonds) as compared to traditional random copolymers (represented by circles) and Ziegler-Natta copolymers (represented by triangles).

"Polymer" means a polymeric compound prepared by polymerizing monomers, whether of the same or a different type. The generic term "polymer" embraces the terms "homopolymer," "copolymer," "terpolymer" as well as "interpolymer."

"Interpolymer" means a polymer prepared by the polymerization of at least two different types of monomers. The generic term "interpolymer" includes the term "copolymer" (which is usually employed to refer to a polymer prepared from two different monomers) as well as the term "terpolymer" (which is usually employed to refer to a polymer prepared from three different types of monomers). It also encompasses polymers made by polymerizing four or more types of monomers.

The term "ethylene/α-olefin interpolymer" generally refers to polymers comprising ethylene and an α-olefin having 3 or more carbon atoms. Preferably, ethylene comprises the majority mole fraction of the whole polymer, i.e., ethylene comprises at least about 50 mole percent of the whole polymer. More preferably ethylene comprises at least about 60 mole percent, at least about 70 mole percent, or at least about 80 mole percent, with the substantial remainder of the whole polymer comprising at least one other comonomer that is preferably an α-olefin having 3 or more carbon atoms. For many ethylene/octene copolymers, the preferred composition comprises an ethylene content greater than about 80 mole percent of the whole polymer and an octene content of from about 10 to about 15, preferably from about 15 to about 20 mole percent of the whole polymer. In some embodiments, the ethylene/α-olefin interpolymers do not include those produced in low yields or in a minor amount or as a by-product of a chemical process. While the ethylene/α-olefin interpolymers can be blended with one or more polymers, the as-produced ethylene/α-olefin interpolymers are substantially pure and often comprise a major component of the reaction product of a polymerization process.

The ethylene/α-olefin interpolymers comprise ethylene and one or more copolymerizable α-olefin comonomers in polymerized form, characterized by multiple blocks or segments of two or more polymerized monomer units differing in chemical or physical properties. That is, the ethylene/α-olefin interpolymers are block interpolymers, preferably multi-block interpolymers or copolymers. The terms "interpolymer" and copolymer" are used interchangeably herein. In some embodiments, the multi-block copolymer can be represented by the following formula:

$(AB)_n$ where n is at least 1, preferably an integer greater than 1, such as 2, 3, 4, 5, 10, 15, 20, 30, 40, 50, 60, 70, 80, 90, 100, or higher, "A" represents a hard block or segment and "B" represents a soft block or segment. Preferably, As and Bs are linked in a substantially linear fashion, as opposed to a substantially branched or substantially star-shaped fashion. In other embodiments, A blocks and B blocks are randomly distributed along the polymer chain. In other words, the block copolymers usually do not have a structure as follows.

AAA–AA–BBB–BB

In still other embodiments, the block copolymers do not usually have a third type of block, which comprises different comonomer(s). In yet other embodiments, each of block A and block B has monomers or comonomers substantially randomly distributed within the block. In other words, neither block A nor block B comprises two or more sub-segments (or sub-blocks) of distinct composition, such as a tip segment, which has a substantially different composition than the rest of the block.

The multi-block polymers typically comprise various amounts of "hard" and "soft" segments. "Hard" segments refer to blocks of polymerized units in which ethylene is present in an amount greater than about 95 weight percent, and preferably greater than about 98 weight percent based on the weight of the polymer. In other words, the comonomer content (content of monomers other than ethylene) in the hard segments is less than about 5 weight percent, and preferably less than about 2 weight percent based on the weight of the polymer. In some embodiments, the hard segments comprises all or substantially all ethylene. "Soft" segments, on the other hand, refer to blocks of polymerized units in which the comonomer content (content of monomers other than ethylene) is greater than about 5 weight percent, preferably greater than about 8 weight percent, greater than about 10 weight percent, or greater than about 15 weight percent based on the weight of the polymer. In some embodiments, the comonomer content in the soft segments can be greater than about 20 weight percent, greater than about 25 weight percent, greater than about 30 weight percent, greater than about 35 weight percent, greater than about 40 weight percent, greater than about 45 weight percent, greater than about 50 weight percent, or greater than about 60 weight percent.

The soft segments can often be present in a block interpolymer from about 1 weight percent to about 99 weight percent of the total weight of the block interpolymer, preferably from about 5 weight percent to about 95 weight percent, from about 10 weight percent to about 90 weight percent, from about 15 weight percent to about 85 weight percent, from about 20 weight percent to about 80 weight percent, from about 25 weight percent to about 75 weight percent, from about 30 weight percent to about 70 weight percent, from about 35 weight percent to about 65 weight percent, from about 40 weight percent to about 60 weight percent, or from about 45 weight percent to about 55 weight percent of the total weight of the block interpolymer. Conversely, the hard segments can be present in similar ranges. The soft segment weight percentage and the hard segment weight percentage can be calculated based on data obtained from DSC or NMR. Such methods and calculations are disclosed in a concurrently filed U.S. patent application Ser. No. 11/376, 835, entitled "Ethylene/α-Olefin Block Interpolymers", filed on Mar. 15, 2006, in the name of Colin L. P. Shan, Lonnie Hazlitt, et. al. and assigned to Dow Global Technologies Inc., the disclose of which is incorporated by reference herein in its entirety.

The term "crystalline" if employed, refers to a polymer that possesses a first order transition or crystalline melting point (Tm) as determined by differential scanning calorimetry (DSC) or equivalent technique. The term may be used interchangeably with the term "semicrystalline". The term "amorphous" refers to a polymer lacking a crystalline melting point as determined by differential scanning calorimetry (DSC) or equivalent technique.

The term "multi-block copolymer" or "segmented copolymer" refers to a polymer comprising two or more chemically distinct regions or segments (referred to as "blocks") preferably joined in a linear manner, that is, a polymer comprising chemically differentiated units which are joined end-to-end with respect to polymerized ethylenic functionality, rather than in pendent or grafted fashion. In a preferred embodiment, the blocks differ in the amount or type of comonomer incorporated therein, the density, the amount of crystallinity, the crystallite size attributable to a polymer of such composition, the type or degree of tacticity (isotactic or syndiotactic), regio-regularity or regio-irregularity, the amount of branching, including long chain branching or hyper-branching, the homogeneity, or any other chemical or physical property. The multi-block copolymers are characterized by unique distributions of both polydispersity index (PDI or Mw/Mn), block length distribution, and/or block number distribution due to the unique process of making the copolymers. More specifically, when produced in a continuous process, the polymers desirably possess PDI from 1.7 to 2.9, preferably from 1.8 to 2.5, more preferably from 1.8 to 2.2, and most preferably from 1.8 to 2.1. When produced in a batch or semi-batch process, the polymers possess PDI from 1.0 to 2.9, preferably from 1.3 to 2.5, more preferably from 1.4 to 2.0, and most preferably from 1.4 to 1.8.

In the following description, all numbers disclosed herein are approximate values, regardless whether the word "about" or "approximate" is used in connection therewith. They may vary by 1 percent, 2 percent, 5 percent, or, sometimes, 10 to 20 percent. Whenever a numerical range with a lower limit, $R^L$ and an upper limit, $R^U$, is disclosed, any number falling within the range is specifically disclosed. In particular, the following numbers within the range are specifically disclosed: $R=R^L+k*(R^U-R^L)$, wherein k is a variable ranging from 1 percent to 100 percent with a 1 percent increment, i.e., k is 1 percent, 2 percent, 3 percent, 4 percent, 5 percent, . . . , 50 percent, 51 percent, 52 percent, . . . , 95 percent, 96 percent, 97 percent, 98 percent, 99 percent, or 100 percent. Moreover, any numerical range defined by two R numbers as defined in the above is also specifically disclosed.

Embodiments of the invention provide compositions that comprise an ethylene/α-olefin interpolymer and a tackifier resin. The compositions possess unique properties that are suitable for a variety of applications, particularly where a certain level of adhesion is required. Some non-limiting examples of suitable applications include hot melt adhesives, pressure sensitive adhesives, thermoplastic marking compositions, and the like. Preferably, the ethylene/α-olefin interpolymers are a multi-block copolymer comprising at least one soft block and at least one hard block.

In some embodiments, the composition has a shear adhesion failure temperature (SAFT) of at least 90° F. (32° C.), at least 110° F. (43° C.), at least 130° F. (54° C.), or at least 150° F. (66° C.). The SAFT is a measure of the upper service temperature of the composition and can be determined by the method described in ASTM D4498, which is incorporated herein by reference. In further embodiments, the composition has a 180° peel adhesion of at least about 100 N/dm. The 180° peel adhesion of the composition can be measured by bonding stainless steel to Mylar using the method described in the Pressure Sensitive Tape Council (PSTC)-1, which is incorporated herein by reference.

In other embodiments, the adhesive compositions have a low melt viscosity so that it is easy to process the composition without resorting to the inclusion of solvents or excess plasticizer into the compositions. The melt viscosities of the compositions can be measured by a Brookfield viscometer using appropriate spindles as by ASTM D3236 at about 350° F. (177° C.), which is incorporated herein by reference. In some embodiments, the composition has a melt viscosity of less than 20,000 cps at about 177° C., or less than about 10,000 at 177° C., or less than about 5,000 at 177° C. measured according to ASTM D3236.

Ethylene/α-Olefin Interpolymers

The ethylene/α-olefin interpolymers used in embodiments of the invention (also referred to as "inventive interpolymer" or "inventive polymer") comprise ethylene and one or more copolymerizable α-olefin comonomers in polymerized form, characterized by multiple blocks or segments of two or more polymerized monomer units differing in chemical or physical properties (block interpolymer), preferably a multi-block copolymer. The ethylene/α-olefin interpolymers are characterized by one or more of the aspects described as follows.

In one aspect, the ethylene/α-olefin interpolymers used in embodiments of the invention have a $M_w/M_n$ from about 1.7 to about 3.5 and at least one melting point, $T_m$, in degrees Celsius and density, d, in grams/cubic centimeter, wherein the numerical values of the variables correspond to the relationship:

$$T_m > -2002.9 + 4538.5(d) - 2422.2(d)^2, \text{ and preferably}$$

$$T_m \geq -6288.1 + 13141(d) - 6720.3(d)^2, \text{ and more preferably}$$

$$T_m \geq 858.91 - 1825.3(d) + 1112.8(d)^2.$$

Such melting point/density relationship is illustrated in FIG. 1. Unlike the traditional random copolymers of ethylene/α-olefins whose melting points decrease with decreasing densities, the inventive interpolymers (represented by diamonds) exhibit melting points substantially independent of the density, particularly when density is between about 0.87 g/cc to about 0.95 g/cc. For example, the melting point of such polymers are in the range of about 110° C. to about 130° C. when density ranges from 0.875 g/cc to about 0.945 g/cc. In some embodiments, the melting point of such polymers are in the range of about 115° C. to about 125° C. when density ranges from 0.875 g/cc to about 0.945 g/cc.

Figure 2:
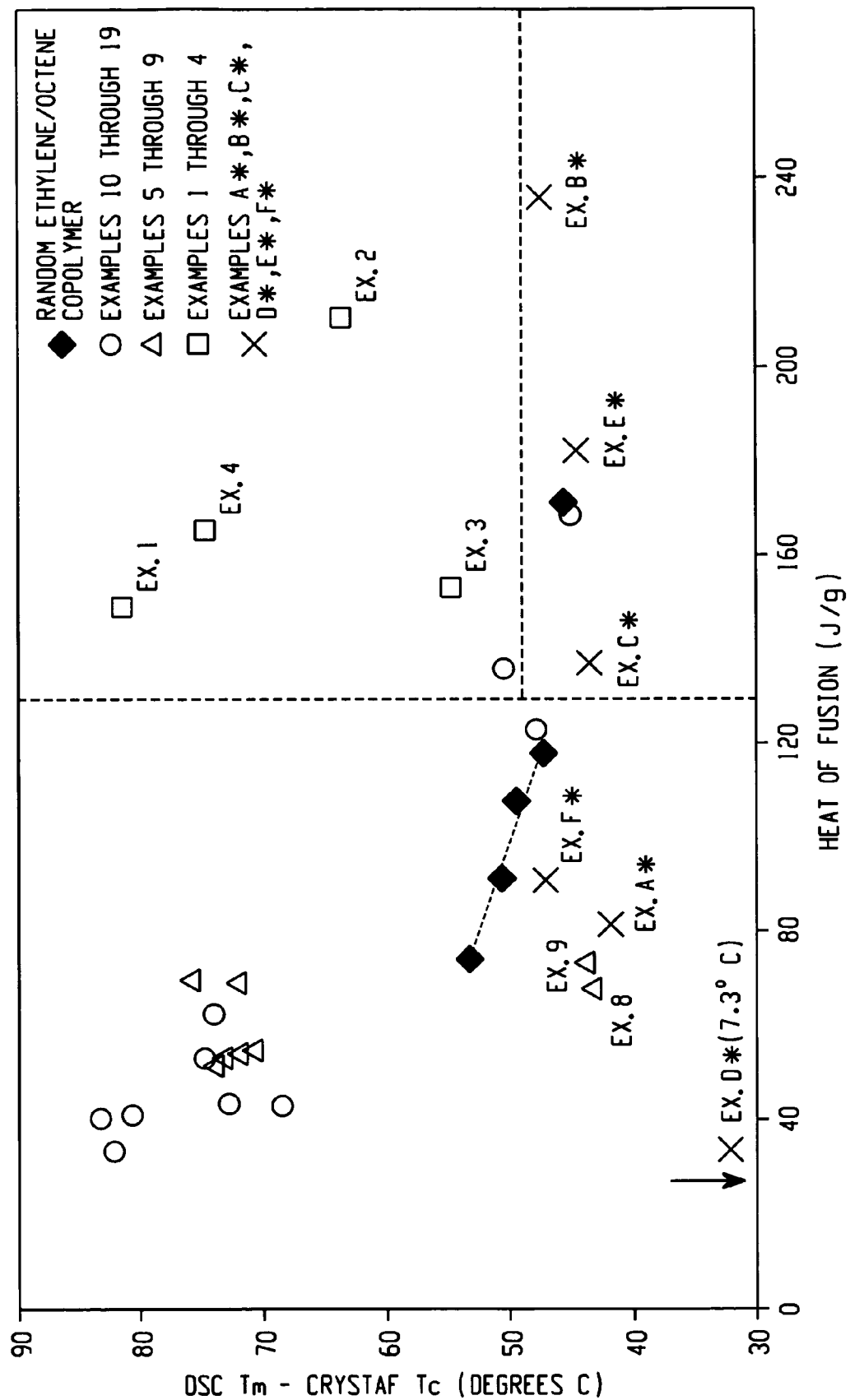
FIG. 2 shows plots of delta DSC-CRYSTAF as a function of DSC Melt Enthalpy for various polymers. The diamonds represent random ethylene/octene copolymers; the squares represent polymer examples 1-4; the triangles represent polymer examples 5-9; and the circles represent polymer examples 10-19. The "X" symbols represent polymer examples A*-F*.

In another aspect, the ethylene/α-olefin interpolymers comprise, in polymerized form, ethylene and one or more α-olefins and are characterized by a ΔT, in degree Celsius, defined as the temperature for the tallest Differential Scanning Calorimetry ("DSC") peak minus the temperature for the tallest Crystallization Analysis Fractionation ("CRYSTAF") peak and a heat of fusion in J/g, ΔH, and ΔT and ΔH satisfy the following relationships:

$$\Delta T > -0.1299(\Delta H) + 62.81, \text{ and preferably}$$

$$\Delta T \geq -0.1299(\Delta H) + 64.38, \text{ and more preferably}$$

$$\Delta T \geq -0.1299(\Delta H) + 65.95,$$

for ΔH up to 130 J/g. Moreover, ΔT is equal to or greater than 48° C. for ΔH greater than 130 J/g. The CRYSTAF peak is determined using at least 5 percent of the cumulative polymer (that is, the peak must represent at least 5 percent of the cumulative polymer), and if less than 5 percent of the polymer has an identifiable CRYSTAF peak, then the CRYSTAF temperature is 30° C., and ΔH is the numerical value of the heat of fusion in J/g. More preferably, the highest CRYSTAF peak contains at least 10 percent of the cumulative polymer. FIG. 2 shows plotted data for inventive polymers as well as comparative examples. Integrated peak areas and peak temperatures are calculated by the computerized drawing program supplied by the instrument maker. The diagonal line shown for the random ethylene octene comparative polymers corresponds to the equation $\Delta T = -0.1299(\Delta H) + 62.81$.

In yet another aspect, the ethylene/α-olefin interpolymers have a molecular fraction which elutes between 40° C. and 130° C. when fractionated using Temperature Rising Elution Fractionation ("TREF"), characterized in that said fraction has a molar comonomer content higher, preferably at least 5 percent higher, more preferably at least 10 percent higher, than that of a comparable random ethylene interpolymer fraction eluting between the same temperatures, wherein the comparable random ethylene interpolymer contains the same comonomer(s), and has a melt index, density, and molar comonomer content (based on the whole polymer) within 10 percent of that of the block interpolymer. Preferably, the Mw/Mn of the comparable interpolymer is also within 10 percent of that of the block interpolymer and/or the comparable interpolymer has a total comonomer content within 10 weight percent of that of the block interpolymer.

In still another aspect, the ethylene/α-olefin interpolymers are characterized by an elastic recovery, Re, in percent at 300 percent strain and 1 cycle measured on a compression-molded film of an ethylene/α-olefin interpolymer, and has a density, d, in grams/cubic centimeter, wherein the numerical values of Re and d satisfy the following relationship when ethylene/α-olefin interpolymer is substantially free of a cross-linked phase:

$$Re > 1481 - 1629(d); \text{ and preferably}$$

$$Re \geq 1491 - 1629(d); \text{ and more preferably}$$

$$Re \geq 1501 - 1629(d); \text{ and even more preferably}$$

$$Re \geq 1511 - 1629(d).$$

Figure 3:
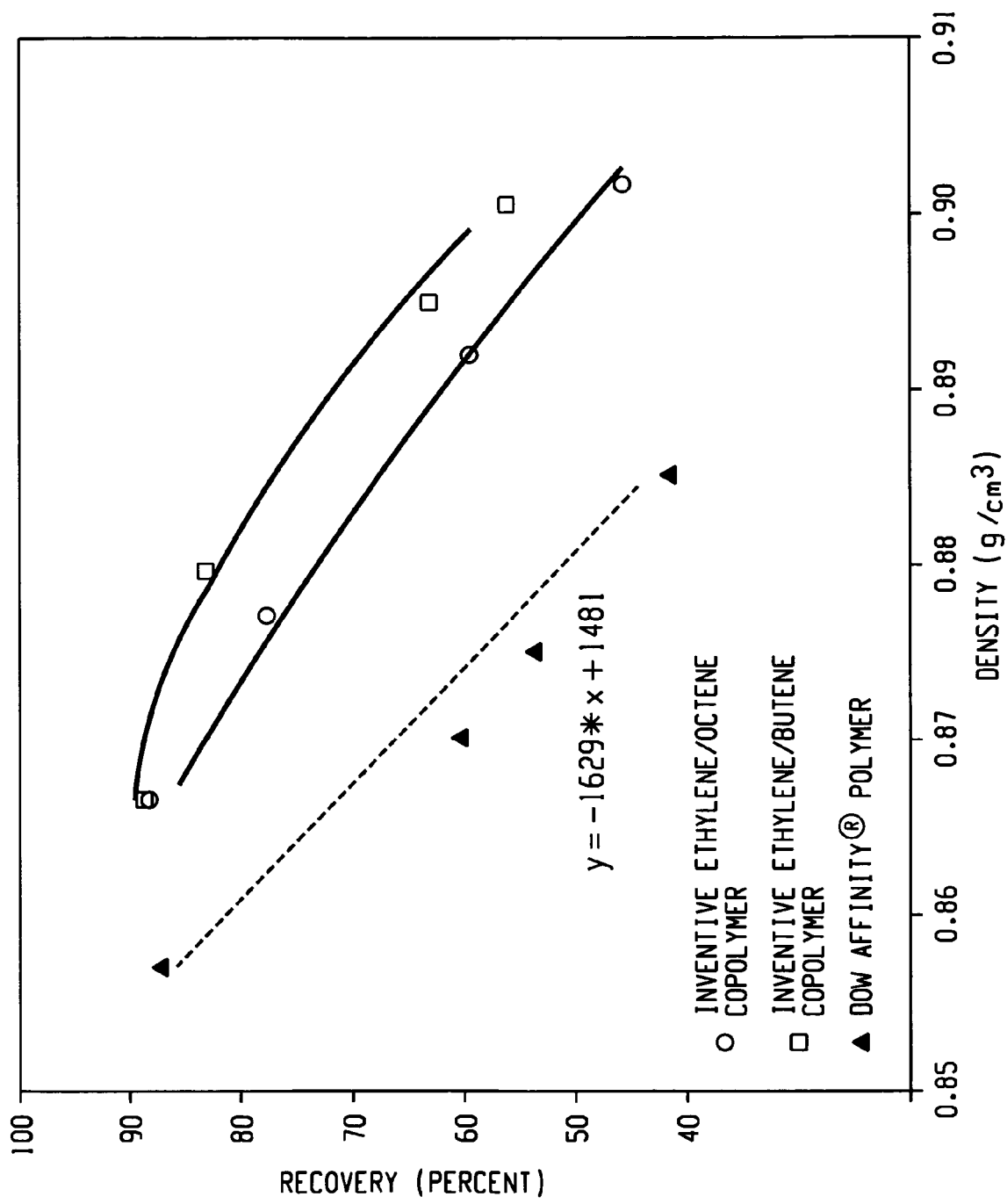
FIG. 3 shows the effect of density on elastic recovery for unoriented films made from the inventive interpolymers (represented by the squares and circles) and traditional copolymers (represented by the triangles which are various Dow AFFINITY® polymers). The squares represent inventive ethylene/butene copolymers; and the circles represent inventive ethylene/octene copolymers.

FIG. 3 shows the effect of density on elastic recovery for unoriented films made from certain inventive interpolymers and traditional random copolymers. For the same density, the inventive interpolymers have substantially higher elastic recoveries.

In some embodiments, the ethylene/α-olefin interpolymers have a tensile strength above 10 MPa, preferably a tensile strength ≧11 MPa, more preferably a tensile strength ≧13 MPa and/or an elongation at break of at least 600 percent, more preferably at least 700 percent, highly preferably at least 800 percent, and most highly preferably at least 900 percent at a crosshead separation rate of 11 cm/minute.

In other embodiments, the ethylene/α-olefin interpolymers have (1) a storage modulus ratio, G'(25° C.)/G'(100° C.), of from 1 to 50, preferably from 1 to 20, more preferably from 1 to 10; and/or (2) a 70° C. compression set of less than 80 percent, preferably less than 70 percent, especially less than 60 percent, less than 50 percent, or less than 40 percent, down to a compression set of 0 percent.

In still other embodiments, the ethylene/α-olefin interpolymers have a 70° C. compression set of less than 80 percent, less than 70 percent, less than 60 percent, or less than 50 percent. Preferably, the 70° C. compression set of the interpolymers is less than 40 percent, less than 30 percent, less than 20 percent, and may go down to about 0 percent.

In some embodiments, the ethylene/α-olefin interpolymers have a heat of fusion of less than 85 J/g and/or a pellet blocking strength of equal to or less than 100 pounds/foot$^2$ (4800 Pa), preferably equal to or less than 50 lbs/ft$^2$ (2400 Pa), especially equal to or less than 5 lbs/ft$^2$ (240 Pa), and as low as 0 lbs/ft$^2$ (0 Pa).

In other embodiments, the ethylene/α-olefin interpolymers comprise, in polymerized form, at least 50 mole percent ethylene and have a 70° C. compression set of less than 80 percent, preferably less than 70 percent or less than 60 percent, most preferably less than 40 to 50 percent and down to close zero percent.

In some embodiments, the multi-block copolymers possess a PDI fitting a Schultz-Flory distribution rather than a Poisson distribution. The copolymers are further characterized as having both a polydisperse block distribution and a polydisperse distribution of block sizes and possessing a most probable distribution of block lengths. Preferred multi-block copolymers are those containing 4 or more blocks or segments including terminal blocks. More preferably, the copolymers include at least 5, 10 or 20 blocks or segments including terminal blocks.

Comonomer content may be measured using any suitable technique, with techniques based on nuclear magnetic resonance ("NMR") spectroscopy preferred. Moreover, for polymers or blends of polymers having relatively broad TREF curves, the polymer desirably is first fractionated using TREF into fractions each having an eluted temperature range of 10° C. or less. That is, each eluted fraction has a collection temperature window of 10° C. or less. Using this technique, said block interpolymers have at least one such fraction having a higher molar comonomer content than a corresponding fraction of the comparable interpolymer.

In another aspect, the inventive polymer is an olefin interpolymer, preferably comprising ethylene and one or more copolymerizable comonomers in polymerized form, characterized by multiple blocks (i.e., at least two blocks) or segments of two or more polymerized monomer units differing in chemical or physical properties (blocked interpolymer), most preferably a multi-block copolymer, said block interpolymer having a peak (but not just a molecular fraction) which elutes between 40° C. and 130° C. (but without collecting and/or isolating individual fractions), characterized in that said peak, has a comonomer content estimated by infra-red spectroscopy when expanded using a full width/half maximum (FWHM) area calculation, has an average molar comonomer content higher, preferably at least 5 percent higher, more preferably at least 10 percent higher, than that of a comparable random ethylene interpolymer peak at the same elution temperature and expanded using a full width/half maximum (FWHM) area calculation, wherein said comparable random ethylene interpolymer has the same comonomer(s) and has a melt index, density, and molar comonomer content (based on the whole polymer) within 10 percent of that of the blocked interpolymer. Preferably, the Mw/Mn of the comparable interpolymer is also within 10 percent of that of the blocked interpolymer and/or the comparable interpolymer has a total comonomer content within 10 weight percent of that of the blocked interpolymer. The full width/half maximum (FWHM) calculation is based on the ratio of methyl to methylene response area [$CH_3/CH_2$] from the ATREF infra-red detector, wherein the tallest (highest) peak is identified from the base line, and then the FWHM area is determined. For a distribution measured using an ATREF peak, the FWHM area is defined as the area under the curve between $T_1$ and $T_2$, where $T_1$ and $T_2$ are points determined, to the left and right of the ATREF peak, by dividing the peak height by two, and then drawing a line horizontal to the base line, that intersects the left and right portions of the ATREF curve. A calibration curve for comonomer content is made using random ethylene/α-olefin copolymers, plotting comonomer content from NMR versus FWHM area ratio of the TREF peak. For this infra-red method, the calibration curve is generated for the same comonomer type of interest. The comonomer content of TREF peak of the inventive polymer can be determined by referencing this calibration curve using its FWHM methyl: methylene area ratio [$CH_3/CH_2$] of the TREF peak.

Comonomer content may be measured using any suitable technique, with techniques based on nuclear magnetic resonance (NMR) spectroscopy preferred. Using this technique, said blocked interpolymers have higher molar comonomer content than a corresponding comparable interpolymer.

Preferably, for interpolymers of ethylene and 1-octene, the block interpolymer has a comonomer content of the TREF fraction eluting between 40 and 130° C. greater than or equal to the quantity (−0.2013)T+20.07, more preferably greater than or equal to the quantity (−0.2013)T+21.07, where T is the numerical value of the peak elution temperature of the TREF fraction being compared, measured in ° C.

Figure 4:
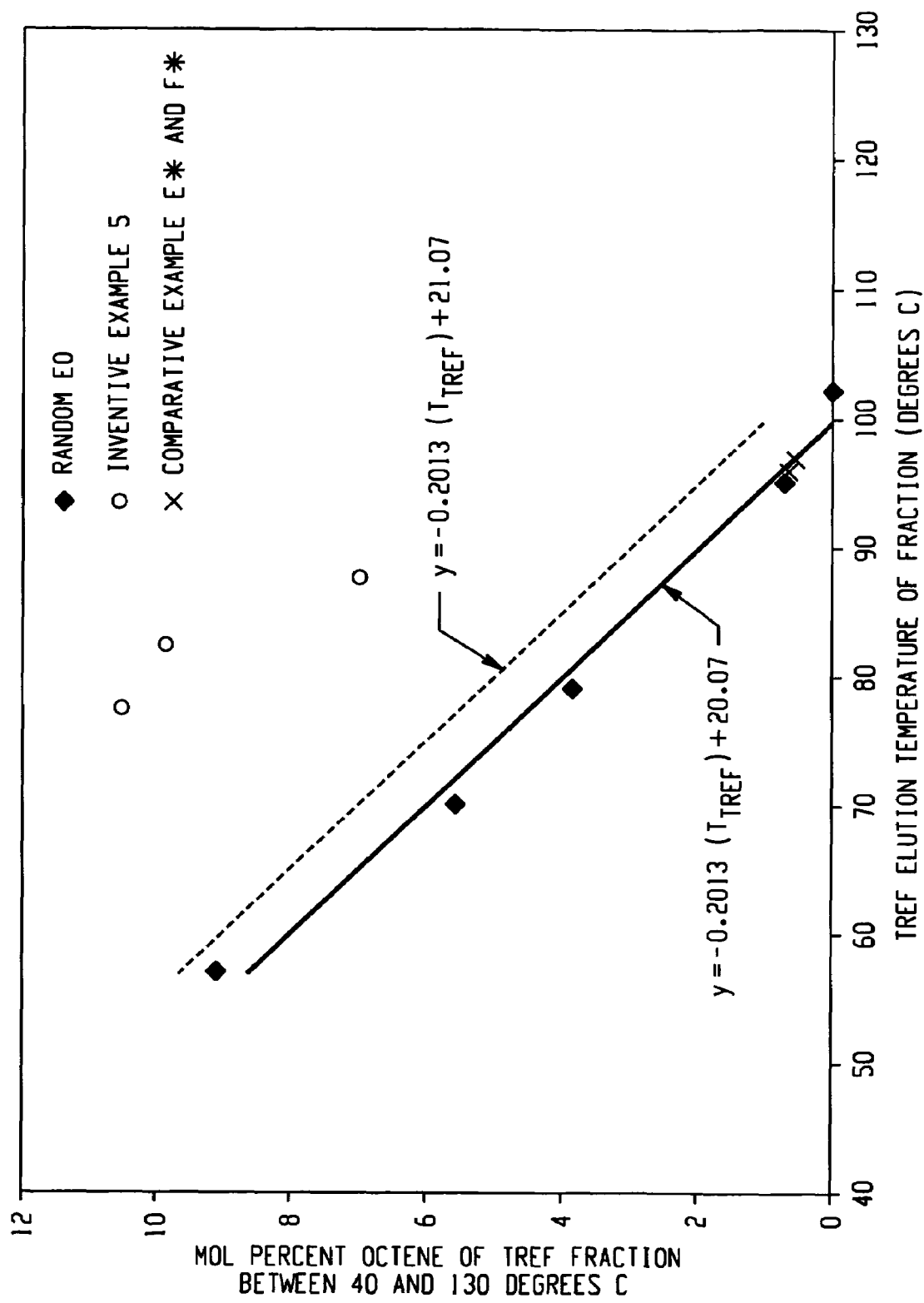
FIG. 4 is a plot of octene content of TREF fractionated ethylene/1-octene copolymer fractions versus TREF elution temperature of the fraction for the polymer of Example 5 (represented by the circles) and Comparative Example E* and F* (represented by the "X" symbols). The diamonds represent traditional random ethylene/octene copolymers.

FIG. 4 graphically depicts an embodiment of the block interpolymers of ethylene and 1-octene where a plot of the comonomer content versus TREF elution temperature for several comparable ethylene/1-octene interpolymers (random copolymers) are fit to a line representing (−0.2013)T+20.07 (solid line). The line for the equation (−0.2013)T+21.07 is depicted by a dotted line. Also depicted are the comonomer contents for fractions of several block ethylene/1-octene interpolymers of the invention (multi-block copolymers). All of the block interpolymer fractions have significantly higher 1-octene content than either line at equivalent elution temperatures. This result is characteristic of the inventive interpolymer and is believed to be due to the presence of differentiated blocks within the polymer chains, having both crystalline and amorphous nature.

Figure 5:
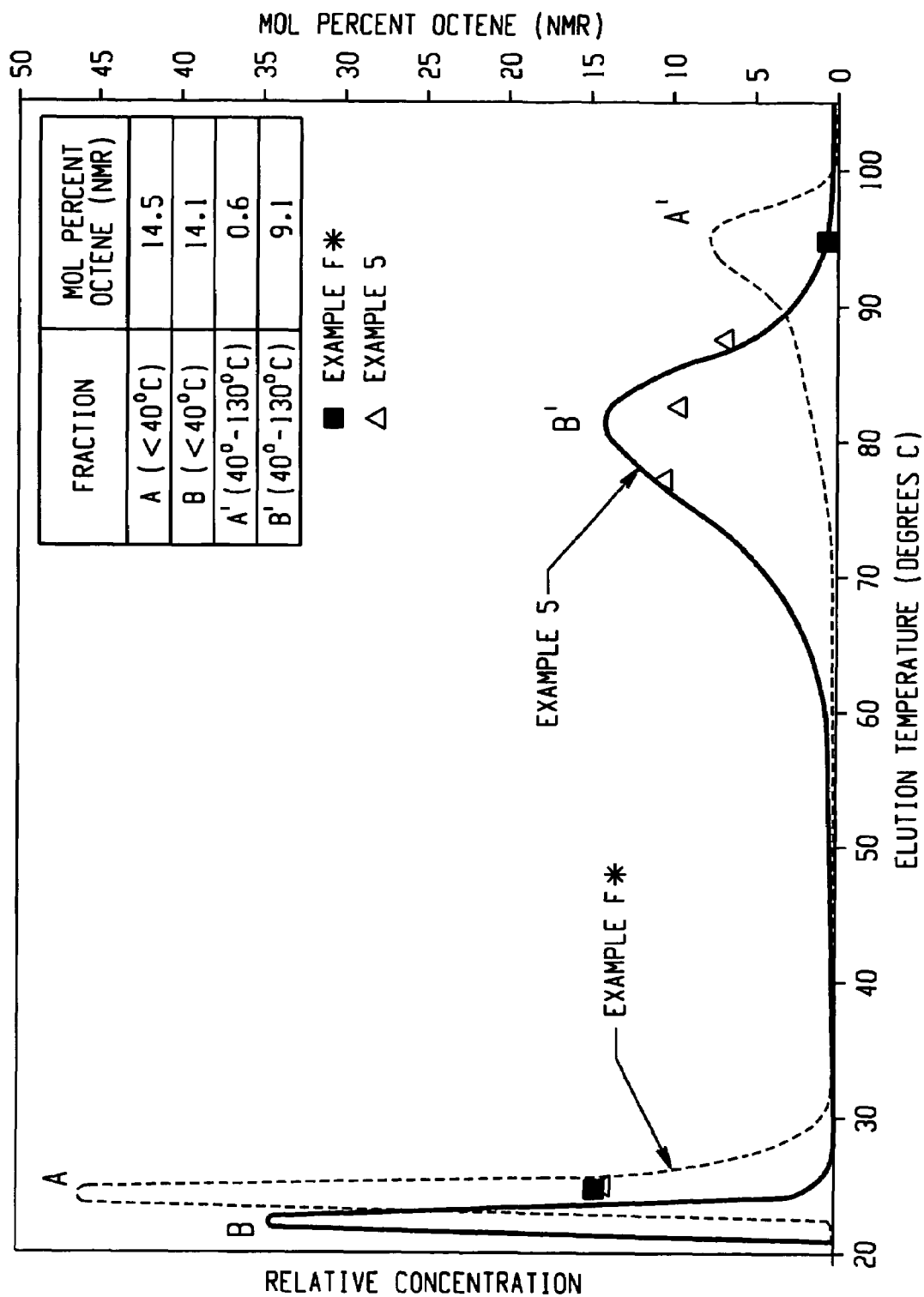
FIG. 5 is a plot of octene content of TREF fractionated ethylene/1-octene copolymer fractions versus TREF elution temperature of the fraction for the polymer of Example 5 (curve 1) and for Comparative Example F* (curve 2). The squares represent Example F*; and the triangles represent Example 5.

FIG. 5 graphically displays the TREF curve and comonomer contents of polymer fractions for Example 5 and Comparative Example F* to be discussed below. The peak eluting from 40 to 130° C., preferably from 60° C. to 95° C. for both polymers is fractionated into three parts, each part eluting over a temperature range of less than 10° C. Actual data for Example 5 is represented by triangles. The skilled artisan can appreciate that an appropriate calibration curve may be constructed for interpolymers containing different comonomers and a line used as a comparison fitted to the TREF values obtained from comparative interpolymers of the same monomers, preferably random copolymers made using a metallocene or other homogeneous catalyst composition. Inventive interpolymers are characterized by a molar comonomer content greater than the value determined from the calibration curve at the same TREF elution temperature, preferably at least 5 percent greater, more preferably at least 10 percent greater.

In addition to the above aspects and properties described herein, the inventive polymers can be characterized by one or more additional characteristics. In one aspect, the inventive polymer is an olefin interpolymer, preferably comprising ethylene and one or more copolymerizable comonomers in polymerized form, characterized by multiple blocks or segments of two or more polymerized monomer units differing in chemical or physical properties (blocked interpolymer), most preferably a multi-block copolymer, said block interpolymer having a molecular fraction which elutes between 40° C. and 130° C., when fractionated using TREF increments, characterized in that said fraction has a molar comonomer content higher, preferably at least 5 percent higher, more preferably at least 10, 15, 20 or 25 percent higher, than that of a comparable random ethylene interpolymer fraction eluting between the same temperatures, wherein said comparable random ethylene interpolymer comprises the same comonomer(s), preferably it is the same comonomer(s), and a melt index, density, and molar comonomer content (based on the whole polymer) within 10 percent of that of the blocked interpolymer. Preferably, the Mw/Mn of the comparable interpolymer is also within 10 percent of that of the blocked interpolymer and/or the comparable interpolymer has a total comonomer content within 10 weight percent of that of the blocked interpolymer.

Preferably, the above interpolymers are interpolymers of ethylene and at least one α-olefin, especially those interpolymers having a whole polymer density from about 0.855 to about 0.935 g/cm$^3$, and more especially for polymers having more than about 1 mole percent comonomer, the blocked interpolymer has a comonomer content of the TREF fraction eluting between 40 and 130° C. greater than or equal to the quantity $(-0.1356)T+13.89$, more preferably greater than or equal to the quantity $(-0.1356)T+14.93$, and most preferably greater than or equal to the quantity $(-0.2013)T+21.07$, where T is the numerical value of the peak ATREF elution temperature of the TREF fraction being compared, measured in ° C.

Preferably, for the above interpolymers of ethylene and at least one alpha-olefin especially those interpolymers having a whole polymer density from about 0.855 to about 0.935 g/cm$^3$, and more especially for polymers having more than about 1 mole percent comonomer, the blocked interpolymer has a comonomer content of the TREF fraction eluting between 40 and 130° C. greater than or equal to the quantity $(-0.2013)T+20.07$, more preferably greater than or equal to the quantity $(-0.2013)T+21.07$, where T is the numerical value of the peak elution temperature of the TREF fraction being compared, measured in ° C.

In still another aspect, the inventive polymer is an olefin interpolymer, preferably comprising ethylene and one or more copolymerizable comonomers in polymerized form, characterized by multiple blocks or segments of two or more polymerized monomer units differing in chemical or physical properties (blocked interpolymer), most preferably a multi-block copolymer, said block interpolymer having a molecular fraction which elutes between 40° C. and 130° C., when fractionated using TREF increments, characterized in that every fraction having a comonomer content of at least about 6 mole percent, has a melting point greater than about 100° C. For those fractions having a comonomer content from about 3 mole percent to about 6 mole percent, every fraction has a DSC melting point of about 110° C. or higher. More preferably, said polymer fractions, having at least 1 mol percent comonomer, has a DSC melting point that corresponds to the equation:

$$Tm \geq (-5.5926)(\text{mol percent comonomer in the fraction}) + 135.90.$$

In yet another aspect, the inventive polymer is an olefin interpolymer, preferably comprising ethylene and one or more copolymerizable comonomers in polymerized form, characterized by multiple blocks or segments of two or more polymerized monomer units differing in chemical or physical properties (blocked interpolymer), most preferably a multi-block copolymer, said block interpolymer having a molecular fraction which elutes between 40° C. and 130° C., when fractionated using TREF increments, characterized in that every fraction that has an ATREF elution temperature greater than or equal to about 76° C., has a melt enthalpy (heat of fusion) as measured by DSC, corresponding to the equation:

$$\text{Heat of fusion}(J/gm) \leq (3.1718)(\text{ATREF elution temperature in Celsius}) - 136.58,$$

The inventive block interpolymers have a molecular fraction which elutes between 40° C. and 130° C., when fractionated using TREF increments, characterized in that every fraction that has an ATREF elution temperature between 40° C. and less than about 76° C., has a melt enthalpy (heat of fusion) as measured by DSC, corresponding to the equation:

$$\text{Heat of fusion}(J/gm) \leq (1.1312)(\text{ATREF elution temperature in Celsius}) + 22.97.$$

ATREF Peak Comonomer Composition Measurement by Infra-Red Detector

The comonomer composition of the TREF peak can be measured using an IR4 infra-red detector available from Polymer Char, Valencia, Spain (http://www.polymerchar.com/).

The "composition mode" of the detector is equipped with a measurement sensor ($CH_2$) and composition sensor ($CH_3$) that are fixed narrow band infra-red filters in the region of 2800-3000 cm$^{-1}$. The measurement sensor detects the methylene ($CH_2$) carbons on the polymer (which directly relates to the polymer concentration in solution) while the composition sensor detects the methyl ($CH_3$) groups of the polymer. The mathematical ratio of the composition signal ($CH_3$) divided by the measurement signal ($CH_2$) is sensitive to the comonomer content of the measured polymer in solution and its response is calibrated with known ethylene alpha-olefin copolymer standards.

The detector when used with an ATREF instrument provides both a concentration ($CH_2$) and composition ($CH_3$) signal response of the eluted polymer during the TREF process. A polymer specific calibration can be created by measuring the area ratio of the $CH_3$ to $CH_2$ for polymers with known comonomer content (preferably measured by NMR). The comonomer content of an ATREF peak of a polymer can be estimated by applying a reference calibration of the ratio of the areas for the individual $CH_3$ and $CH_2$ response (i.e. area ratio $CH_3/CH_2$ versus comonomer content).

The area of the peaks can be calculated using a full width/half maximum (FWHM) calculation after applying the appropriate baselines to integrate the individual signal responses from the TREF chromatogram. The full width/half maximum calculation is based on the ratio of methyl to methylene response area [$CH_3/CH_2$] from the ATREF infra-red detector, wherein the tallest (highest) peak is identified from the base line, and then the FWHM area is determined. For a distribution measured using an ATREF peak, the FWHM area is defined as the area under the curve between T1 and T2, where T1 and T2 are points determined, to the left and right of the ATREF peak, by dividing the peak height by two, and then drawing a line horizontal to the base line, that intersects the left and right portions of the ATREF curve.

The application of infra-red spectroscopy to measure the comonomer content of polymers in this ATREF-infra-red method is, in principle, similar to that of GPC/FTIR systems as described in the following references: Markovich, Ronald P.; Hazlitt, Lonnie G.; Smith, Linley; "Development of gel-permeation chromatography-Fourier transform infrared spectroscopy for characterization of ethylene-based polyolefin copolymers", Polymeric Materials Science and Engineering (1991), 65, 98-100; and Deslauriers, P. J.; Rohlfing, D. C.; Shieh, E. T.; "Quantifying short chain branching microstructures in ethylene-1-olefin copolymers using size exclusion chromatography and Fourier transform infrared spectroscopy (SEC-FTIR)", Polymer (2002), 43, 59-170, both of which are incorporated by reference herein in their entirety.

In other embodiments, the inventive ethylene/α-olefin interpolymer is characterized by an average block index, ABI, which is greater than zero and up to about 1.0 and a molecular weight distribution, $M_w/M_n$, greater than about 1.3. The average block index, ABI, is the weight average of the block index ("BI") for each of the polymer fractions obtained in preparative TREF from 20° C. and 110° C., with an increment of 5° C.:

$$ABI = \Sigma(w_i BI_i)$$

where $BI_i$ is the block index for the ith fraction of the inventive ethylene/α-olefin interpolymer obtained in preparative TREF, and $w_i$ is the weight percentage of the ith fraction.

For each polymer fraction, BI is defined by one of the two following equations (both of which give the same BI value):

$$BI = \frac{1/T_X - 1/T_{XO}}{1/T_A - 1/T_{AB}} \text{ or } BI = -\frac{LnP_X - LnP_{XO}}{LnP_A - LnP_{AB}}$$

where $T_X$ is the preparative ATREF elution temperature for the ith fraction (preferably expressed in Kelvin), $P_X$ is the ethylene mole fraction for the ith fraction, which can be measured by NMR or IR as described above. $P_{AB}$ is the ethylene mole fraction of the whole ethylene/α-olefin interpolymer (before fractionation), which also can be measured by NMR or IR. $T_A$ and $P_A$ are the ATREF elution temperature and the ethylene mole fraction for pure "hard segments" (which refer to the crystalline segments of the interpolymer). As a first order approximation, the $T_A$ and $P_A$ values are set to those for high density polyethylene homopolymer, if the actual values for the "hard segments" are not available. For calculations performed herein, $T_A$ is 372° K, $P_A$ is 1.

$T_{AB}$ is the ATREF temperature for a random copolymer of the same composition and having an ethylene mole fraction of $P_{AB}$. $T_{AB}$ can be calculated from the following equation:

$$Ln P_{AB} = \alpha/T_{AB} + \beta$$

where α and β are two constants which can be determined by calibration using a number of known random ethylene copolymers. It should be noted that α and β may vary from instrument to instrument. Moreover, one would need to create their own calibration curve with the polymer composition of interest and also in a similar molecular weight range as the fractions. There is a slight molecular weight effect. If the calibration curve is obtained from similar molecular weight ranges, such effect would be essentially negligible. In some embodiments, random ethylene copolymers satisfy the following relationship:

$$Ln P = -237.83/T_{ATREF} + 0.639$$

$T_{XO}$ is the ATREF temperature for a random copolymer of the same composition and having an ethylene mole fraction of $P_X$. $T_{XO}$ can be calculated from $LnP_X = \alpha/T_{XO} + \beta$. Conversely, $P_{XO}$ is the ethylene mole fraction for a random copolymer of the same composition and having an ATREF temperature of $T_X$, which can be calculated from $Ln P_{XO} = \alpha/T_X + \beta$.

Once the block index (BI) for each preparative TREF fraction is obtained, the weight average block index, ABI, for the whole polymer can be calculated. In some embodiments, ABI is greater than zero but less than about 0.3 or from about 0.1 to about 0.3. In other embodiments, ABI is greater than about 0.3 and up to about 1.0. Preferably, ABI should be in the range of from about 0.4 to about 0.7, from about 0.5 to about 0.7, or from about 0.6 to about 0.9. In some embodiments, ABI is in the range of from about 0.3 to about 0.9, from about 0.3 to about 0.8, or from about 0.3 to about 0.7, from about 0.3 to about 0.6, from about 0.3 to about 0.5, or from about 0.3 to about 0.4. In other embodiments, ABI is in the range of from about 0.4 to about 1.0, from about 0.5 to about 1.0, or from about 0.6 to about 1.0, from about 0.7 to about 1.0, from about 0.8 to about 1.0, or from about 0.9 to about 1.0.

Another characteristic of the inventive ethylene/α-olefin interpolymer is that the inventive ethylene/α-olefin interpolymer comprises at least one polymer fraction which can be obtained by preparative TREF, wherein the fraction has a block index greater than about 0.1 and up to about 1.0 and a molecular weight distribution, $M_w/M_n$, greater than about 1.3. In some embodiments, the polymer fraction has a block index greater than about 0.6 and up to about 1.0, greater than about 0.7 and up to about 1.0, greater than about 0.8 and up to about 1.0, or greater than about 0.9 and up to about 1.0. In other embodiments, the polymer fraction has a block index greater than about 0.1 and up to about 1.0, greater than about 0.2 and up to about 1.0, greater than about 0.3 and up to about 1.0, greater than about 0.4 and up to about 1.0, or greater than about 0.4 and up to about 1.0. In still other embodiments, the polymer fraction has a block index greater than about 0.1 and up to about 0.5, greater than about 0.2 and up to about 0.5, greater than about 0.3 and up to about 0.5, or greater than about 0.4 and up to about 0.5. In yet other embodiments, the polymer fraction has a block index greater than about 0.2 and up to about 0.9, greater than about 0.3 and up to about 0.8, greater than about 0.4 and up to about 0.7, or greater than about 0.5 and up to about 0.6.

For copolymers of ethylene and an α-olefin, the inventive polymers preferably possess (1) a PDI of at least 1.3, more preferably at least 1.5, at least 1.7, or at least 2.0, and most preferably at least 2.6, up to a maximum value of 5.0, more preferably up to a maximum of 3.5, and especially up to a maximum of 2.7; (2) a heat of fusion of 80 J/g or less; (3) an ethylene content of at least 50 weight percent; (4) a glass transition temperature, $T_g$, of less than −25° C., more preferably less than −30° C., and/or (5) one and only one $T_m$.

Figure 6:
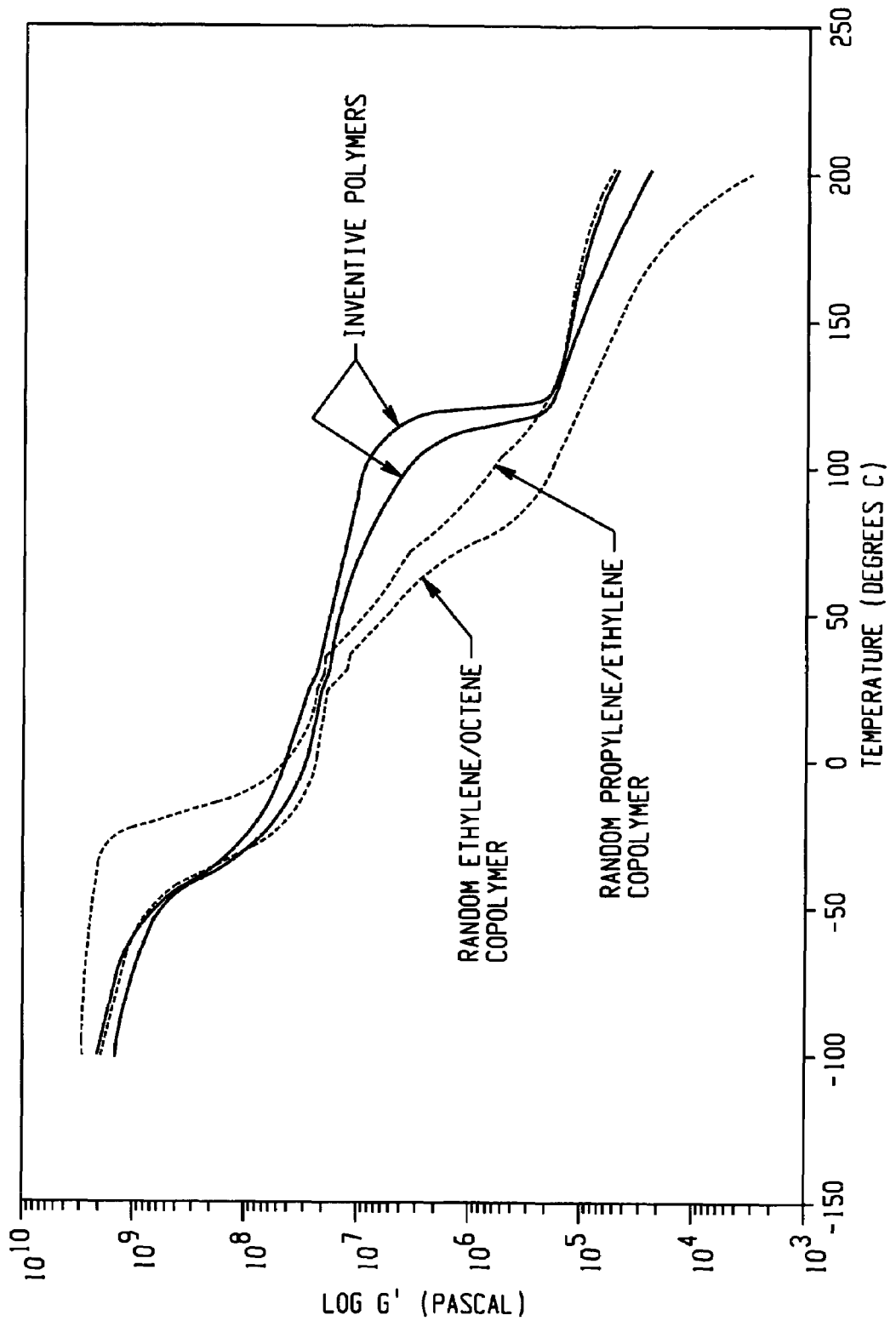
FIG. 6 is a graph of the log of storage modulus as a function of temperature for comparative ethylene/1-octene copolymer (curve 2) and propylene/ethylene-copolymer (curve 3) and for two ethylene/1-octene block copolymers of the invention made with differing quantities of chain shuttling agent (curves 1).

Further, the inventive polymers can have, alone or in combination with any other properties disclosed herein, a storage modulus, G', such that log (G') is greater than or equal to 400 kPa, preferably greater than or equal to 1.0 MPa, at a temperature of 100° C. Moreover, the inventive polymers possess a relatively flat storage modulus as a function of temperature in the range from 0 to 100° C. (illustrated in FIG. 6) that is characteristic of block copolymers, and heretofore unknown for an olefin copolymer, especially a copolymer of ethylene and one or more $C_{3-8}$ aliphatic α-olefins. (By the term "relatively flat" in this context is meant that log G' (in Pascals) decreases by less than one order of magnitude between 50 and 100° C., preferably between 0 and 100° C.).

Figure 7:
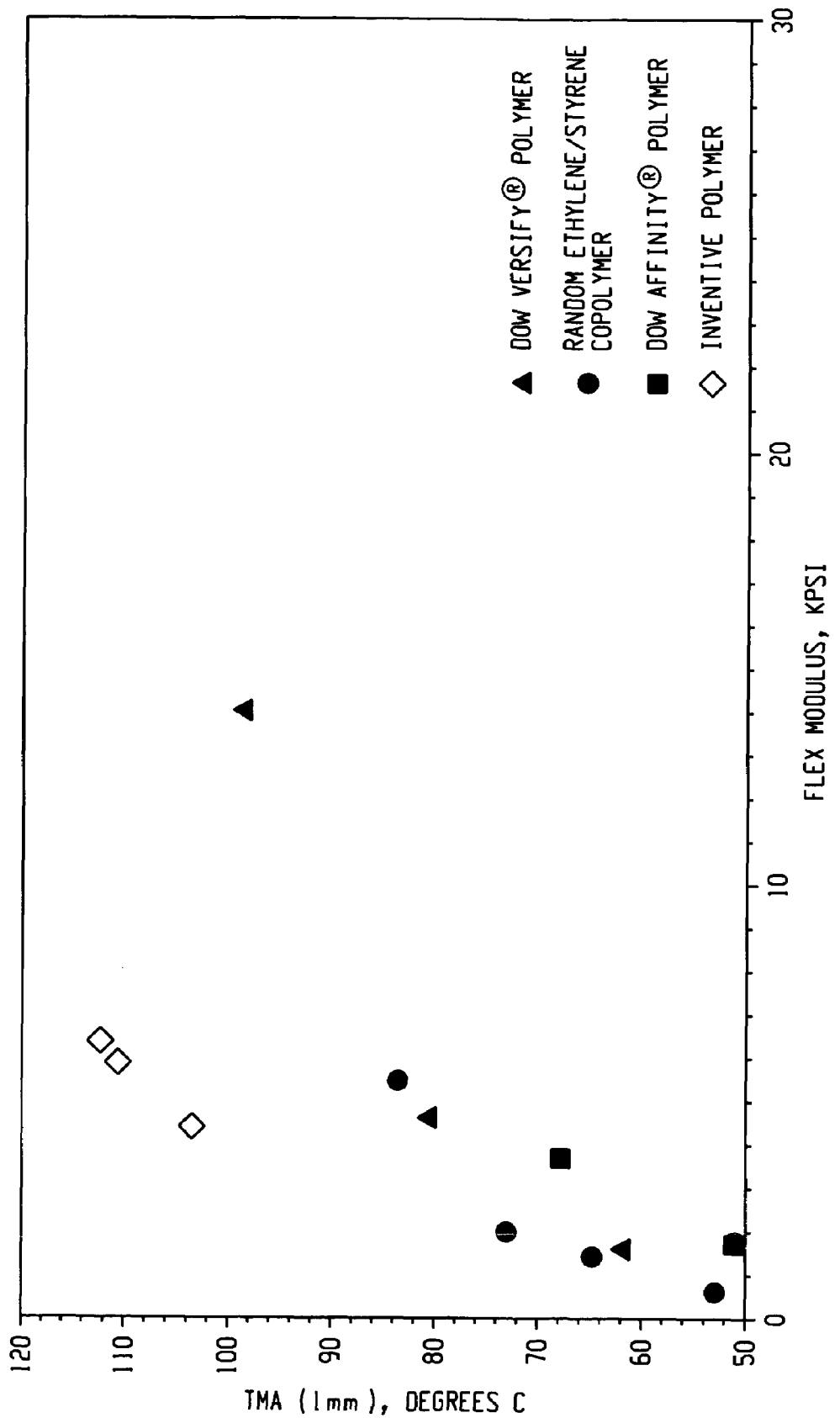
FIG. 7 shows a plot of TMA (1 mm) versus flex modulus for some inventive polymers (represented by the diamonds), as compared to some known polymers. The triangles represent various Dow VERSIFY® polymers; the circles represent various random ethylene/styrene copolymers; and the squares represent various Dow AFFINITY® polymers.

The inventive interpolymers may be further characterized by a thermomechanical analysis penetration depth of 1 mm at a temperature of at least 90° C. as well as a flexural modulus of from 3 kpsi (20 MPa) to 13 kpsi (90 MPa). Alternatively, the inventive interpolymers can have a thermomechanical analysis penetration depth of 1 mm at a temperature of at least 104° C. as well as a flexural modulus of at least 3 kpsi (20 MPa). They may be characterized as having an abrasion resistance (or volume loss) of less than 90 $mm^3$. FIG. 7 shows the TMA (1 mm) versus flex modulus for the inventive polymers, as compared to other known polymers. The inventive polymers have significantly better flexibility-heat resistance balance than the other polymers.

Additionally, the ethylene/α-olefin interpolymers can have a melt index, $I_2$, from 0.01 to 2000 g/10 minutes, preferably from 0.01 to 1000 g/10 minutes, more preferably from 0.01 to 500 g/10 minutes, and especially from 0.01 to 100 g/10 minutes. In certain embodiments, the ethylene/α-olefin interpolymers have a melt index, $I_2$, from 0.01 to 10 g/10 minutes, from 0.5 to 50 g/10 minutes, from 1 to 30 g/10 minutes, from 1 to 6 g/10 minutes or from 0.3 to 10 g/10 minutes. In certain embodiments, the melt index for the ethylene/α-olefin polymers is 1 g/10 minutes, 3 g/10 minutes or 5 g/10 minutes.

The polymers can have molecular weights, $M_w$, from 1,000 g/mole to 5,000,000 g/mole, preferably from 1000 g/mole to 1,000,000, more preferably from 10,000 g/mole to 500,000 g/mole, and especially from 10,000 g/mole to 300,000 g/mole. The density of the inventive polymers can be from 0.80 to 0.99 $g/cm^3$ and preferably for ethylene containing polymers from 0.85 $g/cm^3$ to 0.97 $g/cm^3$. In certain embodiments, the density of the ethylene/α-olefin polymers ranges from 0.860 to 0.925 $g/cm^3$ or 0.867 to 0.910 $g/cm^3$.

The process of making the polymers has been disclosed in the following patent applications: U.S. Provisional Application No. 60/553,906, filed Mar. 17, 2004; U.S. Provisional Application No. 60/662,937, filed Mar. 17, 2005; U.S. Provisional Application No. 60/662,939, filed Mar. 17, 2005; U.S. Provisional Application No. 60/5662938, filed Mar. 17, 2005; PCT Application No. PCT/US2005/008916, filed Mar. 17, 2005; PCT Application No. PCT/US2005/008915, filed Mar. 17, 2005; and PCT Application No. PCT/US2005/008917, filed Mar. 17, 2005, all of which are incorporated by reference herein in their entirety. For example, one such method comprises contacting ethylene and optionally one or more addition polymerizable monomers other than ethylene under addition polymerization conditions with a catalyst composition comprising:

the admixture or reaction product resulting from combining:
 a. a first olefin polymerization catalyst having a high comonomer incorporation index,
 b. a second olefin polymerization catalyst having a comonomer incorporation index less than 90 percent, preferably less than 50 percent, most preferably less than 5 percent of the comonomer incorporation index of catalyst (A), and
 c. a chain shuttling agent.

Representative catalysts and chain shuttling agent are as follows.

Catalyst (A1) is [N-(2,6-di(1-methylethyl)phenyl)amido) (2-isopropylphenyl)(α-naphthalen-2-diyl(6-pyridin-2-diyl) methane)]hafnium dimethyl, prepared according to the teachings of WO 03/40195, 2003US0204017, U.S. Ser. No. 10/429,024, filed May 2, 2003, and WO 04/24740.

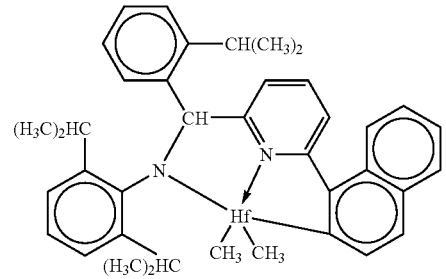

Catalyst (A2) is [N-(2,6-di(1-methylethyl)phenyl)amido) (2-methylphenyl)(1,2-phenylene-(6-pyridin-2-diyl)methane)]hafnium dimethyl, prepared according to the teachings of WO 03/40195, 2003US0204017, U.S. Ser. No. 10/429, 024, filed May 2, 2003, and WO 04/24740.

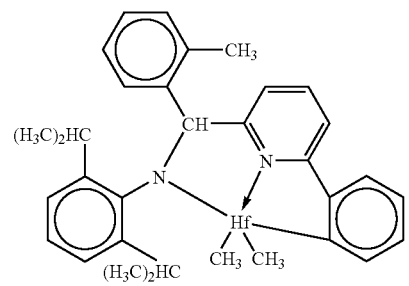

Catalyst (A3) is bis[N,N'''-(2,4,6-tri(methylphenyl)amido) ethylenediamine]hafnium dibenzyl.

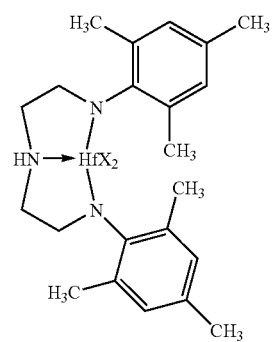

X = $CH_2C_6H_5$

Catalyst (A4) is bis((2-oxoyl-3-(dibenzo-1H-pyrrole-1-yl)-5-(methyl)phenyl)-2-phenoxymethyl)cyclohexane-1,2-diyl zirconium (IV) dibenzyl, prepared substantially according to the teachings of US-A-2004/0010103.

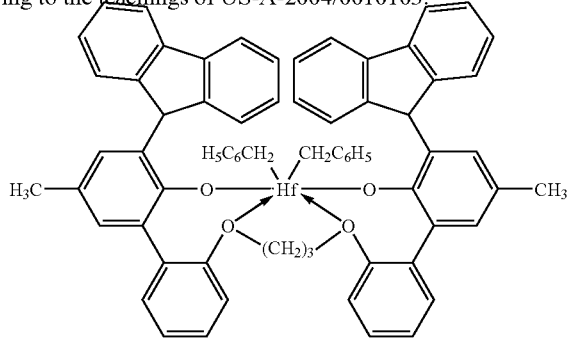

Catalyst (B1) is 1,2-bis-(3,5-di-t-butylphenylene)(1-(N-(1-methylethyl)immino)methyl)(2-oxoyl)zirconium dibenzyl

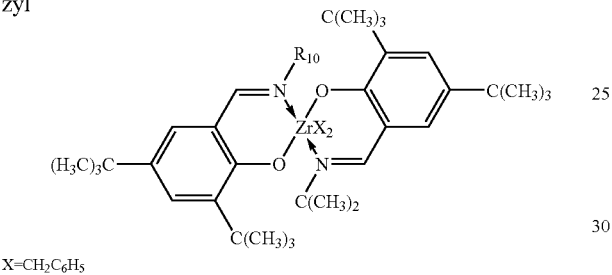

Catalyst (B2) is 1,2-bis-(3,5-di-t-butylphenylene)(1-(N-(2-methylcyclohexyl)-immino)methyl)(2-oxoyl)zirconium dibenzyl

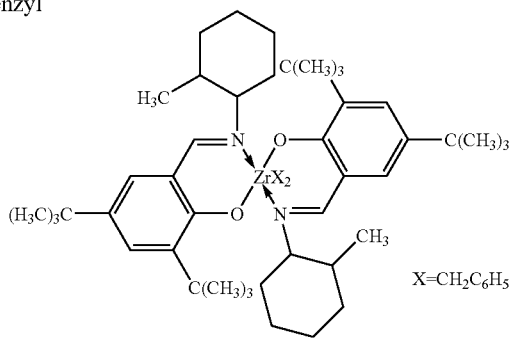

Catalyst (C1) is (t-butylamido)dimethyl(3-N-pyrrolyl-1,2,3,3a,7a-η-inden-1-yl)silanetitanium dimethyl prepared substantially according to the techniques of U.S. Pat. No. 6,268,444:

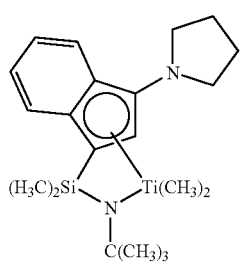

Catalyst (C2) is (t-butylamido)di(4-methylphenyl)(2-methyl-1,2,3,3a,7a-η-inden-1-yl)silanetitanium dimethyl prepared substantially according to the teachings of US-A-2003/004286:

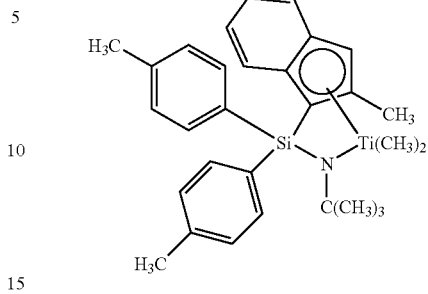

Catalyst (C3) is (t-butylamido)di(4-methylphenyl)(2-methyl-1,2,3,3a,8a-η-s-indacen-1-yl)silanetitanium dimethyl prepared substantially according to the teachings of US-A-2003/004286:

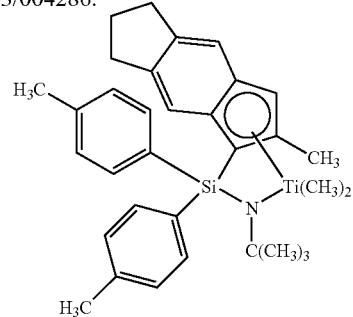

Catalyst (D1) is bis(dimethyldisiloxane)(indene-1-yl)zirconium dichloride available from Sigma-Aldrich:

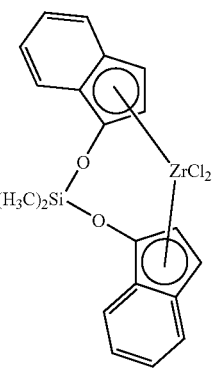

Shuttling Agents The shuttling agents employed include diethylzinc, di(i-butyl)zinc, di(n-hexyl)zinc, triethylaluminum, trioctylaluminum, triethylgallium, i-butylaluminum bis(dimethyl(t-butyl)siloxane), i-butylaluminum bis(di(trimethylsilyl)amide), n-octylaluminum di(pyridine-2-methoxide), bis(n-octadecyl)i-butylaluminum, i-butylaluminum bis(di(n-pentyl)amide), n-octylaluminum bis(2,6-di-t-butylphenoxide, n-octylaluminum di(ethyl(1-naphthyl)amide), ethylaluminum bis(t-butyldimethylsiloxide), ethylaluminum di(bis(trimethylsilyl)amide), ethylaluminum bis(2,3,6,7-dibenzo-1-azacycloheptaneamide), n-octylaluminum bis(2,3,6,7-dibenzo-1-azacycloheptaneamide), n-octylaluminum bis(dimethyl(t-butyl)siloxide), ethylzinc (2,6-diphenylphenoxide), and ethylzinc (t-butoxide).

Preferably, the foregoing process takes the form of a continuous solution process for forming block copolymers, especially multi-block copolymers, preferably linear multi-block copolymers of two or more monomers, more especially ethylene and a $C_{3-20}$ olefin or cycloolefin, and most especially ethylene and a $C_{4-20}$ α-olefin, using multiple catalysts that are incapable of interconversion. That is, the catalysts are chemically distinct. Under continuous solution polymerization conditions, the process is ideally suited for polymerization of mixtures of monomers at high monomer conversions. Under these polymerization conditions, shuttling from the chain shuttling agent to the catalyst becomes advantaged compared to chain growth, and multi-block copolymers, especially linear multi-block copolymers are formed in high efficiency.

The inventive interpolymers may be differentiated from conventional, random copolymers, physical blends of polymers, and block copolymers prepared via sequential monomer addition, fluxional catalysts, anionic or cationic living polymerization techniques. In particular, compared to a random copolymer of the same monomers and monomer content at equivalent crystallinity or modulus, the inventive interpolymers have better (higher) heat resistance as measured by melting point, higher TMA penetration temperature, higher high-temperature tensile strength, and/or higher high-temperature torsion storage modulus as determined by dynamic mechanical analysis. Compared to a random copolymer containing the same monomers and monomer content, the inventive interpolymers have lower compression set, particularly at elevated temperatures, lower stress relaxation, higher creep resistance, higher tear strength, higher blocking resistance, faster setup due to higher crystallization (solidification) temperature, higher recovery (particularly at elevated temperatures), better abrasion resistance, higher retractive force, and better oil and filler acceptance.

The inventive interpolymers also exhibit a unique crystallization and branching distribution relationship. That is, the inventive interpolymers have a relatively large difference between the tallest peak temperature measured using CRYSTAF and DSC as a function of heat of fusion, especially as compared to random copolymers containing the same monomers and monomer level or physical blends of polymers, such as a blend of a high density polymer and a lower density copolymer, at equivalent overall density. It is believed that this unique feature of the inventive interpolymers is due to the unique distribution of the comonomer in blocks within the polymer backbone. In particular, the inventive interpolymers may comprise alternating blocks of differing comonomer content (including homopolymer blocks). The inventive interpolymers may also comprise a distribution in number and/or block size of polymer blocks of differing density or comonomer content, which is a Schultz-Flory type of distribution. In addition, the inventive interpolymers also have a unique peak melting point and crystallization temperature profile that is substantially independent of polymer density, modulus, and morphology. In a preferred embodiment, the microcrystalline order of the polymers demonstrates characteristic spherulites and lamellae that are distinguishable from random or block copolymers, even at PDI values that are less than 1.7, or even less than 1.5, down to less than 1.3.

Moreover, the inventive interpolymers may be prepared using techniques to influence the degree or level of blockiness. That is the amount of comonomer and length of each polymer block or segment can be altered by controlling the ratio and type of catalysts and shuttling agent as well as the temperature of the polymerization, and other polymerization variables. A surprising benefit of this phenomenon is the discovery that as the degree of blockiness is increased, the optical properties, tear strength, and high temperature recovery properties of the resulting polymer are improved. In particular, haze decreases while clarity, tear strength, and high temperature recovery properties increase as the average number of blocks in the polymer increases. By selecting shuttling agents and catalyst combinations having the desired chain transferring ability (high rates of shuttling with low levels of chain termination) other forms of polymer termination are effectively suppressed. Accordingly, little if any β-hydride elimination is observed in the polymerization of ethylene/α-olefin comonomer mixtures according to embodiments of the invention, and the resulting crystalline blocks are highly, or substantially completely, linear, possessing little or no long chain branching.

Polymers with highly crystalline chain ends can be selectively prepared in accordance with embodiments of the invention. In elastomer applications, reducing the relative quantity of polymer that terminates with an amorphous block reduces the intermolecular dilutive effect on crystalline regions. This result can be obtained by choosing chain shuttling agents and catalysts having an appropriate response to hydrogen or other chain terminating agents. Specifically, if the catalyst which produces highly crystalline polymer is more susceptible to chain termination (such as by use of hydrogen) than the catalyst responsible for producing the less crystalline polymer segment (such as through higher comonomer incorporation, regio-error, or atactic polymer formation), then the highly crystalline polymer segments will preferentially populate the terminal portions of the polymer. Not only are the resulting terminated groups crystalline, but upon termination, the highly crystalline polymer forming catalyst site is once again available for reinitiation of polymer formation. The initially formed polymer is therefore another highly crystalline polymer segment. Accordingly, both ends of the resulting multi-block copolymer are preferentially highly crystalline.

The ethylene α-olefin interpolymers used in the embodiments of the invention are preferably interpolymers of ethylene with at least one $C_3$-$C_{20}$ α-olefin. Copolymers of ethylene and a $C_3$-$C_{20}$ α-olefin are especially preferred. The interpolymers may further comprise $C_4$-$C_{18}$ diolefin and/or alkenylbenzene. Suitable unsaturated comonomers useful for polymerizing with ethylene include, for example, ethylenically unsaturated monomers, conjugated or nonconjugated dienes, polyenes, alkenylbenzenes, etc. Examples of such comonomers include $C_3$-$C_{20}$ α-olefins such as propylene, isobutylene, 1-butene, 1-hexene, 1-pentene, 4-methyl-1-pentene, 1-heptene, 1-octene, 1-nonene, 1-decene, and the like. 1-Butene and 1-octene are especially preferred. Other suitable monomers include styrene, halo- or alkyl-substituted styrenes, vinylbenzocyclobutane, 1,4-hexadiene, 1,7-octadiene, and naphthenics (e.g., cyclopentene, cyclohexene and cyclooctene).

While ethylene/α-olefin interpolymers are preferred polymers, other ethylene/olefin polymers may also be used. Olefins as used herein refer to a family of unsaturated hydrocarbon-based compounds with at least one carbon-carbon double bond. Depending on the selection of catalysts, any olefin may be used in embodiments of the invention. Preferably, suitable olefins are $C_3$-$C_{20}$ aliphatic and aromatic compounds containing vinylic unsaturation, as well as cyclic compounds, such as cyclobutene, cyclopentene, dicyclopentadiene, and norbornene, including but not limited to, norbornene substituted in the 5 and 6 position with $C_1$-$C_{20}$ hydrocarbyl or cyclohydrocarbyl groups. Also included are mixtures of such olefins as well as mixtures of such olefins with $C_4$-$C_{40}$ diolefin compounds.

Examples of olefin monomers include, but are not limited to propylene, isobutylene, 1-butene, 1-pentene, 1-hexene, 1-heptene, 1-octene, 1-nonene, 1-decene, and 1-dodecene, 1-tetradecene, 1-hexadecene, 1-octadecene, 1-eicosene, 3-methyl-1-butene, 3-methyl-1-pentene, 4-methyl-1-pentene, 4,6-dimethyl-1-heptene, 4-vinylcyclohexene, vinylcyclohexane, norbornadiene, ethylidene norbornene, cyclopentene, cyclohexene, dicyclopentadiene, cyclooctene, $C_4$-$C_{40}$ dienes, including but not limited to 1,3-butadiene, 1,3-pentadiene, 1,4-hexadiene, 1,5-hexadiene, 1,7-octadiene, 1,9-decadiene, other $C_4$-$C_{40}$ α-olefins, and the like. In certain embodiments, the α-olefin is propylene, 1-butene, 1-pentene, 1-hexene, 1-octene or a combination thereof. Although any hydrocarbon containing a vinyl group potentially may be used in embodiments of the invention, practical issues such as monomer availability, cost, and the ability to conveniently remove unreacted monomer from the resulting polymer may become more problematic as the molecular weight of the monomer becomes too high.

The polymerization processes described herein are well suited for the production of olefin polymers comprising monovinylidene aromatic monomers including styrene, o-methyl styrene, p-methyl styrene, t-butylstyrene, and the like. In particular, interpolymers comprising ethylene and styrene can be prepared by following the teachings herein. Optionally, copolymers comprising ethylene, styrene and a $C_3$-$C_{20}$ alpha olefin, optionally comprising a $C_4$-$C_{20}$ diene, having improved properties can be prepared.

Suitable non-conjugated diene monomers can be a straight chain, branched chain or cyclic hydrocarbon diene having from 6 to 15 carbon atoms. Examples of suitable non-conjugated dienes include, but are not limited to, straight chain acyclic dienes, such as 1,4-hexadiene, 1,6-octadiene, 1,7-octadiene, 1,9-decadiene, branched chain acyclic dienes, such as 5-methyl-1,4-hexadiene; 3,7-dimethyl-1,6-octadiene; 3,7-dimethyl-1,7-octadiene and mixed isomers of dihydromyricene and dihydroocinene, single ring alicyclic dienes, such as 1,3-cyclopentadiene; 1,4-cyclohexadiene; 1,5-cyclooctadiene and 1,5-cyclododecadiene, and multi-ring alicyclic fused and bridged ring dienes, such as tetrahydroindene, methyl tetrahydroindene, dicyclopentadiene, bicyclo-(2,2,1)-hepta-2,5-diene; alkenyl, alkylidene, cycloalkenyl and cycloalkylidene norbornenes, such as 5-methylene-2-norbornene (MNB); 5-propenyl-2-norbornene, 5-isopropylidene-2-norbornene, 5-(4-cyclopentenyl)-2-norbornene, 5-cyclohexylidene-2-norbornene, 5-vinyl-2-norbornene, and norbornadiene. Of the dienes typically used to prepare EPDMs, the particularly preferred dienes are 1,4-hexadiene (HD), 5-ethylidene-2-norbornene (ENB), 5-vinylidene-2-norbornene (VNB), 5-methylene-2-norbornene (MNB), and dicyclopentadiene (DCPD). The especially preferred dienes are 5-ethylidene-2-norbornene (ENB) and 1,4-hexadiene (HD).

One class of desirable polymers that can be made in accordance with embodiments of the invention are elastomeric interpolymers of ethylene, a $C_3$-$C_{20}$ α-olefin, especially propylene, and optionally one or more diene monomers. Preferred α-olefins for use in this embodiment of the present invention are designated by the formula $CH_2=CHR^*$, where R* is a linear or branched alkyl group of from 1 to 12 carbon atoms. Examples of suitable α-olefins include, but are not limited to, propylene, isobutylene, 1-butene, 1-pentene, 1-hexene, 4-methyl-1-pentene, and 1-octene. A particularly preferred α-olefin is propylene. The propylene based polymers are generally referred to in the art as EP or EPDM polymers. Suitable dienes for use in preparing such polymers, especially multi-block EPDM type polymers include conjugated or non-conjugated, straight or branched chain-, cyclic- or polycyclic-dienes comprising from 4 to 20 carbons. Preferred dienes include 1,4-pentadiene, 1,4-hexadiene, 5-ethylidene-2-norbornene, dicyclopentadiene, cyclohexadiene, and 5-butylidene-2-norbornene. A particularly preferred diene is 5-ethylidene-2-norbornene.

Because the diene containing polymers comprise alternating segments or blocks containing greater or lesser quantities of the diene (including none) and α-olefin (including none), the total quantity of diene and α-olefin may be reduced without loss of subsequent polymer properties. That is, because the diene and α-olefin monomers are preferentially incorporated into one type of block of the polymer rather than uniformly or randomly throughout the polymer, they are more efficiently utilized and subsequently the crosslink density of the polymer can be better controlled. Such crosslinkable elastomers and the cured products have advantaged properties, including higher tensile strength and better elastic recovery.

In some embodiments, the inventive interpolymers made with two catalysts incorporating differing quantities of comonomer have a weight ratio of blocks formed thereby from 95:5 to 5:95. The elastomeric polymers desirably have an ethylene content of from 20 to 90 percent, a diene content of from 0.1 to 10 percent, and an α-olefin content of from 10 to 80 percent, based on the total weight of the polymer. Further preferably, the multi-block elastomeric polymers have an ethylene content of from 60 to 90 percent, a diene content of from 0.1 to 10 percent, and an α-olefin content of from 10 to 40 percent, based on the total weight of the polymer. Preferred polymers are high molecular weight polymers, having a weight average molecular weight (Mw) from 10,000 to about 2,500,000, preferably from 20,000 to 500,000, more preferably from 20,000 to 350,000, and a polydispersity less than 3.5, more preferably less than 3.0, and a Mooney viscosity (ML(1+4)125° C.) from 1 to 250. More preferably, such polymers have an ethylene content from 65 to 75 percent, a diene content from 0 to 6 percent, and an α-olefin content from 20 to 35 percent.

The ethylene/α-olefin interpolymers can be functionalized by incorporating at least one functional group in its polymer structure. Exemplary functional groups may include, for example, ethylenically unsaturated mono- and di-functional carboxylic acids, ethylenically unsaturated mono- and di-functional carboxylic acid anhydrides, salts thereof and esters thereof. Such functional groups may be grafted to an ethylene/α-olefin interpolymer, or it may be copolymerized with ethylene and an optional additional comonomer to form an interpolymer of ethylene, the functional comonomer and optionally other comonomer(s). Means for grafting functional groups onto polyethylene are described for example in U.S. Pat. Nos. 4,762,890, 4,927,888, and 4,950,541, the disclosures of these patents are incorporated herein by reference in their entirety. One particularly useful functional group is malic anhydride.

The amount of the functional group present in the functional interpolymer can vary. The functional group can typically be present in a copolymer-type functionalized interpolymer in an amount of at least about 1.0 weight percent, preferably at least about 5 weight percent, and more preferably at least about 7 weight percent. The functional group will typically be present in a copolymer-type functionalized interpolymer in an amount less than about 40 weight percent, preferably less than about 30 weight percent, and more preferably less than about 25 weight percent.

Other Components

The composition can comprise at least another component, in addition to the interpolymer, for the purposes of improving and/or controlling the viscosity, adhesive properties, shelf-life, stability and cost. Non-limiting examples of additional components include tackifiers, plasticizers (plasticizing oils or extender oils), waxes, antioxidants, UV stabilizers, colorants or pigments, fillers, flow aids, coupling agents, crosslinking agents, surfactants, solvents, and combinations thereof. Some components for adhesive compositions have been described in U.S. Pat. Nos. 5,750,623 and 5,143,968, both of which are incorporated herein by reference, all of which can be used in embodiments of the invention with or without modifications.

In some embodiments, the compositions disclosed herein can comprise a tackifier or tackifying resin or tackifier resin. The tackifier may modify the properties of the composition such as viscoelastic properties (e.g., tan delta), rheological properties (e.g., viscosity), tackiness (i.e., ability to stick), pressure sensitivity, and wetting property. In some embodiments, the tackifier is used to improve the tackiness of the composition. In other embodiments, the tackifier is used to reduce the viscosity of the composition. In further embodiments, the tackifier is used to render the composition a pressure-sensitive adhesive. In particular embodiments, the tackifier is used to wet out adherent surfaces and/or improve the adhesion to the adherent surfaces.

Any tackifier known to a person of ordinary skill in the art may be used in the adhesion composition disclosed herein. Tackifiers suitable for the compositions disclosed herein can be solids, semi-solids, or liquids at room temperature. Non-limiting examples of tackifiers include (1) natural and modified rosins (e.g., gum rosin, wood rosin, tall oil rosin, distilled rosin, hydrogenated rosin, dimerized rosin, and polymerized rosin); (2) glycerol and pentaerythritol esters of natural and modified rosins (e.g., the glycerol ester of pale, wood rosin, the glycerol ester of hydrogenated rosin, the glycerol ester of polymerized rosin, the pentaerythritol ester of hydrogenated rosin, and the phenolic-modified pentaerythritol ester of rosin); (3) copolymers and terpolymers of natured terpenes (e.g., styrene/terpene and alpha methyl styrene/terpene); (4) polyterpene resins and hydrogenated polyterpene resins; (5) phenolic modified terpene resins and hydrogenated derivatives thereof (e.g., the resin product resulting from the condensation, in an acidic medium, of a bicyclic terpene and a phenol); (6) aliphatic or cycloaliphatic hydrocarbon resins and the hydrogenated derivatives thereof (e.g., resins resulting from the polymerization of monomers consisting primarily of olefins and diolefins); (7) aromatic hydrocarbon resins and the hydrogenated derivatives thereof; (8) aromatic modified aliphatic or cycloaliphatic hydrocarbon resins and the hydrogenated derivatives thereof; and combinations thereof. The amount of the tackifier in the composition can be from about 5 to about 70 wt %, from about 10 to about 65 wt %, or from about 15 to about 60 wt % of the total weight of the composition.

In other embodiments, the tackifiers include rosin-based tackifiers (e.g. AQUATAC® 9027, AQUATAC® 4188, SYLVALITE®, SYLVATAC® and SYLVAGUM® rosin esters from Arizona Chemical, Jacksonville, Fla.). In other embodiments, the tackifiers include polyterpenes or terpene resins (e.g., SYLVARES® terpene resins from Arizona Chemical, Jacksonville, Fla.). In other embodiments, the tackifiers include aliphatic hydrocarbon resins such as resins resulting from the polymerization of monomers consisting of olefins and diolefins (e.g., ESCOREZ® 1310LC, ESCOREZ® 2596 from ExxonMobil Chemical Company, Houston, Tex.) and the hydrogenated derivatives thereof; alicyclic petroleum hydrocarbon resins and the hydrogenated derivatives thereof (e.g. ESCOREZ® 5300 and 5400 series from ExxonMobil Chemical Company; EASTOTAC® resins from Eastman Chemical, Kingsport, Tenn.). In further embodiments, the tackifiers are modified with tackifier modifiers including aromatic compounds (e.g., ESCOREZ® 2596 from ExxonMobil Chemical Company.) and low softening point resins (e.g., AQUATAC 5527 from Arizona Chemical, Jacksonville, Fla.). In some embodiments, the tackifier is an aliphatic hydrocarbon resin having at least five carbon atoms. In other embodiments, the tackifier has a Ring and Ball (R&B) softening point equal to or greater than 80° C. The Ring and Ball (R&B) softening point can be measured by the method described in ASTM E28, which is incorporated herein by reference.

In some embodiments, the performance characteristics of the tackifier in the composition disclosed herein can be directly related to its compatibility with the ethylene/α-olefin interpolymer. Preferably, the compositions with desirable adhesive properties can be obtained with tackifiers that are compatible with the interpolymer. For example, when a compatible tackifier is added in the correct concentration to the interpolymer, desirable tack properties can be produced. Although incompatible tackifiers may not produce desirable tack properties, they may be used to impact other desirable properties. For example, the properties of the composition can be fine-tuned by the addition of a tackifier having limited compatibility to reduce the tack level and/or increase the cohesive strength characteristics.

In further embodiments, the compositions disclosed herein optionally can comprise a plasticizer or plasticizing oil or an extender oil that may reduce viscosity and/or improve tack properties. Any plasticizer known to a person of ordinary skill in the art may be used in the adhesion composition disclosed herein. Non-limiting examples of plasticizers include olefin oligomers, low molecular weight polyolefins such as liquid polybutene, phthalates, mineral oils such as naphthenic, paraffinic, or hydrogenated (white) oils (e.g. Kaydol oil), vegetable and animal oil and their derivatives, petroleum derived oils, and combinations thereof. In some embodiments, the plasticizers include polypropylene, polybutene, hydrogenated polyisoprene, hydrogenated polybutadiene, polypiperylene and copolymers of piperylene and isoprene, and the like having average molecular weights between about 350 and about 10,000. In other embodiments, the plasticizers include glyceryl esters of the usual fatty acids and polymerization products thereof.

In some embodiments, a suitable insoluble plasticizer may be selected from the group which includes dipropylene glycol dibenzoate, pentaerythritol tetrabenzoate; polyethylene glycol 400-di-2-ethylhexoate; 2-ethylhexyl diphenyl phsophate; butyl benzyl phthalate, dibutyl phthalate, dioctyl phthalate, various substituted citrates, and glycerates. Suitable dipropylene glycol dibenzoate and pentaerythritol tetrabenzoate may be purchased from Velsicol Chemical Company of Chicago, Ill. under the trade designations "Benzoflex 9-88 and S-552", respectively. Further, a suitable polyethylene glycol 400-di-2-ethylhexoate may be purchased from C.P. Hall Company of Chicago, Ill. under the trade designation "Tegmer 809". A suitable 2-ethylhexyl diphenyl phosphate, and a butyl benzyl phthalate may be purchased from Monsanto Industrial Chemical Company of St. Louis, Mo. under the trade designation "Santicizer 141 and 160", respectively. When Benzoflex is used as a plasticizer in an adhesive composition, it can delay the crystallization in diaper core stabilization adhesives, which are used to stabilize the thinner cores of diapers and adult incontinence products.

In further embodiments, the compositions disclosed herein optionally can comprise a wax that may reduce the melt viscosity in addition to reducing costs. Any wax known to a person of ordinary skill in the art can be used in the adhesion composition disclosed herein. Non-limiting examples of suitable waxes include petroleum waxes, polyolefin waxes such as low molecular weight polyethylene or polypropylene, synthetic waxes, paraffin and microcrystalline waxes having melting points from about 55 to about 110° C., Fischer-Tropsch waxes and combinations thereof. In some embodiments, the wax is a low molecular weight polyethylene homopolymer or interpolymer having a number average molecular weight of about 400 to about 6,000 g/mole. In particular, the inventive interpolymer having such an average molecular weight can be used as a wax, in addition to the higher molecular weight inventive polymer being used as a polymeric component. Where used, the amount of the wax in the composition can be from greater than 0 to about 50 wt %, from about 10 to about 45 wt %, or from about 25 to about 40 wt % of the total weight of the composition.

In further embodiments, the compositions disclosed herein optionally can comprise an antioxidant or a stabilizer. Any antioxidant known to a person of ordinary skill in the art may be used in the adhesion composition disclosed herein. Non-limiting examples of suitable antioxidants include amine-based antioxidants such as alkyl diphenylamines, phenyl-α-naphthylamine, alkyl or aralkyl substituted phenyl-α-naphthylamine, alkylated p-phenylene diamines, tetramethyl-diaminodiphenylamine and the like; and hindered phenol compounds such as 2,6-di-t-butyl-4-methylphenol; 1,3,5-trimethyl-2,4,6-tris(3',5'-di-t-butyl-4'-hydroxybenzyl)benzene; tetrakis[(methylene(3,5-di-t-butyl-4-hydroxyhydrocinnamate)]methane (e.g., IRGANOX™ 1010, from Ciba Geigy, New York); octadecyl-3,5-di-t-butyl-4-hydroxycinnamate (e.g., IRGANOX™ 1076, commercially available from Ciba Geigy) and combinations thereof. Where used, the amount of the antioxidant in the composition can be from about greater than 0 to about 1 wt %, from about 0.05 to about 0.75 wt %, or from about 0.1 to about 0.5 wt % of the total weight of the composition.

In further embodiments, the compositions disclosed herein optionally can comprise an UV stabilizer that may prevent or reduce the degradation of the compositions by UV radiation. Any UV stabilizer known to a person of ordinary skill in the art may be used in the adhesion composition disclosed herein. Non-limiting examples of suitable UV stabilizers include benzophenones, benzotriazoles, aryl esters, oxanilides, acrylic esters, Formamidine carbon black, hindered amines, nickel quenchers, hindered amines, phenolic antioxidants, metallic salts, zinc compounds and combinations thereof. Where used, the amount of the UV stabilizer in the composition can be from about greater than 0 to about 1 wt %, from about 0.05 to about 0.75 wt %, or from about 0.1 to about 0.5 wt % of the total weight of the composition.

In further embodiments, the compositions disclosed herein optionally can comprise a colorant or pigment. Any colorant or pigment known to a person of ordinary skill in the art may be used in the adhesion composition disclosed herein. Non-limiting examples of suitable colorants or pigments include inorganic pigments such as titanium dioxide and carbon black, phthalocyanine pigments, and other organic pigments such as IRGAZIN®, CROMOPHTAL®, MONASTRAL®, CINQUASIA®, IRGALITE®, ORASOL®, all of which are available from Ciba Specialty Chemicals, Tarrytown, N.Y. Where used, the amount of the colorant or pigment in the composition can be from about greater than 0 to about 10 wt %, from about 0.1 to about 5 wt %, or from about 0.5 to about 2 wt % of the total weight of the composition.

In further embodiments, the compositions disclosed herein optionally can comprise a filler. Any filler known to a person of ordinary skill in the art may be used in the adhesion composition disclosed herein. Non-limiting examples of suitable fillers include sand, talc, dolomite, calcium carbonate, clay, silica, mica, wollastonite, feldspar, aluminum silicate, alumina, hydrated alumina, glass bead, glass microsphere, ceramic microsphere, thermoplastic microsphere, barite, wood flour, and combinations thereof. Where used, the amount of the filler in the composition can be from about greater than 0 to about 60 wt %, from about 1 to about 50 wt %, or from about 5 to about 40 wt % of the total weight of the composition.

In formulating the composition, it is preferable that each of the additives are compatible with the ethylene/α-olefin interpolymer disclosed herein so that the additives do not phase separate from the ethylene/α-olefin interpolymer, particularly in molten state. In general, the compatibility of an additive with the ethylene/α-olefin interpolymer increases with a decrease in the difference between their solubility parameters such as Hildebrand solubility parameters. Some Hildebrand solubility parameters are tabulated for solvents in: Barton, A. F. M., *Handbook of Solubility and Other Cohesion Parameters,* 2nd Ed. CRC Press, Boca Raton, Fla. (1991); for monomers and representative polymers in *Polymer Handbook,* 3rd Ed., J. Brandrup & E. H. Immergut, Eds. John Wiley, NY, pages 519-557 (1989); and for many commercially available polymers in Barton, A. F. M., *Handbook of Polymer-Liquid Interaction Parameters and Solubility Parameters,* CRC Press, Boca Raton, Fla. (1990), all of which are incorporated herein by reference. The Hildebrand solubility parameter for a copolymer may be calculated using a volume fraction weighting of the individual Hildebrand solubility parameters for each monomer comprising the copolymer, as described for binary copolymers in Barton A. F. M., *Handbook of Solubility Parameters and Other Cohesion Parameters,* CRC Press, Boca Raton, page 12 (1990). The magnitude of the Hildebrand solubility parameter for polymeric materials is also known to be weakly dependent upon the molecular weight of the polymer, as noted in Barton, pages 446-448. Therefore, there will be a preferred molecular weight range for a given ethylene/α-olefin interpolymer, and adhesive strength may be additionally controlled by manipulating the molecular weight of the ethylene/α-olefin interpolymer or the additives such as the tackifier. In some embodiments, the absolute difference in Hildebrand solubility parameter between the ethylene/α-olefin interpolymer and an additive such as the tackifier, plasticizer or oil, and the wax falls within the range of greater than 0 to about 10 $MPa^{1/2}$, about 0.1 to about 5 $MPa^{1/2}$, about 0.5 to about 4.0 $MPa^{1/2}$, or about 1 to about 3.0 $MPa^{1/2}$.

The compatibility of the additives with the ethylene/α-olefin interpolymer can also be determined by cloud point measurement and dynamic mechanical analysis. The cloud point temperature is the temperature at which a component begins to solidify or "cloud up" as it cools from a clear liquid phase to the solid phase. For example, for waxes, the cloud point is usually close to the melting point of the wax. Generally, the lower the cloud point temperature, the greater the compatibility. The cloud point measurement is disclosed in "*Adhesives and Coatings Manual*" by National Distillers and Chemical Corporation (1983), which is incorporated herein by reference.

Dynamic mechanical analysis (DMA) can be another technique to identify compatibility characteristics of the additives with the ethylene/α-olefin interpolymer. When an additive, such as the tackifier having a first glass transition temperature ($T_g$), is compatible with the ethylene/α-olefin interpolymer having a second $T_g$, DMA generally reveals one single glass transition zone but with the second $T_g$ shift to a different temperature due to the contribution of the first $T_g$. This indicates an intimate mix (solubility) between the tackifier and the ethylene/α-olefin interpolymer. In case of incompatibility, DMA can detect a separate phase transition for each of the tackifier and the ethylene/α-olefin interpolymer.

Preparation of Compositions Comprising Ethylene/α-Olefin Interpolymers

In some embodiments, the compositions disclosed herein are adhesive and/or thermoplastic marking compositions comprising an ethylene/α-olefin interpolymer, a tackifier and optional other additives. The blending of the ethylene/α-olefin interpolymer with the additives can be done by any known method that can result in a substantially homogeneous distribution of the components of the adhesive. The ingredients of the compositions can be blended using methods known to a person of ordinary skill in the art. Non-limiting examples of suitable blending methods include melt blending, solvent blending, and the like.

In some embodiments, the ingredients of the compositions are melt blended by a method as described by Guerin et al. in U.S. Pat. No. 4,152,189. That is, all solvent (if used) is removed from the ingredients by heating to an appropriate elevated temperature of about 100° C. to about 200° C. or about 150° C. to about 175° C. at a pressure of about 5 Torr to about 10 Torr. Then, the ingredients are weighed into a vessel in the desired proportions. The blend is then formed by heating the contents of the vessel to about 150° C. to about 175° C. while stirring.

In other embodiments, the ingredients of the compositions are processed using solvent blending. The ingredients in the blend are substantially soluble in the solvents used.

Physical blending devices that provide dispersive mixing, distributive mixing, or a combination of dispersive and distributive mixing can be useful in preparing homogenous blends. Both batch and continuous methods of physical blending can be used. Non-limiting examples of batch methods include those methods using BRABENDER® mixing equipment (e.g., BRABENDER PREP CENTER®, available from C. W. Brabender Instruments, Inc., South Hackensack, N.J.) or BANBURY® internal mixing and roll milling (available from Farrel Company, Ansonia, Conn.) equipment. Non-limiting examples of continuous methods include single screw extruding, twin screw extruding, disk extruding, reciprocating single screw extruding, and pin barrel single screw extruding.

An aqueous dispersion of the ethylene/α-olefin interpolymer may also be used in the formulation of various compositions. U.S. Pat. No. 5,574,091, incorporated by reference herein in its entirety, teaches the preparation of aqueous dispersions of olefin copolymers in the presence of a stabilizing and an emulsifying amount of a suitable surfactant, such as sulfate of an ethoxylated phenol, e.g., poly(oxy-1,2-ethanediyl)α-sulfo-ω(nonylphonoxy)ammonium salt. Such methods can also be used to make aqueous dispersions of the ethylene/α-olefin interpolymer. Additional suitable methods are disclosed in U.S. Pat. No. 5,539,021, which is incorporated by reference herein in its entirety.

Applications of Compositions Comprising Ethylene/α-Olefin Interpolymers

The compositions disclosed herein can be used as hot melt adhesives, pressure sensitive adhesives or as thermoplastic marking compositions. It can be applied to manufacture any article that requires or comprises a hot melt adhesive or a pressure sensitive adhesive. Non-limiting examples of suitable articles include paper products, packaging materials, laminated wood panels, kitchen countertops, vehicles, labels, disposable diapers, hospital pads, feminine sanitary napkins, surgical drapes, tapes, cases, cartons, trays, medical devices, and bandages. In a further embodiment, the adhesive composition can be used in tapes, cases, cartons, trays, medical devices, and bandages.

In some embodiments, the compositions are used as hot melt adhesives. Such hot melt adhesive compositions can be used in industrial applications including packaging, particularly for low temperature use such as for dairy products or for freezer packaging of food products, and in sanitary disposable consumer articles, for example, diapers, feminine care pads, napkins, and the like. Some other suitable applications include book-binding, wood working and labeling.

In other embodiments, the compositions disclosed herein may be used as PSAs. Such PSA adhesive compositions can be applied to sheeting products (e.g., decorative, reflective, and graphical), labelstock, and tape backings. The substrate can be any suitable type of material depending on the desired application. In certain embodiments, the substrate comprises a nonwoven, paper, polymeric film (e.g., polypropylene (e.g., biaxially oriented polypropylene (BOPP)), polyethylene, polyurea, or polyester (e.g., polyethylene terephthalate (PET)), or release liner (e.g., siliconized liner).

In still other embodiments, the compositions can be utilized to form tape. For example, the PSA or hot melt adhesive composition is applied to at least one side of the backing of the tape. The adhesive composition may then be crosslinked to further improve its shear strength. Any suitable crosslinking method (e.g., exposure to radiation, such as ultraviolet or electron beam) or crosslinker additive (e.g., phenolic and silane curatives) may be utilized.

The adhesive compositions disclosed herein may be applied to the desired substrate or adhered in any manner known in the art, particularly those methods used traditionally for making tapes, cases, cartons, trays, medical devices, and bandages. In other embodiments, the adhesive compositions can be applied by a coating head or nozzle, with associated equipment. The adhesive compositions can be applied as fine lines, dots or spray coatings, in addition to other traditional forms as desired.

In some embodiments, the adhesive compositions can be applied using melt extrusion techniques. The adhesive composition can be applied by either continuous or batch processes. An example of a batch process is the placement of a portion of the adhesive composition between a substrate to which the adhesive composition is to be adhered and a surface capable of releasing the adhesive to form a composite structure. An example of a continuous forming method includes drawing the adhesive composition out of a heated film die and subsequently contacting the drawn composition to a moving plastic web or other suitable substrate.

In other embodiments, the adhesive compositions can be coated using a solvent-based method. For example, the solvent-based adhesive composition can be coated by such methods as knife coating, roll coating, gravure coating, rod coating, curtain coating, and air knife coating. The coated solvent-based adhesive composition is then dried to remove the solvent. Preferably, the applied solvent-based adhesive composition is subjected to elevated temperatures, such as those supplied by an oven, to expedite drying.

In some embodiments, the compositions disclosed herein are used as thermoplastic marking compositions for marking roads. The thermoplastic marking compositions can be in the form of a hot melt extrusion road marking, hot melt spray road marking, hot melt hand applied road marking, colored hot melt marked bicycle lane, simulation or training road marking, preformed extruded traffic symbol or tape, flexible and soft sports/playground surface marking, safety marking on a ship, or a reflective traffic safety coating. The general formulations and descriptions of thermoplastic marking compositions have been disclosed in U.S. Pat. No. 6,552,110, which is incorporated herein by reference. In particular embodiments, the thermoplastic marking compositions comprise the ethylene/α-olefin interpolymer disclosed herein, a tackifier, a filler and optionally a pigment. Preferably, the filler is glass beads or glass microspheres.

The filler will be provided to the thermoplastic marking composition in an amount of from 40 to 90 weight percent, preferably from 50 to 90 weight percent. In particularly preferred embodiments, the filler will comprise a combination of the following: 0 to 60 weight percent sand, 0 to 100 percent dolomite or talc, 0 to 50 weight percent glass microspheres, and 1 to 20 weight percent pigment.

When it is desired that the thermoplastic coating composition have reflective attributes, a reflective inorganic filler will be employed. One particularly preferred reflective inorganic filler is glass microspheres. When a reflective inorganic filler is employed, it will typically be provided to the thermoplastic coating composition in an amount of at least 5 weight percent, preferably at least 10 weight percent, and more preferably at least 20 weight percent. The reflective inorganic filler will be provided to the thermoplastic coating composition in an amount of no more than 70, preferably no more than 50 weight percent, and most preferably no more than 40 weight percent.

Certain inorganic fillers will typically be employed in an effort to reduce the cost of the formulation. One suitable extending filler is dolomite clay. When employed, the dolomite filler will be provided in an amount of at least 10 weight percent, more preferably at least 20 weight percent, and most preferably at least 30 weight percent of the thermoplastic coating composition. The dolomite filler will typically be provided in an amount of no more than 80 weight percent, more preferably no more than 75 weight percent, and most preferably no more than 70 weight percent of the thermoplastic coating composition.

The thermoplastic marking compositions are advantageous in that they may be readily designed to be applied by the various techniques used in the industry. For instance, it is now possible to develop a single formulation, which may be usefully applied by extrusion, screed, or spray techniques.

The thermoplastic marking compositions will preferably exhibit an adhesion, as measured in accordance with the techniques set forth in Example Two of U.S. Pat. No. 6,552,110, of at least 1.0 N/mm$^2$, preferably at least 1.2 N/mm$^2$, more preferably at least 1.3 N/mm$^2$, and most preferably at least 1.5 N/mm$^2$. U.S. Pat. No. 6,552,110 is incorporated herein by reference.

The thermoplastic marking compositions will preferably exhibit a luminance factor, as measured in accordance with the techniques set forth in Example Two of U.S. Pat. No. 6,552,110, of at least 70, preferably at least 75, more preferably at least 76, and most preferably at least 78.

The thermoplastic marking compositions further exhibit good low temperature abrasion resistance. The subject formulations exhibit improved low temperature flexibility and low temperature adhesion, and exhibit improved smoke and low odor properties at high temperatures. The subject formulations exhibit a broad potential range of application temperatures, particularly at temperatures of from 150° C. to 250° C., which makes them suitable for application by different means. For instance, the ability of the compositions to be applied at lower application temperatures, that is, temperatures of about 150 to 170° C., makes them suitable for application by extrusion coating techniques; while the ability of the compositions to be applied at higher application temperatures, that is, temperatures of 200° C. to 250° C. makes them suitable for application by spray coating techniques. The subject formulations are preferably resistant to dirt pick-up, and further preferably exhibit less viscosity variability relative to systems which lack the homogeneous ethylene polymer.

The subject formulations are usefully applied via spray, screed, and extrusion techniques. In addition, the subject formulations may be provided as preformed tapes, which are laid upon the surface and bonded to it by heating with, for example, a gas flame, optionally under some applied pressure, as by rolling.

Exemplary applications for the thermoplastic marking compositions are in hot melt extrusion road marking; hot melt spray road marking; hot melt hand applied road markings; colored hot melt marked bicycle lanes applied by spray or extrusion; marking of simulation/training roads for icy surface driving; preformed extruded traffic symbols (such as arrows, letters, etc.) and tapes (such as for traffic safety, information, decoration, etc.) (also called premarks or hot melt tapes); marking of flexible and soft sports/playground surfaces, such as tartan (for instance, in the marking of tennis courts, outdoor and indoor sports floorings, etc.); safety markings on ships, oil rigs, etc.; and reflecting traffic safety coatings for tunnels, concrete, metals with glass beads or other reflecting/self-glowing pigments.

In one preferred application, the subject thermoplastic marking compositions will be employed in embossed road markings. Embossed road markings are formed by extrusion of a marking composition onto a surface; applying reflective particles, such as glass beads, to the extruded marking; and embossing the extruded marking such as to create channels or other ridges. Such embossed markings are desirable, in that they provide enhanced water drainage and improve nighttime reflective properties, particularly in rainy weather. The thermoplastic marking compositions of the invention are advantageous in embossed road marking applications, as they provide the requisite degree of flexibility, adhesion, and abrasion, even under cold temperature conditions.

The following examples are presented to exemplify embodiments of the invention but are not intended to limit the invention to the specific embodiments set forth. Unless indicated to the contrary, all parts and percentages are by weight. All numerical values are approximate. When numerical ranges are given, it should be understood that embodiments outside the stated ranges may still fall within the scope of the invention. Specific details described in each example should not be construed as necessary features of the invention.

Testing Methods

In the examples that follow, the following analytical techniques are employed:

GPC Method for Samples 1-4 and A-C

An automated liquid-handling robot equipped with a heated needle set to 160° C. is used to add enough 1,2,4-trichlorobenzene stabilized with 300 ppm Ionol to each dried polymer sample to give a final concentration of 30 mg/mL. A small glass stir rod is placed into each tube and the samples are heated to 160° C. for 2 hours on a heated, orbital-shaker rotating at 250 rpm. The concentrated polymer solution is then diluted to 1 mg/ml using the automated liquid-handling robot and the heated needle set to 160° C.

A Symyx Rapid GPC system is used to determine the molecular weight data for each sample. A Gilson 350 pump set at 2.0 ml/min flow rate is used to pump helium-purged 1,2-dichlorobenzene stabilized with 300 ppm Ionol as the mobile phase through three Plgel 10 micrometer (μm) Mixed B 300 mm×7.5 mm columns placed in series and heated to 160° C. A Polymer Labs ELS 1000 Detector is used with the Evaporator set to 250° C., the Nebulizer set to 165° C., and the nitrogen flow rate set to 1.8 SLM at a pressure of 60-80 psi (400-600 kPa) $N_2$. The polymer samples are heated to 160° C. and each sample injected into a 250 µl loop using the liquid-handling robot and a heated needle. Serial analysis of the polymer samples using two switched loops and overlapping injections are used. The sample data is collected and analyzed using Symyx Epoch™ software. Peaks are manually integrated and the molecular weight information reported uncorrected against a polystyrene standard calibration curve.

Standard CRYSTAF Method

Branching distributions are determined by crystallization analysis fractionation (CRYSTAF) using a CRYSTAF 200 unit commercially available from PolymerChar, Valencia, Spain. The samples are dissolved in 1,2,4 trichlorobenzene at 160° C. (0.66 mg/mL) for 1 hr and stabilized at 95° C. for 45 minutes. The sampling temperatures range from 95 to 30° C. at a cooling rate of 0.2° C./min. An infrared detector is used to measure the polymer solution concentrations. The cumulative soluble concentration is measured as the polymer crystallizes while the temperature is decreased. The analytical derivative of the cumulative profile reflects the short chain branching distribution of the polymer.

The CRYSTAF peak temperature and area are identified by the peak analysis module included in the CRYSTAF Software (Version 2001.b, PolymerChar, Valencia, Spain). The CRYSTAF peak finding routine identifies a peak temperature as, a maximum in the dW/dT curve and the area between the largest positive inflections on either side of the identified peak in the derivative curve. To calculate the CRYSTAF curve, the preferred processing parameters are with a temperature limit of 70° C. and with smoothing parameters above the temperature limit of 0.1, and below the temperature limit of 0.3.

DSC Standard Method (Excluding Samples 1-4 and A-C)

Differential Scanning Calorimetry results are determined using a TAI model Q1000 DSC equipped with an RCS cooling accessory and an autosampler. A nitrogen purge gas flow of 50 ml/min is used. The sample is pressed into a thin film and melted in the press at about 175° C. and then air-cooled to room temperature (25° C.). 3-10 mg of material is then cut into a 6 mm diameter disk, accurately weighed, placed in a light aluminum pan (ca 50 mg), and then crimped shut. The thermal behavior of the sample is investigated with the following temperature profile. The sample is rapidly heated to 180° C. and held isothermal for 3 minutes in order to remove any previous thermal history. The sample is then cooled to −40° C. at 10° C./min cooling rate and held at −40° C. for 3 minutes. The sample is then heated to 150° C. at 10° C./min. heating rate. The cooling and second heating curves are recorded.

The DSC melting peak is measured as the maximum in heat flow rate (W/g) with respect to the linear baseline drawn between −30° C. and end of melting. The heat of fusion is measured as the area under the melting curve between −30° C. and the end of melting using a linear baseline.

GPC Method (Excluding Samples 1-4 and A-C)

The gel permeation chromatographic system consists of either a Polymer Laboratories Model PL-210 or a Polymer Laboratories Model PL-220 instrument. The column and carousel compartments are operated at 140° C. Three Polymer Laboratories 10-micron Mixed-B columns are used. The solvent is 1,2,4 trichlorobenzene. The samples are prepared at a concentration of 0.1 grams of polymer in 50 milliliters of solvent containing 200 ppm of butylated hydroxytoluene (BHT). Samples are prepared by agitating lightly for 2 hours at 160° C. The injection volume used is 100 microliters and the flow rate is 1.0 ml/minute.

Calibration of the GPC column set is performed with 21 narrow molecular weight distribution polystyrene standards with molecular weights ranging from 580 to 8,400,000, arranged in 6 "cocktail" mixtures with at least a decade of separation between individual molecular weights. The standards are purchased from Polymer Laboratories (Shropshire, UK). The polystyrene standards are prepared at 0.025 grams in 50 milliliters of solvent for molecular weights equal to or greater than 1,000,000, and 0.05 grams in 50 milliliters of solvent for molecular weights less than 1,000,000. The polystyrene standards are dissolved at 80° C. with gentle agitation for 30 minutes. The narrow standards mixtures are run first and in order of decreasing highest molecular weight component to minimize degradation. The polystyrene standard peak molecular weights are converted to polyethylene molecular weights using the following equation (as described in Williams and Ward, *J. Polym. Sci., Polym. Let.*, 6, 621 (1968)):

$$M_{polyethylene} = 0.431(M_{polystyrene}).$$

Polyethylene equivalent molecular weight calculations are performed using Viscotek TriSEC software Version 3.0.

Compression Set

Compression set is measured according to ASTM D 395. The sample is prepared by stacking 25.4 mm diameter round discs of 3.2 mm, 2.0 mm, and 0.25 mm thickness until a total thickness of 12.7 mm is reached. The discs are cut from 12.7 cm×12.7 cm compression molded plaques molded with a hot press under the following conditions: zero pressure for 3 min at 190° C., followed by 86 MPa for 2 min at 190° C., followed by cooling inside the press with cold running water at 86 MPa.

Density

Samples for density measurement are prepared according to ASTM D 1928. Measurements are made within one hour of sample pressing using ASTM D792, Method B.

Flexural/Secant Modulus/Storage Modulus

Samples are compression molded using ASTM D 1928. Flexural and 2 percent secant moduli are measured according to ASTM D-790. Storage modulus is measured according to ASTM D 5026-01 or equivalent technique.

Optical Properties

Films of 0.4 mm thickness are compression molded using a hot press (Carver Model #4095-4PR1001R). The pellets are placed between polytetrafluoroethylene sheets, heated at 190° C. at 55 psi (380 kPa) for 3 min, followed by 1.3 MPa for 3 min, and then 2.6 MPa for 3 min. The film is then cooled in the press with running cold water at 1.3 MPa for 1 min. The compression molded films are used for optical measurements, tensile behavior, recovery, and stress relaxation.

Clarity is measured using BYK Gardner Haze-gard as specified in ASTM D 1746.

45° gloss is measured using BYK Gardner Glossmeter Microgloss 45° as specified in ASTM D-2457

Internal haze is measured using BYK Gardner Haze-gard based on ASTM D 1003 Procedure A. Mineral oil is applied to the film surface to remove surface scratches.

Mechanical Properties—Tensile, Hysteresis, and Tear

Stress-strain behavior in uniaxial tension is measured using ASTM D 1708 microtensile specimens. Samples are stretched with an Instron at 500% $min^{-1}$ at 21° C. Tensile strength and elongation at break are reported from an average of 5 specimens.

100% and 300% Hysteresis is determined from cyclic loading to 100% and 300% strains using ASTM D 1708 microtensile specimens with an Instron™ instrument. The sample is loaded and unloaded at 267% min$^{-1}$ for 3 cycles at 21° C. Cyclic experiments at 300% and 80° C. are conducted using an environmental chamber. In the 80° C. experiment, the sample is allowed to equilibrate for 45 minutes at the test temperature before testing. In the 21° C., 300% strain cyclic experiment, the retractive stress at 150% strain from the first unloading cycle is recorded. Percent recovery for all experiments are calculated from the first unloading cycle using the strain at which the load returned to the base line. The percent recovery is defined as:

$$\% \text{ Recovery} = \frac{\varepsilon_f - \varepsilon_s}{\varepsilon_f} \times 100$$

where $\varepsilon_f$ is the strain taken for cyclic loading and $\varepsilon_s$ is the strain where the load returns to the baseline during the 1$^{st}$ unloading cycle.

Stress relaxation is measured at 50 percent strain and 37° C. for 12 hours using an Instron™ instrument equipped with an environmental chamber. The gauge geometry was 76 mm×25 mm×0.4 mm. After equilibrating at 37° C. for 45 min in the environmental chamber, the sample was stretched to 50% strain at 333% min$^{-1}$. Stress was recorded as a function of time for 12 hours. The percent stress relaxation after 12 hours was calculated using the formula:

$$\% \text{ Stress Relaxation} = \frac{L_0 - L_{12}}{L_0} \times 100$$

where $L_0$ is the load at 50% strain at 0 time and $L_{12}$ is the load at 50 percent strain after 12 hours.

Tensile notched tear experiments are carried out on samples having a density of 0.88 g/cc or less using an Instron™ instrument. The geometry consists of a gauge section of 76 mm×13 mm×0.4 mm with a 2 mm notch cut into the sample at half the specimen length. The sample is stretched at 508 mm min$^{-1}$ at 21° C. until it breaks. The tear energy is calculated as the area under the stress-elongation curve up to strain at maximum load. An average of at least 3 specimens are reported.

TMA

Thermal Mechanical Analysis (Penetration Temperature) is conducted on 30 mm diameter×3.3 mm thick, compression molded discs, formed at 180° C. and 10 MPa molding pressure for 5 minutes and then air quenched. The instrument used is a TMA 7 brand available from Perkin-Elmer. In the test, a probe with 1.5 mm radius tip (P/N N519-0416) is applied to the surface of the sample disc with 1 N force. The temperature is raised at 5° C./min from 25° C. The probe penetration distance is measured as a function of temperature. The experiment ends when the probe has penetrated 1 mm into the sample.

DMA

Dynamic Mechanical Analysis (DMA) is measured on compression molded disks formed in a hot press at 180° C. at 10 MPa pressure for 5 minutes and then water cooled in the press at 90° C./min. Testing is conducted using an ARES controlled strain rheometer (TA instruments) equipped with dual cantilever fixtures for torsion testing.

A 1.5 mm plaque is pressed and cut in a bar of dimensions 32×12 mm. The sample is clamped at both ends between fixtures separated by 10 mm (grip separation ΔL) and subjected to successive temperature steps from −100° C. to 200° C. (5° C. per step). At each temperature the torsion modulus G' is measured at an angular frequency of 10 rad/s, the strain amplitude being maintained between 0.1 percent and 4 percent to ensure that the torque is sufficient and that the measurement remains in the linear regime.

An initial static force of 10 g is maintained (auto-tension mode) to prevent slack in the sample when thermal expansion occurs. As a consequence, the grip separation ΔL increases with the temperature, particularly above the melting or softening point of the polymer sample. The test stops at the maximum temperature or when the gap between the fixtures reaches 65 mm.

Melt Index

Melt index, or $I_2$, is measured in accordance with ASTM D 1238, Condition 190° C./2.16 kg. Melt index, or $I_{10}$ is also measured in accordance with ASTM D 1238, Condition 190° C./10 kg.

ATREF

Analytical temperature rising elution fractionation (ATREF) analysis is conducted according to the method described in U.S. Pat. No. 4,798,081 and Wilde, L.; Ryle, T. R.; Knobeloch, D. C.; Peat, I. R.; *Determination of Branching Distributions in Polyethylene and Ethylene Copolymers*, J. Polym. Sci., 20, 441-455 (1982), which are incorporated by reference herein in their entirety. The composition to be analyzed is dissolved in trichlorobenzene and allowed to crystallize in a column containing an inert support (stainless steel shot) by slowly reducing the temperature to 20° C. at a cooling rate of 0.1° C./min. The column is equipped with an infrared detector. An ATREF chromatogram curve is then generated by eluting the crystallized polymer sample from the column by slowly increasing the temperature of the eluting solvent (trichlorobenzene) from 20 to 120° C. at a rate of 1.5° C./min.

$^{13}$C NMR Analysis

The samples are prepared by adding approximately 3 g of a 50/50 mixture of tetrachloroethane-d2/orthodichlorobenzene to 0.4 g sample in a 10 mm NMR tube. The samples are dissolved and homogenized by heating the tube and its contents to 150° C. The data are collected using a JEOL Eclipse™ 400 MHz spectrometer or a Varian Unity Plus™ 400 MHz spectrometer, corresponding to a 13C resonance frequency of 100.5 MHz. The data are acquired using 4000 transients per data file with a 6 second pulse repetition delay. To achieve minimum signal-to-noise for quantitative analysis, multiple data files are added together. The spectral width is 25,000 Hz with a minimum file size of 32K data points. The samples are analyzed at 130° C. in a 10 mm broad band probe. The comonomer incorporation is determined using Randall's triad method (Randall, J. C.; JMS-Rev. Macromol. Chem. Phys., C29, 201-317 (1989), which is incorporated by reference herein in its entirety.

Polymer Fractionation by TREF

Large-scale TREF fractionation is carried by dissolving 15-20 g of polymer in 2 liters of 1,2,4-trichlorobenzene (TCB) by stirring for 4 hours at 160° C. The polymer solution is forced by 15 psig (100 kPa) nitrogen onto a 3 inch by 4 foot (7.6 cm×12 cm) steel column packed with a 60:40 (v:v) mix of 30-40 mesh (600-425 μm) spherical, technical quality glass beads (available from Potters Industries, HC 30 Box 20, Brownwood, Tex., 76801) and stainless steel, 0.028" (0.7 mm) diameter cut wire shot (available from Pellets, Inc., 63 Industrial Drive, North Tonawanda, N.Y., 14120). The column is immersed in a thermally controlled oil jacket, set initially to 160° C. The column is first cooled ballistically to 125° C., then slow cooled to 20° C. at 0.04° C. per minute and held for one hour. Fresh TCB is introduced at about 65 ml/min while the temperature is increased at 0.167° C. per minute.

Approximately 2000 ml portions of eluant from the preparative TREF column are collected in a 16 station, heated fraction collector. The polymer is concentrated in each fraction using a rotary evaporator until about 50 to 100 ml of the polymer solution remains. The concentrated solutions are allowed to stand overnight before adding excess methanol, filtering, and rinsing (approx. 300-500 ml of methanol including the final rinse). The filtration step is performed on a 3 position vacuum assisted filtering station using 5.0 μm polytetrafluoroethylene coated filter paper (available from Osmonics Inc., Cat#Z50WP04750). The filtrated fractions are dried overnight in a vacuum oven at 60° C. and weighed on an analytical balance before further testing.

Melt Strength

Melt Strength (MS) is measured by using a capillary rheometer fitted with a 2.1 mm diameter, 20:1 die with an entrance angle of approximately 45 degrees. After equilibrating the samples at 190° C. for 10 minutes, the piston is run at a speed of 1 inch/minute (2.54 cm/minute). The standard test temperature is 190° C. The sample is drawn uniaxially to a set of accelerating nips located 100 mm below the die with an acceleration of 2.4 mm/sec$^2$. The required tensile force is recorded as a function of the take-up speed of the nip rolls. The maximum tensile force attained during the test is defined as the melt strength. In the case of polymer melt exhibiting draw resonance, the tensile force before the onset of draw resonance was taken as melt strength. The melt strength is recorded in centiNewtons ("cN").

Catalysts

The term "overnight", if used, refers to a time of approximately 16-18 hours, the term "room temperature", refers to a temperature of 20-25° C., and the term "mixed alkanes" refers to a commercially obtained mixture of $C_{6-9}$ aliphatic hydrocarbons available under the trade designation Isopar E®, from ExxonMobil Chemical Company. In the event the name of a compound herein does not conform to the structural representation thereof, the structural representation shall control. The synthesis of all metal complexes and the preparation of all screening experiments were carried out in a dry nitrogen atmosphere using dry box techniques. All solvents used were HPLC grade and were dried before their use.

MMAO refers to modified methylalumoxane, a triisobutylaluminum modified methylalumoxane available commercially from Akzo-Noble Corporation.

The preparation of catalyst (B1) is conducted as follows.

a) Preparation of (1-methylethyl)(2-hydroxy-3,5-di (t-butyl)phenyl)methylimine 3,5-Di-t-butylsalicylaldehyde (3.00 g) is added to 10 mL of isopropylamine. The solution rapidly turns bright yellow. After stirring at ambient temperature for 3 hours, volatiles are removed under vacuum to yield a bright yellow, crystalline solid (97 percent yield).

b) Preparation of 1,2-bis-(3,5-di-t-butylphenylene) (1-(N-(1-methylethyl)immino)methyl)(2-oxoyl)zirconium dibenzyl A solution of (1-methylethyl)(2-hydroxy-3,5-di(t-butyl) phenyl)imine (605 mg, 2.2 mmol) in 5 mL toluene is slowly added to a solution of $Zr(CH_2Ph)_4$ (500 mg, 1.1 mmol) in 50 mL toluene. The resulting dark yellow solution is stirred for 30 min. Solvent is removed under reduced pressure to yield the desired product as a reddish-brown solid.

The preparation of catalyst (B2) is conducted as follows.

a) Preparation of (1-(2-methylcyclohexyl)ethyl)(2-oxoyl-3,5-di(t-butyl)phenyl)imine 2-Methylcyclohexylamine (8.44 mL, 64.0 mmol) is dissolved in methanol (90 mL), and di-t-butylsalicaldehyde (10.00 g, 42.67 mmol) is added. The reaction mixture is stirred for three hours and then cooled to −25° C. for 12 hrs. The resulting yellow solid precipitate is collected by filtration and washed with cold methanol (2×15 mL), and then dried under reduced pressure. The yield is 11.17 g of a yellow solid. $^1$H NMR is consistent with the desired product as a mixture of isomers.

b) Preparation of bis-(1-(2-methylcyclohexyl)ethyl) (2-oxoyl-3,5-di(t-butyl)phenyl)immino)zirconium dibenzyl A solution of (1-(2-methylcyclohexyl)ethyl)(2-oxoyl-3,5-di(t-butyl)phenyl)imine (7.63 g, 23.2 mmol) in 200 mL toluene is slowly added to a solution of $Zr(CH_2Ph)_4$ (5.28 g, 11.6 mmol) in 600 mL toluene. The resulting dark yellow solution is stirred for 1 hour at 25° C. The solution is diluted further with 680 mL toluene to give a solution having a concentration of 0.00783 M.

Cocatalyst 1 A mixture of methyldi($C_{14-18}$ alkyl)ammonium salts of tetrakis(pentafluorophenyl)borate (here-in-after armeenium borate), prepared by reaction of a long chain trialkylamine (Armeen™ M2HT, available from Akzo-Nobel, Inc.), HCl and $Li[B(C_6F_5)_4]$, substantially as disclosed in U.S. Pat. No. 5,919,9883, Ex. 2.

Cocatalyst 2 Mixed $C_{14-18}$ alkyldimethylammonium salt of bis(tris(pentafluorophenyl)-alumane)-2-undecylimidazolide, prepared according to U.S. Pat. No. 6,395,671, Ex. 16.

Shuttling Agents The shuttling agents employed include diethylzinc (DEZ, SA1), di(i-butyl)zinc (SA2), di(n-hexyl) zinc (SA3), triethylaluminum (TEA, SA4), trioctylaluminum (SA5), triethylgallium (SA6), i-butylaluminum bis(dimethyl (t-butyl)siloxane) (SA7), i-butylaluminum bis(di(trimethylsilyl)amide) (SA8), n-octylaluminum di(pyridine-2-methoxide) (SA9), bis(n-octadecyl)i-butylaluminum (SA10), i-butylaluminum bis(di(n-pentyl)amide) (SA11), n-octylaluminum bis(2,6-di-t-butylphenoxide) (SA12), n-octylaluminum di(ethyl(1-naphthyl)amide) (SA13), ethylaluminum bis (t-butyldimethylsiloxide)(SA14), ethylaluminum di(bis (trimethylsilyl)amide) (SA15), ethylaluminum bis(2,3,6,7-dibenzo-1-azacycloheptaneamide) (SA16), n-octylaluminum bis(2,3,6,7-dibenzo-1-azacycloheptaneamide) (SA17), n-octylaluminum bis(dimethyl(t-butyl)siloxide(SA18), ethylzinc (2,6-diphenylphenoxide) (SA19), and ethylzinc (t-butoxide) (SA20).

EXAMPLES 1-4

Comparative Examples A*-C*

General High Throughput Parallel Polymerization Conditions

Polymerizations are conducted using a high throughput, parallel polymerization reactor (PPR) available from Symyx technologies, Inc. and operated substantially according to U.S. Pat. Nos. 6,248,540, 6,030,917, 6,362,309, 6,306,658, and 6,316,663. Ethylene copolymerizations are conducted at 130° C. and 200 psi (1.4 MPa) with ethylene on demand using 1.2 equivalents of cocatalyst 1 based on total catalyst used (1.1 equivalents when MMAO is present). A series of polymerizations are conducted in a parallel pressure reactor (PPR) contained of 48 individual reactor cells in a 6×8 array that are fitted with a pre-weighed glass tube. The working volume in each reactor cell is 6000 µL. Each cell is temperature and pressure controlled with stirring provided by individual stirring paddles. The monomer gas and quench gas are plumbed directly into the PPR unit and controlled by automatic valves. Liquid reagents are robotically added to each reactor cell by syringes and the reservoir solvent is mixed alkanes. The order of addition is mixed alkanes solvent (4 ml), ethylene, 1-octene comonomer (1 ml), cocatalyst 1 or cocatalyst 1/MMAO mixture, shuttling agent, and catalyst or catalyst mixture. When a mixture of cocatalyst 1 and MMAO or a mixture of two catalysts is used, the reagents are premixed in a small vial immediately prior to addition to the reactor. When a reagent is omitted in an experiment, the above order of addition is otherwise maintained. Polymerizations are conducted for approximately 1-2 minutes, until predetermined ethylene consumptions are reached. After quenching with CO, the reactors are cooled and the glass tubes are unloaded. The tubes are transferred to a centrifuge/vacuum drying unit, and dried for 12 hours at 60° C. The tubes containing dried polymer are weighed and the difference between this weight and the tare weight gives the net yield of polymer. Results are contained in Table 1. In Table 1 and elsewhere in the application, comparative compounds are indicated by an asterisk (*).

Examples 1-4 demonstrate the synthesis of linear block copolymers by the present invention as evidenced by the formation of a very narrow MWD, essentially monomodal copolymer when DEZ is present and a bimodal, broad molecular weight distribution product (a mixture of separately produced polymers) in the absence of DEZ. Due to the fact that Catalyst (A1) is known to incorporate more octene than Catalyst (B1), the different blocks or segments of the resulting copolymers of the invention are distinguishable based on branching or density.

Further characterizing data for the polymers of Table 1 are determined by reference to the figures. More specifically DSC and ATREF results show the following:

The DSC curve for the polymer of example 1 shows a 115.7° C. melting point (Tm) with a heat of fusion of 158.1 J/g. The corresponding CRYSTAF curve shows the tallest peak at 34.5° C. with a peak area of 52.9 percent. The difference between the DSC Tm and the Tcrystaf is 81.2° C.

The DSC curve for the polymer of example 2 shows a peak with a 109.7° C. melting point (Tm) with a heat of fusion of 214.0 J/g. The corresponding CRYSTAF curve shows the tallest peak at 46.2° C. with a peak area of 57.0 percent. The difference between the DSC Tm and the Tcrystaf is 63.5° C.

The DSC curve for the polymer of example 3 shows a peak with a 120.7° C. melting point (Tm) with a heat of fusion of 160.1 J/g. The corresponding CRYSTAF curve shows the tallest peak at 66.1° C. with a peak area of 71.8 percent. The difference between the DSC Tm and the Tcrystaf is 54.6° C.

The DSC curve for the polymer of example 4 shows a peak with a 104.5° C. melting point (Tm) with a heat of fusion of 170.7 J/g. The corresponding CRYSTAF curve shows the tallest peak at 30° C. with a peak area of 18.2 percent. The difference between the DSC Tm and the Tcrystaf is 74.5° C.

The DSC curve for Comparative Example A* shows a 90.0° C. melting point (Tm) with a heat of fusion of 86.7 J/g. The corresponding CRYSTAF curve shows the tallest peak at 48.5° C. with a peak area of 29.4 percent. Both of these values are consistent with a resin that is low in density. The difference between the DSC Tm and the Tcrystaf is 41.8° C.

The DSC curve for Comparative Example B* shows a 129.8° C. melting point (Tm) with a heat of fusion of 237.0 J/g. The corresponding CRYSTAF curve shows the tallest peak at 82.4° C. with a peak area of 83.7 percent. Both of these values are consistent with a resin that is high in density. The difference between the DSC Tm and the Tcrystaf is 47.4° C.

The DSC curve for Comparative Example C* shows a 125.3° C. melting point (Tm) with a heat of fusion of 143.0 J/g. The corresponding CRYSTAF curve shows the tallest peak at 81.8° C. with a peak area of 34.7 percent as well as a lower crystalline peak at 52.4° C. The separation between the two peaks is consistent with the presence of a high crystalline and a low crystalline polymer. The difference between the DSC Tm and the Tcrystaf is 43.5° C.

TABLE 1

| Ex. | Cat. (A1) (µmol) | Cat (B1) (µmol) | Cocat (µmol) | MMAO (µmol) | shuttling agent (µmol) | Yield (g) | Mn | Mw/Mn | hexyls[1] |
|---|---|---|---|---|---|---|---|---|---|
| A* | 0.06 | — | 0.066 | 0.3 | — | 0.1363 | 300502 | 3.32 | — |
| B* | — | 0.1 | 0.110 | 0.5 | — | 0.1581 | 36957 | 1.22 | 2.5 |
| C* | 0.06 | 0.1 | 0.176 | 0.8 | — | 0.2038 | 45526 | 5.30[2] | 5.5 |
| 1 | 0.06 | 0.1 | 0.192 | — | DEZ (8.0) | 0.1974 | 28715 | 1.19 | 4.8 |
| 2 | 0.06 | 0.1 | 0.192 | — | DEZ (80.0) | 0.1468 | 2161 | 1.12 | 14.4 |
| 3 | 0.06 | 0.1 | 0.192 | — | TEA (8.0) | 0.208 | 22675 | 1.71 | 4.6 |
| 4 | 0.06 | 0.1 | 0.192 | — | TEA (80.0) | 0.1879 | 3338 | 1.54 | 9.4 |

[1]$C_6$ or higher chain content per 1000 carbons
[2]Bimodal molecular weight distribution

EXAMPLES 5-19

Comparatives D-F

Continuous Solution Polymerization, Catalyst A1/B2+DEZ

Continuous solution polymerizations are carried out in a computer controlled autoclave reactor equipped with an internal stirrer. Purified mixed alkanes solvent (Isopar™ E available from ExxonMobil Chemical Company), ethylene at 2.70 lbs/hour (1.22 kg/hour), 1-octene, and hydrogen (where used) are supplied to a 3.8 L reactor equipped with a jacket for temperature control and an internal thermocouple. The solvent feed to the reactor is measured by a mass-flow controller. A variable speed diaphragm pump controls the solvent flow rate and pressure to the reactor. At the discharge of the pump, a side stream is taken to provide flush flows for the catalyst and cocatalyst 1 injection lines and the reactor agitator. These flows are measured by Micro-Motion mass flow meters and controlled by control valves or by the manual adjustment of needle valves. The remaining solvent is combined with 1-octene, ethylene, and hydrogen (where used) and fed to the reactor. A mass flow controller is used to deliver hydrogen to the reactor as needed. The temperature of the solvent/monomer solution is controlled by use of a heat exchanger before entering the reactor. This stream enters the bottom of the reactor. The catalyst component solutions are metered using pumps and mass flow meters and are combined with the catalyst flush solvent and introduced into the bottom of the reactor. The reactor is run liquid-full at 500 psig (3.45 MPa) with vigorous stirring. Product is removed through exit lines at the top of the reactor. All exit lines from the reactor are steam traced and insulated. Polymerization is stopped by the addition of a small amount of water into the exit line along with any stabilizers or other additives and passing the mixture through a static mixer. The product stream is then heated by passing through a heat exchanger before devolatilization. The polymer product is recovered by extrusion using a devolatilizing extruder and water cooled pelletizer. Process details and results are contained in Table 2. Selected polymer properties are provided in Table 3.

TABLE 2

Process details for preparation of exemplary polymers

| Ex. | $C_8H_{16}$ kg/hr | Solv. kg/hr | $H_2$ sccm[1] | T °C. | Cat A1[2] ppm | Cat A1 Flow kg/hr | Cat B2[3] ppm | B2 Flow kg/hr | DEZ Conc % | DEZ Flow kg/hr | Cocat Conc. ppm | Cocat Flow kg/hr | $[C_2H_4]/[DEZ]$[4] | Poly Rate[5] kg/hr | Conv %[6] | Solids % | Eff.[7] |
|---|---|---|---|---|---|---|---|---|---|---|---|---|---|---|---|---|---|
| D* | 1.63 | 12.7 | 29.90 | 120 | 142.2 | 0.14 | — | — | 0.19 | 0.32 | 820 | 0.17 | 536 | 1.81 | 88.8 | 11.2 | 95.2 |
| E* | " | 9.5 | 5.00 | " | — | — | 109 | 0.10 | 0.19 | " | 1743 | 0.40 | 485 | 1.47 | 89.9 | 11.3 | 126.8 |
| F* | " | 11.3 | 251.6 | " | 71.7 | 0.06 | 30.8 | 0.06 | — | — | " | 0.11 | — | 1.55 | 88.5 | 10.3 | 257.7 |
| 5 | " | " | — | " | " | 0.14 | 30.8 | 0.13 | 0.17 | 0.43 | " | 0.26 | 419 | 1.64 | 89.6 | 11.1 | 118.3 |
| 6 | " | " | 4.92 | " | " | 0.10 | 30.4 | 0.08 | 0.17 | 0.32 | " | 0.18 | 570 | 1.65 | 89.3 | 11.1 | 172.7 |
| 7 | " | " | 21.70 | " | " | 0.07 | 30.8 | 0.06 | 0.17 | 0.25 | " | 0.13 | 718 | 1.60 | 89.2 | 10.6 | 244.1 |
| 8 | " | " | 36.90 | " | " | 0.06 | " | " | " | 0.10 | " | 0.12 | 1778 | 1.62 | 90.0 | 10.8 | 261.1 |
| 9 | " | " | 78.43 | " | " | " | " | " | " | 0.04 | " | " | 4596 | 1.63 | 90.2 | 10.8 | 267.9 |
| 10 | " | " | 0.00 | 123 | 71.1 | 0.12 | 30.3 | 0.14 | 0.34 | 0.19 | 1743 | 0.08 | 415 | 1.67 | 90.31 | 11.1 | 131.1 |
| 11 | " | " | " | 120 | 71.1 | 0.16 | " | 0.17 | 0.80 | 0.15 | 1743 | 0.10 | 249 | 1.68 | 89.56 | 11.1 | 100.6 |
| 12 | " | " | " | 121 | 71.1 | 0.15 | " | 0.07 | " | 0.09 | 1743 | 0.07 | 396 | 1.70 | 90.02 | 11.3 | 137.0 |
| 13 | " | " | " | 122 | 71.1 | 0.12 | " | 0.06 | " | 0.05 | 1743 | 0.05 | 653 | 1.69 | 89.64 | 11.2 | 161.9 |
| 14 | " | " | " | 120 | 71.1 | 0.05 | " | 0.29 | " | 0.10 | 1743 | 0.10 | 395 | 1.41 | 89.42 | 9.3 | 114.1 |
| 15 | 2.45 | " | " | " | 71.1 | 0.14 | " | 0.17 | " | 0.14 | 1743 | 0.09 | 282 | 1.80 | 89.33 | 11.3 | 121.3 |
| 16 | " | " | " | 122 | 71.1 | 0.10 | " | 0.13 | " | 0.07 | 1743 | 0.07 | 485 | 1.78 | 90.11 | 11.2 | 159.7 |
| 17 | " | " | " | 121 | 71.1 | 0.10 | " | 0.14 | " | 0.08 | 1743 | " | 506 | 1.75 | 89.08 | 11.0 | 155.6 |
| 18 | 0.69 | " | " | 121 | 71.1 | " | " | 0.22 | " | 0.11 | 1743 | 0.10 | 331 | 1.25 | 89.93 | 8.8 | 90.2 |
| 19 | 0.32 | " | " | 122 | 71.1 | 0.06 | " | " | " | 0.09 | 1743 | 0.08 | 367 | 1.16 | 90.74 | 8.4 | 106.0 |

*Comparative, not an example of the invention
[1]standard cm³/min
[2][N-(2,6-di(1-methylethyl)phenyl)amido)(2-isopropylphenyl)(α-naphthalen-2-diyl(6-pyridin-2-diyl)methane)]hafnium dimethyl
[3]bis-(1-(2-methylcyclohexyl)ethyl)(2-oxoyl-3,5-di(t-butyl)phenyl)immino) zirconium dibenzyl
[4]molar ratio in reactor
[5]polymer production rate
[6]percent ethylene conversion in reactor
[7]efficiency, kg polymer/g M where g M = g Hf + g Zr

TABLE 3

Properties of exemplary polymers

| Ex. | Density (g/cm³) | $I_2$ | $I_{10}$ | $I_{10}/I_2$ | Mw (g/mol) | Mn (g/mol) | Mw/Mn | Heat of Fusion (J/g) | $T_m$ (° C.) | $T_c$ (° C.) | $T_{CRYSTAF}$ (° C.) | Tm − $T_{CRYSTAF}$ (° C.) | CRYSTAF Peak Area (percent) |
|---|---|---|---|---|---|---|---|---|---|---|---|---|---|
| D* | 0.8627 | 1.5 | 10.0 | 6.5 | 110,000 | 55,800 | 2.0 | 32 | 37 | 45 | 30 | 7 | 99 |
| E* | 0.9378 | 7.0 | 39.0 | 5.6 | 65,000 | 33,300 | 2.0 | 183 | 124 | 113 | 79 | 45 | 95 |
| F* | 0.8895 | 0.9 | 12.5 | 13.4 | 137,300 | 9,980 | 13.8 | 90 | 125 | 111 | 78 | 47 | 20 |
| 5 | 0.8786 | 1.5 | 9.8 | 6.7 | 104,600 | 53,200 | 2.0 | 55 | 120 | 101 | 48 | 72 | 60 |
| 6 | 0.8785 | 1.1 | 7.5 | 6.5 | 109600 | 53300 | 2.1 | 55 | 115 | 94 | 44 | 71 | 63 |
| 7 | 0.8825 | 1.0 | 7.2 | 7.1 | 118,500 | 53,100 | 2.2 | 69 | 121 | 103 | 49 | 72 | 29 |

TABLE 3-continued

Properties of exemplary polymers

| Ex. | Density (g/cm³) | $I_2$ | $I_{10}$ | $I_{10}/I_2$ | Mw (g/mol) | Mn (g/mol) | Mw/Mn | Heat of Fusion (J/g) | $T_m$ (° C.) | $T_c$ (° C.) | $T_{CRYSTAF}$ (° C.) | $T_m - T_{CRYSTAF}$ (° C.) | CRYSTAF Peak Area (percent) |
|---|---|---|---|---|---|---|---|---|---|---|---|---|---|
| 8  | 0.8828 | 0.9 | 6.8  | 7.7 | 129,000 | 40,100 | 3.2 | 68  | 124 | 106 | 80 | 43 | 13 |
| 9  | 0.8836 | 1.1 | 9.7  | 9.1 | 129600  | 28700  | 4.5 | 74  | 125 | 109 | 81 | 44 | 16 |
| 10 | 0.8784 | 1.2 | 7.5  | 6.5 | 113,100 | 58,200 | 1.9 | 54  | 116 | 92  | 41 | 75 | 52 |
| 11 | 0.8818 | 9.1 | 59.2 | 6.5 | 66,200  | 36,500 | 1.8 | 63  | 114 | 93  | 40 | 74 | 25 |
| 12 | 0.8700 | 2.1 | 13.2 | 6.4 | 101,500 | 55,100 | 1.8 | 40  | 113 | 80  | 30 | 83 | 91 |
| 13 | 0.8718 | 0.7 | 4.4  | 6.5 | 132,100 | 63,600 | 2.1 | 42  | 114 | 80  | 30 | 81 | 8  |
| 14 | 0.9116 | 2.6 | 15.6 | 6.0 | 81,900  | 43,600 | 1.9 | 123 | 121 | 106 | 73 | 48 | 92 |
| 15 | 0.8719 | 6.0 | 41.6 | 6.9 | 79,900  | 40,100 | 2.0 | 33  | 114 | 91  | 32 | 82 | 10 |
| 16 | 0.8758 | 0.5 | 3.4  | 7.1 | 148,500 | 74,900 | 2.0 | 43  | 117 | 96  | 48 | 69 | 65 |
| 17 | 0.8757 | 1.7 | 11.3 | 6.8 | 107,500 | 54,000 | 2.0 | 43  | 116 | 96  | 43 | 73 | 57 |
| 18 | 0.9192 | 4.1 | 24.9 | 6.1 | 72,000  | 37,900 | 1.9 | 136 | 120 | 106 | 70 | 50 | 94 |
| 19 | 0.9344 | 3.4 | 20.3 | 6.0 | 76,800  | 39,400 | 1.9 | 169 | 125 | 112 | 80 | 45 | 88 |

The resulting polymers are tested by DSC and ATREF as with previous examples. Results are as follows:

The DSC curve for the polymer of example 5 shows a peak with a 119.6° C. melting point (Tm) with a heat of fusion of 60.0 J/g. The corresponding CRYSTAF curve shows the tallest peak at 47.6° C. with a peak area of 59.5 percent. The delta between the DSC Tm and the Tcrystaf is 72.0° C.

The DSC curve for the polymer of example 6 shows a peak with a 115.2° C. melting point (Tm) with a heat of fusion of 60.4 J/g. The corresponding CRYSTAF curve shows the tallest peak at 44.2° C. with a peak area of 62.7 percent. The delta between the DSC Tm and the Tcrystaf is 71.0° C.

The DSC curve for the polymer of example 7 shows a peak with a 121.3° C. melting point with a heat of fusion of 69.1 J/g. The corresponding CRYSTAF curve shows the tallest peak at 49.2° C. with a peak area of 29.4 percent. The delta between the DSC Tm and the Tcrystaf is 72.1° C.

The DSC curve for the polymer of example 8 shows a peak with a 123.5° C. melting point (Tm) with a heat of fusion of 67.9 J/g. The corresponding CRYSTAF curve shows the tallest peak at 80.1° C. with a peak area of 12.7 percent. The delta between the DSC Tm and the Tcrystaf is 43.4° C.

The DSC curve for the polymer of example 9 shows a peak with a 124.6° C. melting point (Tm) with a heat of fusion of 73.5 J/g. The corresponding CRYSTAF curve shows the tallest peak at 80.8° C. with a peak area of 16.0 percent. The delta between the DSC Tm and the Tcrystaf is 43.8° C.

The DSC curve for the polymer of example 10 shows a peak with a 115.6° C. melting point (Tm) with a heat of fusion of 60.7 J/g. The corresponding CRYSTAF curve shows the tallest peak at 40.9° C. with a peak area of 52.4 percent. The delta between the DSC Tm and the Tcrystaf is 74.7° C.

The DSC curve for the polymer of example 11 shows a peak with a 113.6° C. melting point (Tm) with a heat of fusion of 70.4 J/g. The corresponding CRYSTAF curve shows the tallest peak at 39.6° C. with a peak area of 25.2 percent. The delta between the DSC Tm and the Tcrystaf is 74.1° C.

The DSC curve for the polymer of example 12 shows a peak with a 113.2° C. melting point (Tm) with a heat of fusion of 48.9 J/g. The corresponding CRYSTAF curve shows no peak equal to or above 30° C. (Tcrystaf for purposes of further calculation is therefore set at 30° C.). The delta between the DSC Tm and the Tcrystaf is 83.2° C.

The DSC curve for the polymer of example 13 shows a peak with a 114.4° C. melting point (Tm) with a heat of fusion of 49.4 J/g. The corresponding CRYSTAF curve shows the tallest peak at 33.8° C. with a peak area of 7.7 percent. The delta between the DSC Tm and the Tcrystaf is 84.4° C.

The DSC for the polymer of example 14 shows a peak with a 120.8° C. melting point (Tm) with a heat of fusion of 127.9 J/g. The corresponding CRYSTAF curve shows the tallest peak at 72.9° C. with a peak area of 92.2 percent. The delta between the DSC Tm and the Tcrystaf is 47.9° C.

The DSC curve for the polymer of example 15 shows a peak with a 114.3° C. melting point (Tm) with a heat of fusion of 36.2 J/g. The corresponding CRYSTAF curve shows the tallest peak at 32.3° C. with a peak area of 9.8 percent. The delta between the DSC Tm and the Tcrystaf is 82.0° C.

The DSC curve for the polymer of example 16 shows a peak with a 116.6° C. melting point (Tm) with a heat of fusion of 44.9 J/g. The corresponding CRYSTAF curve shows the tallest peak at 48.0° C. with a peak area of 65.0 percent. The delta between the DSC Tm and the Tcrystaf is 68.6° C.

The DSC curve for the polymer of example 17 shows a peak with a 116.0° C. melting point (Tm) with a heat of fusion of 47.0 J/g. The corresponding CRYSTAF curve shows the tallest peak at 43.1° C. with a peak area of 56.8 percent. The delta between the DSC Tm and the Tcrystaf is 72.9° C.

The DSC curve for the polymer of example 18 shows a peak with a 120.5° C. melting point (Tm) with a heat of fusion of 141.8 J/g. The corresponding CRYSTAF curve shows the tallest peak at 70.0° C. with a peak area of 94.0 percent. The delta between the DSC Tm and the Tcrystaf is 50.5° C.

The DSC curve for the polymer of example 19 shows a peak with a 124.8° C. melting point (Tm) with a heat of fusion of 174.8 J/g. The corresponding CRYSTAF curve shows the tallest peak at 79.9° C. with a peak area of 87.9 percent. The delta between the DSC Tm and the Tcrystaf is 45.0° C.

The DSC curve for the polymer of Comparative Example D* shows a peak with a 37.3° C. melting point (Tm) with a heat of fusion of 31.6 J/g. The corresponding CRYSTAF curve shows no peak equal to and above 30° C. Both of these values are consistent with a resin that is low in density. The delta between the DSC Tm and the Tcrystaf is 7.3° C.

The DSC curve for the polymer of Comparative Example E* shows a peak with a 124.0° C. melting point (Tm) with a heat of fusion of 179.3 J/g. The corresponding CRYSTAF curve shows the tallest peak at 79.3° C. with a peak area of 94.6 percent. Both of these values are consistent with a resin that is high in density. The delta between the DSC Tm and the Tcrystaf is 44.6° C.

The DSC curve for the polymer of Comparative Example F* shows a peak with a 124.8° C. melting point (Tm) with a heat of fusion of 90.4 J/g. The corresponding CRYSTAF curve shows the tallest peak at 77.6° C. with a peak area of 19.5 percent. The separation between the two peaks is consistent with the presence of both a high crystalline and a low crystalline polymer. The delta between the DSC Tm and the Tcrystaf is 47.2° C.

Physical Property Testing

Polymer samples are evaluated for physical properties such as high temperature resistance properties, as evidenced by TMA temperature testing, pellet blocking strength, high temperature recovery, high temperature compression set and storage modulus ratio, G'(25° C.)/G'(100° C.). Several commercially available polymers are included in the tests: Comparative Example G* is a substantially linear ethylene/1-octene copolymer (AFFINITY®, available from The Dow Chemical Company), Comparative Example H* is an elastomeric, substantially linear ethylene/1-octene copolymer (AFFINITY®EG8100, available from The Dow Chemical Company), Comparative Example I* is a substantially linear ethylene/1-octene copolymer (AFFINITY®PL1840, available from The Dow Chemical Company), Comparative Example J* is a hydrogenated styrene/butadiene/styrene triblock copolymer (KRATON™ G1652, available from KRATON Polymers), Comparative Example K* is a thermoplastic vulcanizate (TPV, a polyolefin blend containing dispersed therein a crosslinked elastomer). Results are presented in Table 4.

mm TMA temperature of about 107° C., but it has very poor (high temperature 70° C.) compression set of about 100 percent and it also failed to recover (sample broke) during a high temperature (80° C.) 300 percent strain recovery. Thus the exemplified polymers have a unique combination of properties unavailable even in some commercially available, high performance thermoplastic elastomers.

Similarly, Table 4 shows a low (good) storage modulus ratio, G'(25° C.)/G'(100° C.), for the inventive polymers of 6 or less, whereas a physical blend (Comparative Example F*) has a storage modulus ratio of 9 and a random ethylene/octene copolymer (Comparative Example G*) of similar density has a storage modulus ratio an order of magnitude greater (89). It is desirable that the storage modulus ratio of a polymer be as close to 1 as possible. Such polymers will be relatively unaffected by temperature, and fabricated articles made from such polymers can be usefully employed over a broad temperature range. This feature of low storage modulus ratio and temperature independence is particularly useful in elastomer applications such as in pressure sensitive adhesive formulations.

The data in Table 4 also demonstrate that the polymers of the invention possess improved pellet blocking strength. In particular, Example 5 has a pellet blocking strength of 0 MPa, meaning it is free flowing under the conditions tested, compared to Comparatives F and G which show considerable blocking. Blocking strength is important since bulk shipment of polymers having large blocking strengths can result in

TABLE 4

High Temperature Mechanical Properties

| Ex. | TMA-1 mm penetration (° C.) | Pellet Blocking Strength lb/ft² (kPa) | G'(25° C.)/ G'(100° C.) | 300% Strain Recovery (80° C.) (percent) | Compression Set (70° C.) (percent) |
|---|---|---|---|---|---|
| D* | 51 | — | 9 | Failed | — |
| E* | 130 | — | 18 | — | — |
| F* | 70 | 141 (6.8) | 9 | Failed | 100 |
| 5 | 104 | 0 (0) | 6 | 81 | 49 |
| 6 | 110 | — | 5 | — | 52 |
| 7 | 113 | — | 4 | 84 | 43 |
| 8 | 111 | — | 4 | Failed | 41 |
| 9 | 97 | — | 4 | — | 66 |
| 10 | 108 | — | 5 | 81 | 55 |
| 11 | 100 | — | 8 | — | 68 |
| 12 | 88 | — | 8 | — | 79 |
| 13 | 95 | — | 6 | 84 | 71 |
| 14 | 125 | — | 7 | — | — |
| 15 | 96 | — | 5 | — | 58 |
| 16 | 113 | — | 4 | — | 42 |
| 17 | 108 | 0 (0) | 4 | 82 | 47 |
| 18 | 125 | — | 10 | — | — |
| 19 | 133 | — | 9 | — | — |
| G* | 75 | 463 (22.2) | 89 | Failed | 100 |
| H* | 70 | 213 (10.2) | 29 | Failed | 100 |
| I* | 111 | — | 11 | — | — |
| J* | 107 | — | 5 | Failed | 100 |
| K* | 152 | — | 3 | — | 40 |

In Table 4, Comparative Example F* (which is a physical blend of the two polymers resulting from simultaneous polymerizations using catalyst A1 and B1) has a 1 mm penetration temperature of about 70° C., while Examples 5-9 have a 1 mm penetration temperature of 100° C. or greater. Further, examples 10-19 all have a 1 mm penetration temperature of greater than 85° C., with most having 1 mm TMA temperature of greater than 90° C. or even greater than 100° C. This shows that the novel polymers have better dimensional stability at higher temperatures compared to a physical blend. Comparative Example J* (a commercial SEBS) has a good 1 product clumping or sticking together upon storage or shipping, resulting in poor handling properties.

High temperature (70° C.) compression set for the inventive polymers is generally good, meaning generally less than about 80 percent, preferably less than about 70 percent and especially less than about 60 percent. In contrast, Comparatives F, G, H and J all have a 70° C. compression set of 100 percent (the maximum possible value, indicating no recovery). Good high temperature compression set (low numerical values) is especially needed for applications such as gaskets, window profiles, o-rings, and the like.

TABLE 5

Ambient Temperature Mechanical Properties

| Ex. | Flex Modulus (MPa) | Tensile Modulus (MPa) | Tensile Strength (MPa)[1] | Elongation at Break[1] (%) | Tensile Strength (MPa) | Elongation at Break (%) | Abrasion: Volume Loss (mm³) | Tensile Notched Tear Strength (mJ) | 100% Strain Recovery 21° C. (percent) | 300% Strain Recovery 21° C. (percent) | Retractive Stress at 150% Strain (kPa) | Compression Set 21° C. (Percent) | Stress Relaxation at 50% Strain[2] |
|---|---|---|---|---|---|---|---|---|---|---|---|---|---|
| D* | 12 | 5 | — | — | 10 | 1074 | — | — | 91 | 83 | 760 | — | — |
| E* | 895 | 589 | — | — | 31 | 1029 | — | — | — | — | — | — | — |
| F* | 57 | 46 | — | — | 12 | 824 | 93 | 339 | 78 | 65 | 400 | 42 | — |
| 5 | 30 | 24 | 14 | 951 | 16 | 1116 | 48 | — | 87 | 74 | 790 | 14 | 33 |
| 6 | 33 | 29 | — | — | 14 | 938 | — | — | — | 75 | 861 | 13 | — |
| 7 | 44 | 37 | 15 | 846 | 14 | 854 | 39 | — | 82 | 73 | 810 | 20 | — |
| 8 | 41 | 35 | 13 | 785 | 14 | 810 | 45 | 461 | 82 | 74 | 760 | 22 | — |
| 9 | 43 | 38 | — | — | 12 | 823 | — | — | — | — | — | 25 | — |
| 10 | 23 | 23 | — | — | 14 | 902 | — | — | 86 | 75 | 860 | 12 | — |
| 11 | 30 | 26 | — | — | 16 | 1090 | — | 976 | 89 | 66 | 510 | 14 | 30 |
| 12 | 20 | 17 | 12 | 961 | 13 | 931 | — | 1247 | 91 | 75 | 700 | 17 | — |
| 13 | 16 | 14 | — | — | 13 | 814 | — | 691 | 91 | — | — | 21 | — |
| 14 | 212 | 160 | — | — | 29 | 857 | — | — | — | — | — | — | — |
| 15 | 18 | 14 | 12 | 1127 | 10 | 1573 | — | 2074 | 89 | 83 | 770 | 14 | — |
| 16 | 23 | 20 | — | — | 12 | 968 | — | — | 88 | 83 | 1040 | 13 | — |
| 17 | 20 | 18 | — | — | 13 | 1252 | — | 1274 | 13 | 83 | 920 | 4 | — |
| 18 | 323 | 239 | — | — | 30 | 808 | — | — | — | — | — | — | — |
| 19 | 706 | 483 | — | — | 36 | 871 | — | — | — | — | — | — | — |
| G* | 15 | 15 | — | — | 17 | 1000 | — | 746 | 86 | 53 | 110 | 27 | 50 |
| H* | 16 | 15 | — | — | 15 | 829 | — | 569 | 87 | 60 | 380 | 23 | — |
| I* | 210 | 147 | — | — | 29 | 697 | — | — | — | — | — | — | — |
| J* | — | — | — | — | 32 | 609 | — | — | 93 | 96 | 1900 | 25 | — |
| K* | — | — | — | — | — | — | — | — | — | — | — | 30 | — |

[1] Tested at 51 cm/minute
[2] measured at 38° C. for 12 hours

Table 5 shows results for mechanical properties for the new polymers as well as for various comparison polymers at ambient temperatures. It may be seen that the inventive polymers have very good abrasion resistance when tested according to ISO 4649, generally showing a volume loss of less than about 90 mm³, preferably less than about 80 mm³, and especially less than about 50 mm³. In this test, higher numbers indicate higher volume loss and consequently lower abrasion resistance.

Tear strength as measured by tensile notched tear strength of the inventive polymers is generally 1000 mJ or higher, as shown in Table 5. Tear strength for the inventive polymers can be as high as 3000 mJ, or even as high as 5000 mJ. Comparative polymers generally have tear strengths no higher than 750 mJ.

Table 5 also shows that the polymers of the invention have better retractive stress at 150 percent strain (demonstrated by higher retractive stress values) than some of the comparative samples. Comparative Examples F*, G* and H* have retractive stress value at 150 percent strain of 400 kPa or less, while the inventive polymers have retractive stress values at 150 percent strain of 500 kPa (Ex. 11) to as high as about 1100 kPa (Ex. 17). Polymers having higher than 150 percent retractive stress values would be quite useful for elastic applications, such as elastic fibers and fabrics, especially nonwoven fabrics. Other applications include diaper, hygiene, and medical garment waistband applications, such as tabs and elastic bands.

Table 5 also shows that stress relaxation (at 50 percent strain) is also improved (less) for the inventive polymers as compared to, for example, Comparative Example G*. Lower stress relaxation means that the polymer retains its force better in applications such as diapers and other garments where retention of elastic properties over long time periods at body temperatures is desired.

Optical Testing

TABLE 6

Polymer Optical Properties

| Ex. | Internal Haze (percent) | Clarity (percent) | 45° Gloss (percent) |
|---|---|---|---|
| F* | 84 | 22 | 49 |
| G* | 5 | 73 | 56 |
| 5 | 13 | 72 | 60 |
| 6 | 33 | 69 | 53 |
| 7 | 28 | 57 | 59 |
| 8 | 20 | 65 | 62 |
| 9 | 61 | 38 | 49 |
| 10 | 15 | 73 | 67 |
| 11 | 13 | 69 | 67 |
| 12 | 8 | 75 | 72 |
| 13 | 7 | 74 | 69 |
| 14 | 59 | 15 | 62 |
| 15 | 11 | 74 | 66 |
| 16 | 39 | 70 | 65 |
| 17 | 29 | 73 | 66 |
| 18 | 61 | 22 | 60 |
| 19 | 74 | 11 | 52 |
| G* | 5 | 73 | 56 |
| H* | 12 | 76 | 59 |
| I* | 20 | 75 | 59 |

The optical properties reported in Table 6 are based on compression molded films substantially lacking in orientation. Optical properties of the polymers may be varied over wide ranges, due to variation in crystallite size, resulting from variation in the quantity of chain shuttling agent employed in the polymerization.

Extractions of Multi-Block Copolymers

Extraction studies of the polymers of examples 5, 7 and Comparative Example E* are conducted. In the experiments, the polymer sample is weighed into a glass fritted extraction thimble and fitted into a Kumagawa type extractor. The extractor with sample is purged with nitrogen, and a 500 mL round bottom flask is charged with 350 mL of diethyl ether. The flask is then fitted to the extractor. The ether is heated while being stirred. Time is noted when the ether begins to condense into the thimble, and the extraction is allowed to proceed under nitrogen for 24 hours. At this time, heating is stopped and the solution is allowed to cool. Any ether remaining in the extractor is returned to the flask. The ether in the flask is evaporated under vacuum at ambient temperature, and the resulting solids are purged dry with nitrogen. Any residue is transferred to a weighed bottle using successive washes of hexane. The combined hexane washes are then evaporated with another nitrogen purge, and the residue dried under vacuum overnight at 40° C. Any remaining ether in the extractor is purged dry with nitrogen.

A second clean round bottom flask charged with 350 mL of hexane is then connected to the extractor. The hexane is heated to reflux with stirring and maintained at reflux for 24 hours after hexane is first noticed condensing into the thimble. Heating is then stopped and the flask is allowed to cool. Any hexane remaining in the extractor is transferred back to the flask. The hexane is removed by evaporation under vacuum at ambient temperature, and any residue remaining in the flask is transferred to a weighed bottle using successive hexane washes. The hexane in the flask is evaporated by a nitrogen purge, and the residue is vacuum dried overnight at 40° C.

The polymer sample remaining in the thimble after the extractions is transferred from the thimble to a weighed bottle and vacuum dried overnight at 40° C. Results are contained in Table 7.

TABLE 7

| Sample | wt. (g) | ether soluble (g) | ether soluble (percent) | $C_8$ mole percent[1] | hexane soluble (g) | hexane soluble (percent) | $C_8$ mole percent[1] | residue $C_8$ mole percent[1] |
|---|---|---|---|---|---|---|---|---|
| Comp. F* | 1.097 | 0.063 | 5.69 | 12.2 | 0.245 | 22.35 | 13.6 | 6.5 |
| Ex. 5 | 1.006 | 0.041 | 4.08 | — | 0.040 | 3.98 | 14.2 | 11.6 |
| Ex. 7 | 1.092 | 0.017 | 1.59 | 13.3 | 0.012 | 1.10 | 11.7 | 9.9 |

[1]Determined by $^{13}C$ NMR

Additional Polymer Examples 19 A-F

Continuous Solution Polymerization, Catalyst A1/B2+DEZ

Continuous solution polymerizations are carried out in a computer controlled well-mixed reactor. Purified mixed alkanes solvent (Isopar™ E available from ExxonMobil Chemical Company), ethylene, 1-octene, and hydrogen (where used) are combined and fed to a 27 gallon reactor. The feeds to the reactor are measured by mass-flow controllers. The temperature of the feed stream is controlled by use of a glycol cooled heat exchanger before entering the reactor. The catalyst component solutions are metered using pumps and mass flow meters. The reactor is run liquid-full at approximately 550 psig pressure. Upon exiting the reactor, water and additive are injected in the polymer solution. The water hydrolyzes the catalysts, and terminates the polymerization reactions. The post reactor solution is then heated in preparation for a two-stage devolatization. The solvent and unreacted monomers are removed during the devolatization process. The polymer melt is pumped to a die for underwater pellet cutting.

Process details and results are contained in Table 7a. Selected polymer properties are provided in Tables 7b-7c.

TABLE 7a

| | | | | | | | | | | | | |
|---|---|---|---|---|---|---|---|---|---|---|---|---|
| | | | | | Polymerization Conditions | | | | | | | |
| Ex. | $C_2H_4$ lb/hr | $C_8H_{16}$ lb/hr | Solv. lb/hr | $H_2$ sccm[1] | T °C. | Cat A1[2] Conc. ppm | Cat A1 Flow lb/hr | Cat B2[3] Conc. ppm | Cat B2 Flow lb/hr | DEZ Conc wt % | DEZ Flow lb/hr |
| 19a | 55.29 | 32.03 | 323.03 | 101 | 120 | 600 | 0.25 | 200 | 0.42 | 3.0 | 0.70 |
| 19b | 53.95 | 28.96 | 325.3 | 577 | 120 | 600 | 0.25 | 200 | 0.55 | 3.0 | 0.24 |
| 19c | 55.53 | 30.97 | 324.37 | 550 | 120 | 600 | 0.216 | 200 | 0.609 | 3.0 | 0.69 |
| 19d | 54.83 | 30.58 | 326.33 | 60 | 120 | 600 | 0.22 | 200 | 0.63 | 3.0 | 1.39 |
| 19e | 54.95 | 31.73 | 326.75 | 251 | 120 | 600 | 0.21 | 200 | 0.61 | 3.0 | 1.04 |
| 19f | 50.43 | 34.80 | 330.33 | 124 | 120 | 600 | 0.20 | 200 | 0.60 | 3.0 | 0.74 |

TABLE 7a-continued

| | | | Polymerization Conditions | | | | | | | | |
|---|---|---|---|---|---|---|---|---|---|---|---|
| 19g | 50.25 | 33.08 | 325.61 | 188 | 120 | 600 | 0.19 | 200 | 0.59 | 3.0 | 0.54 |
| 19h | 50.15 | 34.87 | 318.17 | 58 | 120 | 600 | 0.21 | 200 | 0.66 | 3.0 | 0.70 |
| 19i | 55.02 | 34.02 | 323.59 | 53 | 120 | 600 | 0.44 | 200 | 0.74 | 3.0 | 1.72 |
| 19j | 7.46 | 9.04 | 50.6 | 47 | 120 | 150 | 0.22 | 76.7 | 0.36 | 0.5 | 0.19 |

| Ex. | Cocat 1 Conc. ppm | Cocat 1 Flow lb/hr | Cocat 2 Conc. ppm | Cocat 2 Flow lb/hr | $[Zn]^4$ in polymer ppm | Poly Rate[5] lb/hr | Conv[6] wt % | Polymer wt % | Eff.[7] |
|---|---|---|---|---|---|---|---|---|---|
| 19a | 4500 | 0.65 | 525 | 0.33 | 248 | 83.94 | 88.0 | 17.28 | 297 |
| 19b | 4500 | 0.63 | 525 | 0.11 | 90 | 80.72 | 88.1 | 17.2 | 295 |
| 19c | 4500 | 0.61 | 525 | 0.33 | 246 | 84.13 | 88.9 | 17.16 | 293 |
| 19d | 4500 | 0.66 | 525 | 0.66 | 491 | 82.56 | 88.1 | 17.07 | 280 |
| 19e | 4500 | 0.64 | 525 | 0.49 | 368 | 84.11 | 88.4 | 17.43 | 288 |
| 19f | 4500 | 0.52 | 525 | 0.35 | 257 | 85.31 | 87.5 | 17.09 | 319 |
| 19g | 4500 | 0.51 | 525 | 0.16 | 194 | 83.72 | 87.5 | 17.34 | 333 |
| 19h | 4500 | 0.52 | 525 | 0.70 | 259 | 83.21 | 88.0 | 17.46 | 312 |
| 19i | 4500 | 0.70 | 525 | 1.65 | 600 | 86.63 | 88.0 | 17.6 | 275 |
| 19j | — | — | — | — | — | — | — | — | — |

[1]standard cm³/min
[2][N-(2,6-di(1-methylethyl)phenyl)amido)(2-isopropylphenyl)(α-naphthalen-2-diyl(6-pyridin-2-diyl)methane)]hafnium dimethyl
[3]bis-(1-(2-methylcyclohexyl)ethyl)(2-oxoyl-3,5-di(t-butyl)phenyl)immino) zirconium dimethyl
[4]ppm in final product calculated by mass balance
[5]polymer production rate
[6]weight percent ethylene conversion in reactor
[7]efficiency, kg polymer/g M where g M = g Hf + g Z TABLE 7b

| | | | | | | | Polymer Physical properties | | | | | |
|---|---|---|---|---|---|---|---|---|---|---|---|---|
| Polymer Ex. No. | Density (g/cc) | $I_2$ | $I_{10}$ | $I_{10}/I_2$ | Mw (g/mol) | Mn (g/mol) | Mw/Mn | Heat of Fusion (J/g) | Tm (° C.) | Tc (° C.) | TCRYSTAF (° C.) | Tm − TCRYSTAF (° C.) | CRYSTAF Peak Area (wt %) |
| 19g | 0.8649 | 0.9 | 6.4 | 7.1 | 135000 | 64800 | 2.1 | 26 | 120 | 92 | 30 | 90 | 90 |
| 19h | 0.8654 | 1.0 | 7.0 | 7.1 | 131600 | 66900 | 2.0 | 26 | 118 | 88 | — | — | — |

TABLE 7c

Average Block Index For exemplary polymers[1]

| Example | $Zn/C_2{}^2$ | Average BI |
|---|---|---|
| Polymer F | 0 | 0 |
| Polymer 8 | 0.56 | 0.59 |
| Polymer 19a | 1.3 | 0.62 |
| Polymer 5 | 2.4 | 0.52 |
| Polymer 19b | 0.56 | 0.54 |
| Polymer 19h | 3.15 | 0.59 |

[1]Additional information regarding the calculation of the block indices for various polymers is disclosed in U.S. patent application Ser. No. ____ (insert when known), entitled "Ethylene/α-Olefin Block Interpolymers", filed on Mar. 15, 2006, in the name of Colin L. P. Shan, Lonnie Hazlitt, et. al. and assigned to Dow Global Technologies Inc., the disclose of which is incorporated by reference herein in its entirety.
[2]Zn/$C_2$ * 1000 = (Zn feed flow * Zn concentration/1000000/Mw of Zn)/(Total Ethylene feed flow * (1 − fractional ethylene conversion rate)/Mw of Ethylene) * 1000.
Please note that "Zn" in "Zn/$C_2$ * 1000" refers to the amount of zinc in diethyl zinc ("DEZ") used in the polymerization process, and "C2" refers to the amount of ethylene used in the polymerization process.

EXAMPLES 20-22

Ethylene/α-Olefin Interpolymers

Continuous solution polymerizations were carried out in a computer controlled well-mixed reactor. Purified mixed alkanes solvent (ISOPAR™ E available from ExxonMobil Chemical Company), ethylene, 1-octene, and hydrogen (where used) were combined and fed to a 102 L reactor. The feeds to the reactor were measured by mass-flow controllers. The temperature of the feed stream was controlled by use of a glycol cooled heat exchanger before entering the reactor. The catalyst component solutions were metered using pumps and mass flow meters. The reactor was run liquid-full at approximately 550 psig pressure. Upon exiting the reactor, water and additive were injected in the polymer solution. The water hydrolyzed the catalysts, and terminated the polymerization reactions. The post reactor solution was then heated in preparation for a two-stage devolatilization. The solvent and unreacted monomers were removed during the devolatilization process. The polymer melt was pumped to a die for underwater pellet cutting. Process details and results are contained in Table 8.

EXAMPLES 23-26

Ethylene/α-Olefin Interpolymers

Continuous solution polymerizations were carried out in a computer controlled well-mixed reactor equipped with an internal stirrer. Purified mixed alkanes solvent (ISOPAR™ E available from ExxonMobil Chemical Company), ethylene, 1-octene, and hydrogen (where used) were supplied to a 5.0 L reactor equipped with a jacket for temperature control and an internal thermocouple. The solvent fed to the reactor was measured by a mass-flow controller. A variable speed diaphragm pump controlled the solvent flow rate and pressure to the reactor. At the discharge of the pump, a side stream was taken to provide flush flows for the catalyst and cocatalyst 1 injection lines and the reactor agitator. These flows were measured by Micro-Motion mass flow meters and controlled by control valves or by the manual adjustment of needle valves. The remaining solvent was combined with 1-octene, ethylene, and hydrogen (where used) and fed to the reactor. A mass flow controller was used to deliver hydrogen to the reactor as needed. The temperature of the solvent/monomer solution was controlled by using a heat exchanger before entering the reactor. This stream entered the bottom of the reactor. The catalyst component solutions were metered using pumps and mass flow meters and were combined with the catalyst flush solvent and introduced into the bottom of the reactor. The reactor was run liquid-full at 406 psig (2.8 MPa) with vigorous stirring. Product was removed through exit lines at the top of the reactor. All exit lines from the reactor were steam traced and insulated. Polymerization was stopped by the addition of a small amount of water into the exit line along with any stabilizers or other additives and passing the mixture through a static mixer. The product stream was then heated up through heat exchangers, and passed through two devolatizers in series before it was water cooled. Process details and results are contained in Table 8.

Testing of Examples 20-26

Standard CRYSTAF Method. Branching distributions were determined by crystallization analysis fractionation (CRYSTAF) using a CRYSTAF 200 unit commercially available from PolymerChar, Valencia, Spain. The samples were dissolved in 1,2,4-trichlorobenzene at 160° C. (0.66 mg/mL) for 1 hour and stabilized at 95° C. for 45 minutes. The sampling temperatures ranged from 95 to 30° C. at a cooling rate of 0.2° C./min. An infrared detector was used to measure the polymer solution concentrations. The cumulative soluble concentration was measured as the polymer crystallized while the temperature was decreased. The analytical derivative of the cumulative profile reflected the short chain branching distribution of the polymer.

The CRYSTAF peak temperature and area were identified by the peak analysis module included in the CRYSTAF Software (Version 2001.b, PolymerChar, Valencia, Spain). The CRYSTAF peak finding routine identified a peak temperature as a maximum in the dW/dT curve and the area between the largest positive inflections on either side of the identified peak in the derivative curve. To calculate the CRYSTAF curve, the preferred processing parameters were with a temperature limit of 70° C. and with smoothing parameters above the temperature limit of 0.1, and below the temperature limit of 0.3. The CRYSTAF peak temperature and the peak area of each example are listed in Table 9 below.

DSC Standard Method for Polymers. Differential Scanning Calorimetry results were determined using a TAI model Q1000 DSC equipped with an RCS cooling accessory and an autosampler. A nitrogen purge gas flow of 50 ml/min was used. The sample was pressed into a thin film and melted in the press at about 175° C. and then air-cooled to room temperature (25° C.). The sample (~3-10 mg) was then cut into a 6 mm diameter disk, accurately weighed, placed in a light aluminum pan (~50 mg), and then crimped shut. The thermal behavior of the sample was investigated with the following temperature profile. The sample was rapidly heated to 180° C. and held isothermal for 3 minutes in order to remove any previous thermal history. The sample was then cooled to −40° C. at 10° C./min cooling rate and held at −40° C. for 3 minutes. The sample was then heated to 150° C. at 10° C./minute heating rate. The cooling and second heating curves were recorded. The melting peak ($T_m$) and cooling peak ($T_c$) were determined.

Where a minor melting or cooling peak was observed, the peak was noted as $T_{m2}$ or $T_{c2}$. The heat of fusion, $T_m$ and $T_c$ of each example are listed in Table 9 below.

GPC Method. The gel permeation chromatographic system consisted of either a Polymer Laboratories Model PL-210 or a Polymer Laboratories Model PL-220 instrument. The column and carousel compartments were operated at 140° C. Three Polymer Laboratories 10-micron Mixed-B columns were used. The solvent was 1,2,4-trichlorobenzene. The samples were prepared at a concentration of 0.1 grams of polymer in 50 milliliters of solvent containing 200 ppm of butylated hydroxytoluene (BHT). Samples were prepared by agitating lightly for 2 hours at 160° C. The injection volume used was 100 microliters and the flow rate was 1.0 ml/minute.

Calibration of the GPC column set was performed with 21 narrow molecular weight distribution polystyrene standards with molecular weights ranging from 580 to 8,400,000, daltons arranged in 6 "cocktail" mixtures with at least a decade of separation between individual molecular weights. The standards were purchased from Polymer Laboratories (Shropshire, UK). The polystyrene standards were prepared at 0.025 grams in 50 milliliters of solvent for molecular weights equal to or greater than 1,000,000, and 0.05 grams in 50 milliliters of solvent for molecular weights less than 1,000,000. The polystyrene standards were dissolved at 80° C. with gentle agitation for 30 minutes. The narrow standards mixtures were run first and in order of decreasing highest molecular weight component to minimize degradation. The polystyrene standard peak molecular weights were converted to polyethylene molecular weights using the following equation (as described in Williams and Ward, *J. Polym. Sci., Polym. Let.*, 6, 621 (1968)): $M_{polyethylene}=0.431 (M_{polystyrene})$. Polyetheylene equivalent molecular weight calculations are performed using Viscotek TriSEC software Version 3.0. In Table 9, the weight average molecular weight $M_w$, the number average molecular weight $M_n$, and their ratio $M_w/M_n$ are reported.

Density. Samples for density measurement were prepared according to ASTM D 1928. Density measurements were made within one hour of sample pressing using ASTM D792, Method B, which is incorporated herein by reference. The density of each example is listed in Table 9 below.

Melt Index. Melt index, $I_2$, was measured in accordance with ASTM D 1238, Condition 190° C./2.16 kg. Melt index, $I_{10}$, is also measured in accordance with ASTM D 1238, Condition 190° C./10 kg. The $I_2$, $I_{10}$ and $I_{10}/I_2$ ratio of each example are listed in Table 9 below.

TABLE 8

Process Conditions and Results for Examples 20-26.

| Example | C$_2$H$_4$ kg/hr | C$_8$H$_{16}$ kg/hr | Solv. kg/hr | H$_2$ sccm[1] | Temp °C. | Cat A1[2] ppm | Cat A1 Flow kg/hr | Cat B2[3] ppm | Cat B2 Flow kg/hr | DEZ Conc. % | DEZ Flow kg/hr |
|---|---|---|---|---|---|---|---|---|---|---|---|
| 20[8] | 25.0 | 14.5 | 150.2 | 4122 | 120 | 410 | 0.26 | 200 | 0.12 | 0.0 | 0.00 |
| 21[8] | 25.0 | 14.2 | 150.4 | 267 | 120 | 410 | 0.28 | 200 | 0.10 | 3.0 | 0.47 |
| 22[8] | 25.0 | 15.8 | 149.3 | 55 | 120 | 378 | 0.33 | 100 | 0.21 | 3.0 | 0.79 |
| 23[9] | 2.5 | 4.1 | 22.0 | 2 | 120 | 150 | 0.097 | 76.6 | 0.036 | 0.532 | 0.2 |
| 24[9] | 2.8 | 4.1 | 21.6 | 2 | 120 | 150 | 0.095 | 76.6 | 0.041 | 0.532 | 0.2 |
| 25[10] | 2.5 | 4.5 | 21.0 | 345 | 121 | 150 | 0.092 | 76.6 | 0.049 | 1.0 | 0.3 |
| 26[10] | 2.7 | 3.6 | 21.0 | 200 | 121 | 150 | 0.094 | 76.6 | 0.049 | 1.0 | 0.3 |

| Example | Cocat 1 Conc. ppm | Cocat 1 Flow kg/hr | Cocat 2 Conc. ppm | Cocat 2 Flow kg/hr | Zn[4] in polymer ppm | Poly Rate[5] kg/hr | Conv. %[6] | Solids % | Eff.[7] |
|---|---|---|---|---|---|---|---|---|---|
| 20[8] | 4500 | 0.30 | 524 | 0.29 | 0 | 38.8 | 88.3 | 17.5 | 293 |
| 21[8] | 4583 | 0.29 | 524 | 0.22 | 370 | 38.4 | 88.4 | 17.4 | 281 |
| 22[8] | 4500 | 0.32 | 260 | 0.75 | 588 | 40.3 | 88.3 | 18.0 | 278 |
| 23[9] | 1008 | 159 | 0 | 0 | 244 | 4.0 | 89.0 | 14.0 | 231 |
| 24[9] | 1008 | 163 | 0 | 0 | 250 | 4.0 | 90.0 | 14.0 | 230 |
| 25[10] | 1008 | 0.17 | 0 | 0 | 732 | 4.1 | 90.0 | 16.4 | 233 |
| 26[10] | 1008 | 0.16 | 0 | 0 | 750 | 4.0 | 90.0 | 16.0 | 232 |

[1]standard cm$^3$/min
[2][N-(2,6-di(1-methylethyl)phenyl)amido)(2-isopropylphenyl)(α-naphthalen-2-diyl(6-pyridin-2-diyl)methane)]hafnium dimethyl
[3]bis-(1-(2-methylcyclohexyl)ethyl)(2-oxoyl-3,5-di(t-butyl)phenyl)immino) zirconium dibenzyl
[4]ppm in final product calculated by mass balance
[5]polymer production rate
[6]weight percent ethylene conversion in reactor
[7]efficiency, kg polymer/g M where g M = g Hf + g Z
[8]Additive package: 1000 ppm Irgafos 168, 250 ppm Irganox 1076, 200 ppm Irganox 1010, and 100 ppm Chimmasorb 2020.
[9]Additive package: 1000 ppm Irgafos 168, 250 ppm Irganox 1076, 200 ppm Irganox 1010, and 60 ppm Chimmasorb 2020.
[10]Additive package: 1200 ppm Irganox 1010.

TABLE 9

Various Physical Properties of Examples 20-24 and Other Comparative Polymers

| Example | Density (g/cm$^3$) | I$_2$[7] | I$_{10}$[7] | I$_{10}$/I$_2$[7] | M$_w$ (g/mol) | M$_n$ (g/mol) | M$_w$/M$_n$ | Heat of Fusion (J/g) | T$_m$/T$_{m2}$ (°C.) | T$_c$/T$_{c2}$ (°C.) | T$_{CRYSTAF}$ (°C.) | T$_m$ − T$_{CRYSTAF}$ (°C.) | CRYSTAF Peak Area (percent) |
|---|---|---|---|---|---|---|---|---|---|---|---|---|---|
| 20 | 0.8741 | 1.0 | 13.0 | 13.0 | 148,300 | 13,100 | 11.3 | 50 | 122 | 107 | 77 | 46 | 14 |
| 21 | 0.8750 | 4.9 | 33.5 | 6.8 | 81,800 | 41,700 | 2.0 | 49 | 121 | 97 | 36 | 84 | 12 |
| 22 | 0.8774 | 11.2 | 75.2 | 6.7 | 66,400 | 33,700 | 2.0 | 49 | 119 | 99 | 40 | 79 | 13 |
| 23 | 0.8667 | 1.2 | 8.2 | 6.8 | 126,200 | 57,100 | 2.2 | 22 | 116 | 86 | 30 | 86 | 6 |
| 24 | 0.8771 | 0.9 | 6.2 | 6.9 | 124,000 | 60,200 | 2.1 | 58 | 117 | 97 | 40 | 77 | 47 |
| ENGAGE ® 8100[1] | 0.8710 | 1.1 | 8.2 | 7.4 | 114,500 | 56,500 | 2.0 | 48 | 59 | 45 | NM | NA | NM |
| ENGAGE ® 8200[2] | 0.8712 | 4.9 | 37.1 | 7.6 | 79,900 | 39,200 | 2.0 | 52 | 64 | 46 | NM | NA | NM |
| LPE[3] | 0.8707 | 10.4 | 87.4 | 8.4 | 67,200 | 31,400 | 2.1 | 52 | 64/49 | 46 | NM | NA | NM |
| [70% LPE & 30% 12450N[4]][8] | 0.8936 | 11.4 | 84.0 | 7.4 | 65,300 | 25,500 | 2.6 | 98 | 127/66 | 114/49 | NM | NA | NM |
| KRATON ® 1652[5] | 0.9076 | 0.24 | 2.57 | 10.7 | 37,400 | 34,400 | 1.1 | 17 | 14 | 3 | NM | NA | NM |
| VECTOR ® 4211[6] | 0.9417 | 3.1 | 23.7 | 7.6 | 53,500 | 49,300 | 1.1 | ND | ND | ND | NM | NA | NM |

[1]ENGAGE ® 8100 is a polyolefin elastomer obtained from The Dow Chemical Co., Midland, MI.
[2]ENGAGE ® 8200 is a polyolefin elastomer obtained from The Dow Chemical Co., Midland, MI.
[3]LPE is a homogeneously branched substantially linear polyethylene as described by Lai et al. in U.S. Pat. Nos. 5,272,236, 5,278,272, 5,665,800 and 5,783,638.
[4]12540N is high density polyethylene from The Dow Chemical Company, Midland, MI.
[5]KRATON ® 1652 is a SEBS copolymer obtained from Kraton Polymers, Houston, TX.
[6]VECTOR ® 4211 is a SIS from Dexco Polymers, Houston, TX.
[7]Measured at 190° C.
[8]This sample was produced by blending the two components in a Haake mixer bowl.
NM: Not measured
NA: Not applicable
ND: Not detected Tensile Mechanical Properties. Stress-strain behavior in uniaxial tension was measured using ASTM D 1708 microtensile specimens. Samples were stretched with an Instron at 500% min$^{-1}$ at 21° C. The tensile strength and elongation at break of each example were reported from an average of 5 specimens and are listed in Table 10 below.

Thermal Mechanical Analysis (TMA). The penetration temperature was conducted on 30 mm diameter×3.3 mm thick, compression molded discs, formed at 180° C. and 10 MPa molding pressure for 5 minutes and then air quenched. The instrument used was a Perkin-Elmer TMA 7. In the test, a probe with 1.5 mm radius tip (P/N N519-0416) was applied to the surface of the sample disc with 1 N force. The temperature was raised at 5° C./minute from 25° C. The probe penetration distance was measured as a function of temperature. The experiment ended when the probe had penetrated 1 mm into the sample. The 1 mm penetration temperature of each example is listed in Table 10 below.

TABLE 10

The Tensile and Thermal Mechanical Properties of Examples 20-26, ENGAGE ® 8100, ENGAGE ® 8200, KRATON ® 1652, LPE[3], 12450N and VECTOR ® 4211.

| Example | TMA-1 mm penetration (° C.) | Tensile Strength (MPa) | Elongation at Break (%) |
|---|---|---|---|
| 20 | 50 | 8 | 1,349 |
| 21 | 100 | 13 | 1,459 |
| 22 | 101 | 9 | 1,623 |
| 23 | 96 | 12 | 1,355 |
| 24 | 112 | 22 | 955 |
| 25 | 41 | NM | NM |
| 26 | 54 | NM | NM |
| ENGAGE ® 8100[1] | 70 | 15 | 829 |
| ENGAGE ® 8200[2] | 56 | 6 | 563 |
| LPE[3] | 53 | 12 | 1,277 |
| [70% LPE &30% 12450N[4]][7] | 62 | 15 | 1,097 |
| KRATON ® 1652[5] | 107 | 32 | 609 |
| VECTOR ® 4211[6] | 85 | 15 | 1209 |

[1]ENGAGE ® 8100 is a polyolefin elastomer obtained from The Dow Chemical Co., Midland, MI.
[2]ENGAGE ® 8200 is a polyolefin elastomer obtained from The Dow Chemical Co., Midland, MI.
[3]LPE is a homogeneously branched substantially linear polyethylene as described by Lai et al. in U.S. Pat. Nos. 5,272,236, 5,278,272, 5,665,800 and 5,783,638.
[4]12540N is high density polyethylene from The Dow Chemical Company, Midland, MI.
[5]KRATON ® 1652 is a SEBS copolymer obtained from Kraton Polymers, Houston, TX.
[6]VECTOR ® 4211 is a SIS from Dexco Polymers, Houston, TX.
[7]This sample was produced by blending the two components in a Haake mixer bowl.

Ethylene/α-Olefin Interpolymers Examples 27-31, 31a AND 31b

Examples 27, 29, and 31b were prepared using a process similar to the one as described herein for Example 22.

Process Details for Examples 28, 30, 31 and 31a

Continuous solution polymerizations are carried out in a computer controlled well-mixed reactor. Purified mixed alkanes solvent (ISOPAR™ E available from ExxonMobil Chemical Company), ethylene, 1-octene, and hydrogen (where used) are combined and fed to a 39 gallon reactor. The feeds to the reactor are measured by mass-flow controllers. The temperature of the feed stream is controlled by use of a glycol cooled heat exchanger before entering the reactor. The catalyst component solutions are metered using pumps and mass flow meters. The reactor is run liquid-full at approximately 725 psig pressure. Upon exiting the reactor, water and additive are injected in the polymer solution. The water hydrolyzes the catalysts, and terminates the polymerization reactions. The post reactor solution is then heated in preparation for a two-stage devolatization. The solvent and unreacted monomers are removed during the devolatization process. The polymer melt is pumped to a die for underwater pellet cutting. Process details for interpolymers of Examples 27-31, 31a, and 31b and results are contained in Table 10a. Selected polymer properties are provided in Tables 10b and 10c.

TABLE 10a

Process Conditions and Results for Examples 27-31, 31a-31d.

| Interpolymer Example | $C_2H_4$ kg/hr | $C_8H_{16}$ kg/hr | Solv. kg/hr | $H_2$ sccm[1] | Temp ° C. | Cat A1[2] ppm | Cat A1 Flow kg/hr | Cat B2[3] ppm | Cat B2 Flow kg/hr | DEZ Conc. ppm | DEZ Flow kg/hr |
|---|---|---|---|---|---|---|---|---|---|---|---|
| 27[8] | 22.8 | 45.4 | 179.7 | 217 | 120 | 400 | 0.27 | 100 | 0.087 | 3.0 | 0.25 |
| 28[8] | 55.4 | 30.2 | 426.7 | 716 | 120 | 526 | 0.63 | 299 | 0.23 | 4.8 | 0.43 |
| 29[8] | 28.8 | 43.4 | 200.6 | 115 | 126 | 378 | 0.34 | 109 | 0.46 | 3.0 | 0.33 |
| 30[8] | 50.4 | 36.0 | 430.2 | 2499 | 120 | 543 | 0.60 | 299 | 0.12 | 5.0 | 0.41 |
| 31[8] | 54.9 | 32.7 | 420.7 | 547 | 120 | 526 | 0.72 | 299 | 0.24 | 4.8 | 0.86 |
| 31[8] | 55.4 | 33.2 | 426.7 | 600 | 120 | 555 | 0.94 | 299 | 0.38 | 5.0 | 1.23 |
| 31b[8] | 25.0 | 47.9 | 181.9 | 60 | 120 | 500 | 0.29 | 200 | 0.18 | 5.0 | 0.66 |

TABLE 10a-continued

Process Conditions and Results for Examples 27-31, 31a-31d.

| | | | | | | | | | | |
|---|---|---|---|---|---|---|---|---|---|---|
| 31c[9] | 52.2 | 30.3 | 438.8 | 132 | 120 | 654 | 0.85 | 148 | 0.16 | 5.0 | 1.3 |
| 31d[9] | 48.6 | 43.4 | 393.1 | 520 | 115 | 235 | 1.65 | 148 | 0.25 | 5.0 | 1.0 |

| Inter-polymer Example | Cocat 1 Conc. ppm | Cocat 1 Flow kg/hr | Cocat 2 Conc. ppm | Cocat 2 Flow kg/hr | Zn in polymer ppm | Poly Rate[5] kh/hr | Conv. %[6] | Solids % | Eff.[7] |
|---|---|---|---|---|---|---|---|---|---|
| 27[8] | 4500 | 0.23 | 524 | 0.094 | 194 | 38.1 | 87.5 | 17.4 | 331 |
| 28[8] | 4786 | 0.79 | 348 | 0.49 | 228 | 89.7 | 88.6 | 18.5 | 224 |
| 29[8] | 4500 | 0.45 | 260 | 0.31 | 250 | 39.2 | 89.9 | 16.2 | 220 |
| 30[8] | 5140 | 0.62 | 1377 | 0.12 | 238 | 85.5 | 87.6 | 17.7 | 237 |
| 31[8] | 4786 | 0.88 | 348 | 0.98 | 448 | 92.0 | 88.7 | 19.2 | 203 |
| 31[8] | 4925 | 1.22 | 1377 | 0.37 | 670 | 91.7 | 88.5 | 18.9 | 143 |
| 31b[8] | 6000 | 0.36 | 518 | 0.66 | 821 | 40.4 | 88.5 | 18.1 | 221 |
| 31c[9] | 5400 | 0.90 | 399 | 1.35 | 762 | 85.5 | 91.4 | 17.3 | 147 |
| 31d[9] | 5521 | 0.67 | 860 | 0.49 | 559 | 90.9 | 88.4 | 20.5 | 213 |

[1] standard cm$^3$/min
[2] [N-(2,6-di(1-methylethyl)phenyl)amido)(2-isopropylphenyl)(α-naphthalen-2-diyl(6-pyridin-2-diyl)methane)]hafnium dimethyl
[3] bis-(1-(2-methylcyclohexyl)ethyl)(2-oxoyl-3,5-di(t-butyl)phenyl)immino) zirconium dibenzyl
[4] ppm in final product calculated by mass balance
[5] polymer production rate
[6] weight percent ethylene conversion in reactor
[7] efficiency, kg polymer/g M where g M = g Hf + g Z
[8] Additive package: 1000 ppm Irgafos 168, 250 ppm Irganox 1076, 200 ppm Irganox 1010, and 100 ppm Chimmasorb 2020.
[9] Additive package: 1000 ppm Irgafos 168, 250 ppm Irganox 1076, 200 ppm Irganox 1010, and 80 ppm Chimmasorb 2020.

TABLE 10b

Various Physical Properties of Examples 27-31, 31a-31d.

| Example | Density (g/cc) | I2[1] | I10[1] | I10/I2[1] | Mw (g/mol) | Mn (g/mol) | Mw/Mn | Heat of Fusion (J/g) | $T_m$ (° C.) | $T_c$ (° C.) | Tcrystaf (° C.) | Tm-Tcrystaf (° C.) | Crystaf Peak Area |
|---|---|---|---|---|---|---|---|---|---|---|---|---|---|
| 27 | 0.8649 | 0.9 | 6.4 | 7.1 | 135,000 | 64,800 | 2.1 | 26 | 120 | 92 | 30 | 90 | 90 |
| 28 | 0.8769 | 1.0 | 6.9 | 6.9 | 127,200 | 58,200 | 2.2 | 57 | 120 | 97 | 41 | 79 | 13 |
| 29 | 0.8929 | 1.0 | 7.0 | 6.9 | 107,500 | 52,500 | 2.0 | 89 | 120 | 101 | 63 | 57 | 83 |
| 30 | 0.8665 | 5.0 | 36.0 | 7.3 | 93,200 | 41,100 | 2.3 | 30 | 122 | 97 | 30 | 92 | 93 |
| 31 | 0.8775 | 5.0 | 34.5 | 6.9 | 84,300 | 42,400 | 2.0 | 54 | 119 | 95 | 41 | 78 | 29 |
| 31a | 0.8783 | 14.6 | 96.9 | 6.6 | 63,600 | 32,100 | 2.0 | 51 | 116 | 94 | 37 | 80 | 13 |
| 31b | 0.8780 | 32.9 | 215.6 | 6.6 | 52,200 | 28,000 | 1.9 | 54 | 119 | 97 | 39 | 80 | 6 |
| 31c | 0.8699 | 15.2 | 95.6 | 6.3 | 60,100 | 30,900 | 1.9 | 44 | 108/40 | 74 | NM | NM | NM |
| 31d | 0.8701 | 13.9 | 100.2 | 7.2 | 68,400 | 34,800 | 2.0 | 31 | 117 | 98 | NM | NM | NM |

[1] Measured at 190° C.

TABLE 10c

The Tensile and Thermal Mechanical Properties of Examples 27-31, 31a-31d.

| Example | TMA, 1 mm penetration (° C.) | Tensile Strength (MPa) | Elongation at Break (%) |
|---|---|---|---|
| 27 | 83 | 12 | 1,305 |
| 28 | 107 | 16 | 1,002 |
| 29 | 119 | 26 | 1,063 |
| 30 | 68 | 8 | 1,646 |
| 31 | 100 | 13 | 1,313 |
| 31a | 95 | 9 | 1,520 |
| 31b | 88 | 4 | 1,507 |
| 31c | 51 | 8 | 1,420 |
| 31d | NM | 4 | 2,201 |

General Procedure for the Preparation of Adhesive Formulations

An 18 mm 30:1 L/D twin screw Leistritz extruder (Micro 18 GL, obtained from American Leistritz Extruder Corporation, Somerville, N.J.) with a Haake computer control program was used to formulate the adhesives. The screw design was a 30:1 L/D corotating twin screw with two sections of a series of kneading blocks for shear mixing preceeded by forwarding sections and followed by a pressuring section to force the blend through a strand die. The nonfeed throat zones were set at 80, 120, 145, 160, and 160° C. The die was heated to 160° C. The pressure sensitive adhesive (PSA) formulations were made using calibrated K-TRON feeders with one for the tackifier and another for the polymer. The oil was injected at Zone 2 using a calibrated positive displacement pump. The extruder screw was turned at a drive speed from 150 to 200 rpm depending on the blend to effect maximum blending. The extrudate was purged about 3 minutes prior to collection in a wax paper lined pan. The components of the hot melt adhesive (HMA) blends were dry blended and then fed as a single component through one K-TRON feeder. The blended feed was prodded continuously into the extruder using a high density polyethylene (HDPE) polyrod. As before, the extrudate was purged about 3 minutes prior to collection in the pan.

Although these particular samples were made on a micro twin screw extruder, other mixing methods could have been used as well. These include the use of a Sigma blade mixer or a Haake bowl mixer. A general procedure would be to preheat the mixer to about 163° C. (325° F.). In some cases a nitrogen blanket may be used on the mixer. The desired amount of tackifier and stabilizer are then added and mixed until melted completely. The polymer is then added while mixing until all of the polymer is in the mixer. The mixer would then be covered and the contents mixed until the formulation was smooth and free of lumps. The oil is then slowly added and mixed for about 15 minutes until totally smooth. The contents are then discharged into a suitable release lined container. The total batch time should not exceed two hours. This is a general description, and variations may occur depending on the components of the formulation.

TABLE 11

The Formulations and Viscosities of Adhesive Examples 32-69 and Comparatives L-Z and AA-AE.

| Adhesive Sample | Polymer | Tackifer | Polymer wt % | Tackifier wt % | Kaydol Oil[4] wt % | Brookfield Viscosity 177° C. (cP) |
|---|---|---|---|---|---|---|
| Ex. 32 | 23 | WINGTACK ® 95[1] | 25.5% | 54% | 20% | 69,285 |
| Ex. 33 | 24 | WINGTACK ® 95 | 25.5% | 54% | 20% | 24,745 |
| Comp. L | ENGAGE ® 8100[5] | WINGTACK ® 95 | 25.5% | 54% | 20% | 58,687 |
| Ex. 34 | 20 | WINGTACK ® 95 | 25.5% | 54% | 20% | 134,221 |
| Ex. 35 | 21 | WINGTACK ® 95 | 25.5% | 54% | 20% | 33,593 |
| Comp. M | ENGAGE ® 8200[6] | WINGTACK ® 95 | 25.5% | 54% | 20% | 18,266 |
| Ex. 36 | 22 | WINGTACK ® 95 | 25.5% | 54% | 20% | 10,958 |
| Comp. N | LPE[7] | WINGTACK ® 95 | 25.5% | 54% | 20% | 6,563 |
| Comp. O | 70% LPE & 30% 12450N[8] | WINGTACK ® 95 | 25.5% | 54% | 20% | 10,158 |
| Comp. P | KRATON ® 1652[9] | WINGTACK ® 95 | 25.5% | 54% | 20% | 8,488 |
| Comp. Q | VECTOR ® 4211[10] | WINGTACK ® 95 | 25.5% | 54% | 20% | 5,239 |
| Ex. 37 | 22 | EASTOTAC ® H142R[2] | 22.5% | 53% | 25% | 8,248 |
| Comp. R | LPE[7] | EASTOTAC ® H142R | 22.5% | 53% | 25% | 7,990 |
| Comp. S | 70% LPE & 30% 12450N[8] | EASTOTAC ® H142R | 22.5% | 53% | 25% | 12,537 |
| Ex. 38 | 22 | EASTOTAC ® H142R | 19.5% | 50% | 30% | 1,182 |
| Comp. T | LPE[7] | EASTOTAC ® H142R | 19.5% | 50% | 30% | 2,779 |
| Comp. U | 70% LPE & 30% 12450N[8] | EASTOTAC ® H142R | 19.5% | 50% | 30% | 3,204 |
| Ex. 39 | 22 | EASTOTAC ® H142R | 14.5% | 55% | 30% | 1,896 |
| Comp. V | LPE[7] | EASTOTAC ® H142R | 14.5% | 55% | 30% | 1,005 |
| Comp. W | 70% LPE & 30% 12450N[8] | EASTOTAC ® H142R | 14.5% | 55% | 30% | 3,569 |
| Ex. 40 | 23 | EASTOTAC ® H142R | 15% | 45% | 40% | 5,309 |
| Ex. 42 | 23 | EASTOTAC ® H142R | 20% | 40% | 40% | 15,376 |
| Ex. 43 | 23 | EASTOTAC ® H142R | 10% | 60% | 30% | 3,611 |
| Ex. 44 | 23 | EASTOTAC ® H142R | 26% | 54% | 20% | 189,959 |
| Ex. 45 | 23 | EASTOTAC ® H142R | 40% | 40% | 20% | >300,000 |
| Ex. 46 | 23 | EASTOTAC ® H142R | 10% | 50% | 40% | 535 |
| Ex. 47 | 24 | EASTOTAC ® H142R | 40% | 40% | 20% | >300,000 |
| Ex. 48 | 24 | EASTOTAC ® H142R | 20% | 40% | 40% | 35,043 |
| Comp. X | KRATON ® G-1652 | EASTOTAC ® H142R | 20% | 40% | 40% | 951 |
| Comp. Y | ENGAGE ® 8100 | EASTOTAC ® H142R | 20% | 40% | 40% | 34,853 |
| Ex. 49 | 23 | WINGTACK ® 95 | 20% | 40% | 40% | 16,047 |
| Ex. 50 | 23 | EASTOTAC ® H142R | 26% | 47% | 27% | 106,102 |
| Ex. 51 | 23 | EASTOTAC ® H142R | 20% | 50% | 30% | 30,054 |
| Ex. 52 | 23 | EASTOTAC ® H142R | 30% | 40% | 30% | 172,151 |

TABLE 11-continued

The Formulations and Viscosities of Adhesive Examples 32-69 and Comparatives L-Z and AA-AE.

| Adhesive Sample | Polymer | Tackifer | Polymer wt % | Tackifier wt % | Kaydol Oil[4] wt % | Brookfield Viscosity 177° C. (cP) |
|---|---|---|---|---|---|---|
| Ex. 53 | 23 | EASTOTAC ® H142R | 10% | 70% | 20% | 943 |
| Ex. 54 | 23 | EASTOTAC ® H142R | 20% | 70% | 10% | 36,592 |
| Ex. 55 | 23 | EASTOTAC ® H142R | 30% | 70% | 0% | >300,000 |
| Ex. 56 | 23 | EASTOTAC ® H142R | 45% | 55% | 0% | >300,000 |
| Ex. 57 | 23 | EASTOTAC ® H142R | 60% | 40% | 0% | >300,000 |
| Ex. 58 | 23 | EASTOTAC ® H142R | 60% | 0% | 40% | >300,000 |
| Ex. 59 | 23 | EASTOTAC ® H142R | 40% | 0% | 60^ | >300,000 |
| Comp. Z | KRATON ® G-1652 | WINGTACK ® 95 | 30% | 54.50% | 15% | 5,829 |
| Comp. AA | ENGAGE ® 8100 | WINGTACK ® 95 | 30% | 54.50% | 15% | 234,012 |
| Comp. AB | 62% ENGAGE ® 8100 38% AFFINITY ® PL1880 | WINGTACK ® 95 | 30% | 54.50% | 15% | 118,100 |
| Ex. 60 | 7 | WINGTACK ® 95 | 30% | 54.50% | 15% | 243,073 |
| Ex. 61 | 5 | WINGTACK ® 95 | 30% | 54.50% | 15% | 141,845 |
| Ex. 62 | 8 | WINGTACK ® 95 | 30% | 54.50% | 15% | >300,000 |
| Ex. 63 | 13 | WINGTACK ® 95 | 30% | 54.50% | 15% | 160,903 |
| Ex. 64 | 16 | WINGTACK ® 95 | 30% | 54.50% | 15% | 223,389 |
| Comp. AC | KRATON ® G-1652 | ESCOREZ ™ 5400[3] | 30% | 29.50% | 40% | 3.641 |
| Comp. AD | ENGAGE ® 8100 | ESCOREZ ™ 5400 | 30% | 29.50% | 40% | 89,981 |
| Comp. AE | 62% ENGAGE ® 8100/ 38% AFFINITY ® PL1880 | ESCOREZ ™ 5400 | 30% | 29.50% | 40% | 66,267 |
| Ex. 65 | 8 | ESCOREZ ™ 5400 | 30% | 29.50% | 40% | 133,097 |
| Ex. 66 | 5 | ESCOREZ ™ 5400 | 30% | 29.50% | 40% | 105,602 |
| Ex. 67 | 7 | ESCOREZ ™ 5400 | 30% | 29.50% | 40% | 109,820 |
| Ex. 68 | 13 | ESCOREZ ™ 5400 | 30% | 29.50% | 40% | 182,461 |
| Ex. 69 | 16 | ESCOREZ ™ 5400 | 30% | 29.50% | 40% | 177,774 |

[1]WINGTACK ® 95 is a tackifier from GoodYear Chemical, Beaumont, TX.
[2]EASTOTAC ® H142R is a tackifier from Eastman Company, Kingsport, Tennessee.
[3]ESCOREZ ™ 5400 is a tackifier from ExxonMobil Chemical Company, Houston, TX.
[4]Kaydol Oil is a mineral oil from AMCO Chemical, Oakland, CA.
[5]ENGAGE ® 8100 is a polyolefin elastomer obtained from The Dow Chemical Co., Midland, MI.
[6]ENGAGE ® 8200 is a polyolefin elastomer obtained from The Dow Chemical Co., Midland, MI.
[7]LPE is a homogeneously branched substantially linear polyethylene as described by Lai et al. in U.S. Pat. Nos. 5,272,236, 5,278,272, 5,665,800 and 5,783,638.
[8]12540N is high density polyethylene from The Dow Chemical Company, Midland, MI.
[9]KRATON ® 1652 is a SEBS copolymer obtained from Kraton Polymers, Houston, TX.
[10]VECTOR ® 4211 is a SIS from Dexco Polymers, Houston, TX.

Examples 20-24 and 5, 7, 8, 13, and 16 and some commercial polymers as shown in Table 11 above were formulated into pressure sensitive adhesives (PSA) by the addition of a tackifier and Kaydol oil. The resulting viscosity of the formulated system was low as compared to the base polymer. The viscosity of the PSA was measured to indicate its ability to be applied easily onto a substrate. Preferred ranges of viscosity for the formulated adhesive are from about 500 to about 300,000 cP at 350° F. (177° C.) as measured by Brookfield viscosity, more preferably from about 500 to about 150,000 cP, and most preferably from about 500 to about 50,000 cP. Especially preferred are higher flow multi-block samples (i.e., ~10 $I_2$) which yielded especially low viscosities of from about 1 to about 11,000 cP at 350° F. depending on the percentage and type of tackifier and oil used.

Figure 8:
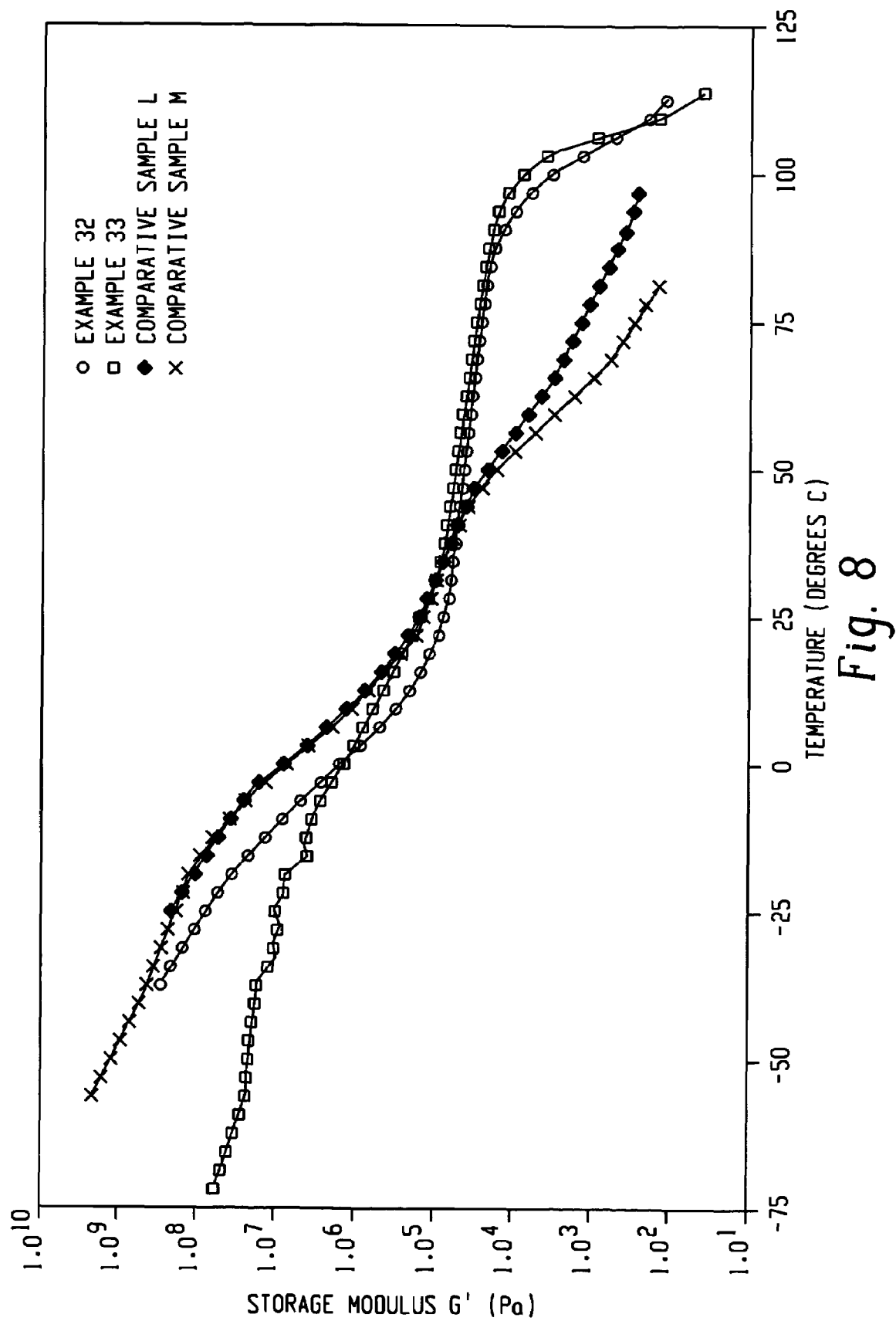
FIG. 8 shows plots of Storage Modulus (G') versus temperature for Examples 32 (represented by the circles) and 33 (represented by the open squares) as compared to Comparative Examples L (represented by the solid diamonds) and M (represented by the "X" symbols).
Figure 9:
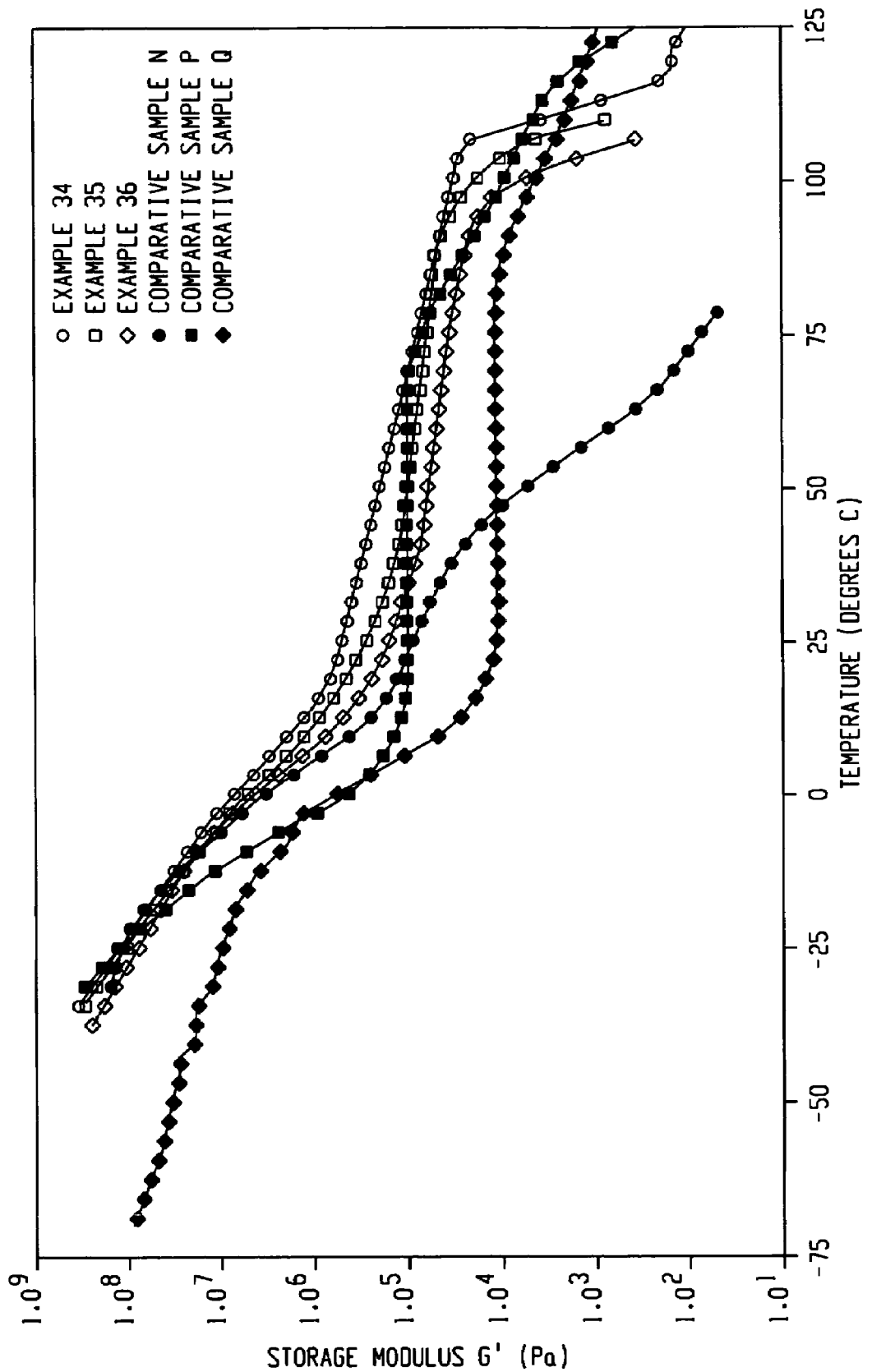
FIG. 9 shows plots of Storage Modulus (G') versus temperature for Examples 34 (represented by the open circles), 35 (represented by the open squares) and 36 (represented by the open diamonds), as compared to Comparative Examples N (represented by the solid circles), P (represented by the solid squares) and Q (represented by the solid diamonds).

FIG. 8 shows plots of storage modulus versus temperature for Examples 32-33, as compared to comparative Examples L and M. FIG. 9 shows plots of storage modulus versus temperature for Examples 34-36, as compared to comparative Examples N, P, and Q.

Coating of Pressure Sensitive Adhesive Samples

All pressure sensitive adhesive samples were coated as hot melts by hand onto 2 mil (50.8 microns) Mylar film using a P.G. & T. CO. #1 applicator (stainless steel wet film applicator available from the Paul N. Gardner Company, Pompano Beach, Fla.) which was preheated to the adhesive application temperature of 177° C. (350° F.). Just prior to drawing down the adhesives onto the Mylar film, the coating edge of the applicator was heated briefly over a Bunsen burner to help facilitate obtaining as smooth and streak free coating as possible. The adhesive coat weight for all samples was 25 gsm (grams per square meter).

Coating of Hot Melt Adhesive Samples

All hot melt adhesive samples were coated as hot melts by hand onto Kraft paper (Inland board stock) using a P.G. & T. CO. #1 applicator (stainless steel wet film applicator available from the Paul N. Gardner Company) which was preheated to the adhesive application temperature of 177° C. (350° F.). If the viscosity of the formulation was too high to yield an easily flowable formulation, the temperature was raised to 191° C. (375° F.). These samples were prepared using two sheets of 40 pound Kraft paper, each of about 6×12 inches (152×305 mm) dimensions. On the bottom sheet, lengthwise and separated by a gap of 1 inch (25 mm) were adhered in parallel fashion two 1.75 or 2 inches (45 or 51 mm) wide strips of a one sided, pressure-sensitive tape such as masking tape. The adhesive sample to be tested was heated to 177° C. (350° F.) and drizzled in an even manner down the center of the gap formed between the tape strips. Then, before the adhesive could unduly thicken, two glass rods (applicators), one rod riding immediately upon the tapes and shimmed on each side of the gap with a strip of the same tape followed by the second rod and (between the two rods) the second sheet of paper, were slid down the length of the sheets. This was done in a fashion such that the first rod evenly spread the adhesive in the gap between the tape strips and the second rod evenly compressed the second sheet over the top of the gap and on top of the tape strips. Note that just prior to drawing down the adhesives onto the Kraft paper, the coating edge of the applicator was heated briefly over a Bunsen burner to help facilitate obtaining as smooth and streak free coating as possible. Thus a single 1 inch wide strip of sample adhesive was created, between the two tape strips, and bonding the paper sheets. The sheets so bonded were cut crosswise into strips of width 1 inch and length of about 3 inches, each strip having a 1×1 inch (25×25 mm) adhesive sample bond in the center. The adhesive coat weight for all samples was 25 grams per square meter.

Adhesive Test Procedures

Brookfield Viscosity

Melt viscosity is determined by ASTM D3236, which is incorporated herein by reference, using a Brookfield Laboratories DVII+ Viscometer equipped with disposable aluminum sample chambers. In general, a SC-31 spindle is used, suitable for measuring viscosities in the range of from 30 to 100,000 centipoise (cP). If the viscosity is outside this range, an alternate spindle should be used which is suitable for the viscosity of the polymer. A cutting blade is employed to cut samples into pieces small enough to fit into the 1 inch wide, 5 inches long samples chamber. The disposable tube is charged with 8-9 grams of polymer. The sample is placed in the chamber, which is in turn inserted into a Brookfield Thermosel and locked into place with bent needle-nose pliers. The sample chamber has a notch on the bottom that fits in the bottom of the Brookfield Thermosel to ensure that the chamber is not allowed to turn when the spindle is inserted and spinning. The sample is heated to the desired temperature (177° C./350° F.). The viscometer apparatus is lowered and the spindle submerged into the sample chamber. Lowering is continued until brackets on the viscometer align on the Thermosel. The viscometer is turned on, and set to a shear rate which leads to a torque reading in the range of 40 to 70 percent. Readings are taken every minute for about 15 minutes, or until the values stabilize, and then the final reading is recorded. The Brookfield viscosity test results are listed in Table 11 above.

Solid State DMA of Adhesive Formulations

Dynamic Mechanical Analysis (DMA) of pressure sensitive formulated adhesives was measured on an ARES controlled strain rheometer (TA instruments) equipped with 7.9 mm parallel plates. The sample was subjected to successive temperature steps from −70° C. to 200° C. (3° C. per step). At each temperature the rheological properties (storage modulus G', loss modulus G", complex viscosity η*, tan delta or ratio of G"/G', etc.) were measured at an angular frequency of 1 rad/s. Other parameters used were a soak time of 30 seconds, an initial strain of 0.1%, a delay before test of 2 minutes, autotension (in compression mode (applying constant static force) with an initial static force of 1 g, an autotension sensitivity of 5 g (sample modulus less than or equal to $5\times10^6$ dynes/cm$^2$), and autostrain (maximum applied strain of 5%, torque range=150-1500 g-cm, strain adjustment=50%).

Some of the samples could be molded into plaques while others, which were too sticky, could not be molded. Samples that could be molded were pressed at 177° C. (350° F.) for about three minutes into a plaque using Teflon shims. The desired thickness for the plaque was about 2.5 mm. (If the sample could not be pressed then a small portion was placed directly on the bottom plate (7.9 mm parallel plate). After molding, a 5/16" punch was used to remove a test specimen from the plaque. The specimen was loaded into the ARES rheometer fitted with 7.9 mm parallel plates. The sample was placed on the bottom plate at about room temperature. The top plate was brought down until it touched the sample and created a normal force of 50 to 300 g. Good contact was made on both the bottom and top plates. The temperature control chamber was closed and the sample was heated to 150° C. to 170° C. and allowed to equilibrate at the temperature for about 5 minutes. The sample was compressed to 2 mm thickness. The chamber was opened and excess sample was trimmed. While the sample was still hot, the gap setting was decreased by about 0.1 mm to 1.9 mm. The chamber was closed and the sample was allowed to equilibrate again for about 3 minutes. The temperature was decreased to −70° C. After 3 minutes at −70° C., the sample was tested. The DMA test results are listed in Table 12 below. The values in Table 12 were chosen at the closest temperature increment to the stated temperature. Thus the values could be taken at a maximum of 1.5° C. different than the stated value.

TABLE 12

The DMA Testing Data of Adhesives.

| Adhesive Example | G' (Pa) at 0° C. | G' (Pa) at 25° C. | G' (Pa) at 50° C. | G' (Pa) at 75° C. | G' (Pa) at 100° C. | G' (0° C.)/ G' (50° C.) | G' (25° C.)/ G' (75° C.) | Tg (° C.) Tan δ Peak |
|---|---|---|---|---|---|---|---|---|
| Ex. 32 | 1.52E+06 | 8.27E+04 | 4.94E+04 | 3.14E+04 | 2.86E+03 | 31 | 3 | 3 |
| Ex. 33 | 1.73E+06 | 1.14E+05 | 4.43E+04 | 3.20E+04 | 6.60E+03 | 39 | 4 | 11 |

TABLE 12-continued

The DMA Testing Data of Adhesives.

| Adhesive Example | G' (Pa) at 0° C. | G' (Pa) at 25° C. | G' (Pa) at 50° C. | G' (Pa) at 75° C. | G' (Pa) at 100° C. | G' (0° C.)/ G' (50° C.) | G' (25° C.)/ G' (75° C.) | Tg (° C.) Tan δ Peak |
|---|---|---|---|---|---|---|---|---|
| Comp. L | 1.06E+07 | 1.69E+05 | 2.45E+04 | 1.55E+03 | NM | 433 | 109 | 8 |
| Ex. 34 | 8.62E+06 | 4.81E+05 | 2.03E+05 | 8.31E+04 | 3.28E+04 | 42 | 6 | 9 |
| Ex. 35 | 6.24E+06 | 2.70E+05 | 9.88E+04 | 6.03E+04 | 1.79E+04 | 63 | 4 | 8 |
| Comp. M | 8.86E+06 | 1.49E+05 | 1.85E+04 | 4.08E+02 | NM | 479 | 365 | 9 |
| Ex. 36 | 4.52E+06 | 1.44E+05 | 5.90E+04 | 3.95E+04 | 6.27E+03 | 77 | 4 | 9 |
| Comp. N | 4.34E+06 | 8.25E+04 | 7.36E+03 | 7.84E+01 | NM | 590 | 1052 | 9 |
| Comp. O | 1.75E+07 | 6.44E+05 | 1.41E+05 | 4.72E+04 | 3.08E+04 | 124 | 14 | 8 |
| Comp. P | 6.74E+05 | 9.66E+04 | 1.00E+05 | 7.56E+04 | 9.60E+03 | 7 | 1 | −1 |
| Comp. Q | 8.45E+05 | 1.20E+04 | 1.10E+04 | 1.24E+04 | 4.45E+03 | 77 | 1 | 9 |
| Ex. 37 | 1.08E+07 | 2.37E+05 | 5.41E+04 | 3.28E+04 | 1.16E+03 | 200 | 7 | 14 |
| Comp. R | 9.09E+06 | 1.02E+05 | 5.66E+03 | 1.35E+02 | NM | 1606 | 758 | 14 |
| Comp. S | 1.90E+07 | 5.62E+05 | 8.83E+04 | 3.52E+04 | 3.38E+04 | 215 | 16 | 12 |
| Ex. 38 | 3.78E+04 | 7.30E+03 | 4.99E+03 | 3.62E+03 | NM | 8 | 2 | 12 |
| Comp. T | 3.40E+06 | 3.73E+04 | 1.55E+03 | NM | NM | 2188 | NA | 9 |
| Comp. U | 3.27E+07 | 1.69E+06 | 5.16E+05 | 2.46E+05 | 1.25E+05 | 63 | 7 | 8 |
| Ex. 39 | 2.21E+04 | 2.12E+03 | 8.99E+02 | 1.02E+03 | NM | 25 | 2 | 15 |
| Comp. V | 1.31E+06 | 6.94E+03 | 1.63E+02 | 3.00E+01 | NM | 8037 | 231 | 8 |
| Comp. W | 1.74E+07 | 5.34E+05 | 8.54E+04 | 3.59E+04 | 3.26E+04 | 204 | 15 | 12 |
| Ex. 40 | NM | 2.11E+04 | 1.22E+04 | 6.11E+03 | 8.40E+01 | NA | 3 | NM |
| Ex. 42 | 1.02E+05 | 4.54E+04 | 2.94E+04 | 1.90E+04 | 2.58E+02 | 3 | 2 | −24 |
| Ex. 43 | 8.43E+03 | 8.68E+02 | 5.13E+02 | 2.72E+02 | NM | 16 | 3 | 11 |
| Ex. 44 | NM | 1.89E+04 | 1.00E+04 | 5.74E+03 | 2.14E+03 | NA | 3 | NM |
| Ex. 45 | 9.19E+05 | 3.16E+05 | 2.15E+05 | 1.41E+05 | 1.97E+04 | 4 | 2 | −16 |
| Ex. 46 | NM | 2.51E+02 | NM | NM | NM | NA | NA | NM |
| Ex. 47 | 1.40E+06 | 3.10E+05 | 2.07E+05 | 1.35E+05 | 1.90E+04 | 7 | 2 | −10 |
| Ex. 48 | 2.91E+05 | 9.51E+04 | 6.03E+04 | 4.01E+04 | 2.68E+03 | 5 | 2 | −19 |
| Comp. X | 8.78E+04 | 4.29E+04 | 3.53E+04 | 3.78E+04 | NM | 2 | 11 | −10 |
| Comp. Y | 3.34E+05 | 1.04E+05 | 1.54E+04 | 1.50E+03 | 1.00E+02 | 22 | 69 | −13 |
| Ex. 49 | 9.44E+04 | 3.97E+04 | 2.70E+04 | 1.85E+04 | 5.21E+02 | 4 | 2 | −19 |
| Ex. 50 | 7.48E+05 | 1.33E+05 | 8.67E+04 | 5.06E+04 | 3.11E+03 | 9 | 3 | −8 |
| Ex. 51 | NM | 7.08E+04 | 3.08E+04 | 1.52E+04 | 7.04E+02 | NA | 5 | −1 |
| Ex. 52 | 5.30E+05 | 1.75E+05 | 1.18E+05 | 7.36E+04 | 5.12E+03 | 4 | 2 | −16 |
| Ex. 54 | 6.61E+05 | 6.37E+04 | 2.44E+04 | 2.52E+03 | 3.85E+02 | 27 | 25 | 60 |
| Ex. 55 | 1.77E+08 | 1.31E+07 | 9.53E+05 | 1.30E+05 | 1.93E+04 | 186 | 101 | 44 |
| Ex. 56 | 5.48E+06 | 8.75E+05 | 5.03E+05 | 3.26E+05 | 9.46E+04 | 11 | 3 | −7 |
| Ex. 57 | 8.13E+06 | 1.03E+06 | 4.95E+05 | 2.95E+05 | 8.48E+04 | 16 | 3 | −4 |
| Ex. 58 | 8.36E+05 | 5.20E+05 | 3.37E+05 | 2.34E+05 | 5.75E+04 | 2 | 2 | 42 |
| Ex. 59 | 5.05E+05 | 3.00E+05 | 1.91E+05 | 1.31E+05 | 1.75E+04 | 3 | 2 | 42 |
| Comp. Z | 7.71E+05 | 2.63E+04 | 1.96E+04 | 1.69E+04 | 4.15E+03 | 39 | 2 | 5 |
| Comp. AA | 9.91E+06 | 2.06E+05 | 4.31E+04 | 4.60E+03 | 5.88E+02 | 230 | 45 | 8 |
| Comp. AB | 2.01E+05 | 2.93E+05 | 1.06E+05 | 3.05E+04 | 4.00E+02 | 2 | 10 | 18 |
| Ex. 60 | 1.78E+07 | 7.99E+05 | 2.76E+05 | 1.90E+05 | 1.08E+05 | 64 | 4 | 14 |
| Ex. 61 | 1.67E+07 | 5.40E+05 | 2.23E+05 | 1.53E+05 | 3.78E+04 | 75 | 4 | 14 |
| Ex. 62 | 1.37E+07 | 2.69E+05 | 1.22E+05 | 6.57E+04 | 7.34E+03 | 112 | 4 | 11 |
| Ex. 63 | 1.16E+07 | 1.02E+06 | 4.49E+05 | 2.75E+05 | 1.56E+05 | 26 | 4 | 1 |
| Ex. 64 | 3.86E+06 | 4.10E+05 | 2.55E+05 | 2.06E+05 | 8.54E+04 | 15 | 2 | 1 |
| Comp. AC | 1.41E+05 | 1.15E+05 | 9.48E+04 | 1.27E+04 | NM | 1 | 9 | −30 |
| Comp. AD | 3.51E+05 | 1.62E+05 | 2.22E+04 | 1.44E+04 | 2.81E+02 | 16 | 113 | −33 |
| Comp. AE | 5.37E+05 | 2.73E+05 | 1.34E+05 | 3.01E+04 | 1.42E+02 | 4 | 9 | −32 |
| Ex. 65 | 1.05E+06 | 6.24E+05 | 4.25E+05 | 2.75E+05 | 1.24E+05 | 2 | 2 | −37 |
| Ex. 66 | 4.40E+05 | 2.77E+05 | 1.90E+05 | 1.34E+05 | 3.47E+03 | 2 | 2 | −36 |
| Ex. 67 | 6.34E+05 | 3.99E+05 | 2.86E+05 | 1.89E+05 | 6.31E+04 | 2 | 2 | −37 |
| Ex. 68 | 2.80E+05 | 1.49E+05 | 9.92E+04 | 5.04E+04 | 2.10E+03 | 3 | 3 | −36 |
| Ex. 69 | 5.47E+05 | 3.67E+05 | 2.77E+05 | 1.62E+05 | 3.20E+04 | 2 | 2 | −38 |

Note that "NM" stands for "not measured."

The storage modulus data (G') of the adhesive compositions at various temperatures and their ratios, as well as the peak in the tan delta curve or $T_g$, are tabulated in Table 12 as they are often used as a means to characterize the goodness of a pressure sensitive adhesive (D. Satas (Ed.) *Handbook of pressure Sensitive Adhesive Technology*, Chapter 8, S. G. Chu, "*Viscoelastic Properties of Pressure Sensitive Adhesives*", p. 158-203, Van Nostrand Reinhold (1989). Adhesive properties were measured on selected samples and include SAFT, peel to stainless steel (SS) and polypropylene (PP), loop tack, and room temperature (RT) shear. The storage modulus (G') of some adhesive examples are shown in FIGS. 8 and 9.

In some embodiments, the storage moduli G' of the adhesive compositions at 25° C. are from about $1 \times 10^3$ to about $1 \times 10^6$ Pa, from about $2 \times 10^3$ to about $5 \times 10^5$ Pa, or from about $1 \times 10^4$ to about $5 \times 10^5$ Pa.

In other embodiments, the adhesive compositions have a relatively flat G' curve in the general temperature range of interest of use (i.e., from 0 to 75° C.), indicating the G' and other properties related to G' have a relatively small temperature dependence. In further embodiments, the G' of some PSA's (e.g., Examples 32-69) made from interpolymers disclosed herein have a relatively flat G' curve in the temperature range from 0 to 75° C. which is similar to those PSA's (e.g., Comparatives P, Q, X, Z and AC) made from conventional block copolymers (KRATON® and VECTOR®). In particular embodiments, the ranges of storage modulus ratio G'(25° C.)/G'(75° C.) are from about 1:1 to about 110:1, from about 1:1 to about 75:1, from about 1:1 to about 25:1, from about 1:1 to about 20:1, from about 1:1 to about 15:1, from about 1:1 to about 10:1, from about 1:1 to about 9:1, from about 1:1 to about 8:1, from about 1:1 to about 7:1, from about 1:1 to about 6:1, from about 1:1 to about 5:1, or from about 1:1 to about 4:1.

Shear Adhesion Failure Temperature (SAFT)

Shear adhesion failure temperature (SAFT) of each sample was measured according to ASTM D 4498 with a 500 gram weight in the shear mode. The tests were started at room temperature (25° C./77° F.) and the oven temperature was ramped at an average rate of 0.5° C./minute. The temperature at which the specimen failed was recorded. This measurement was used as an indication of the heat resistance of the composition which is important for shipping. The SAFT test results are listed in Table 13 below.

Peel Adhesion Failure Temperature (PAFT)

Peel adhesion failure temperature (PAFT) was tested according to ASTM D 4498 with a 100 gram weight in the peel mode. The tests were started at room temperature (25° C./77° F.) and the temperature was increased at an average rate of 0.5° C./minute. The PAFT test results are listed in Table 13 below.

180 Degree Peel Adhesion to Stainless Steel and Polypropylene

The 180 degree peel adhesion to stainless steel and also to polypropylene test panels was tested according to the Pressure Sensitive Tape Council PSTC-1 method with a peel rate of 12"/minute. The 180 degree peel adhesion to stainless steel (SS) and polypropylene (PP) substrates are listed in Table 13 below.

Loop Tack

The loop tack was tested by method ASTM 6195-03 test method-A, which is incorporated herein by reference. The loop tack test results are listed in Table 13 below.

RT Shear

Static shear at room temperature (RT) was tested using a 1 kg weight and a modified ASTM-D-4498, which is incorporated herein by reference. The static shear at room temperature test results are listed in Table 13 below.

TABLE 13

The SAFT, 180 Degree Peel Adhesion To Stainless Steel (SS) and Polypropylene (PP), Loop Tack, And Room Temperature (RT) Shear Test Results of PSA Examples.

| PSA Example | SAFT (° F.) | SAFT (° C.) | Mean Peel Adhesion to SS (lb) | Mean Peel Adhesion to PP (lb) | Mean Loop Tack (lb) | RT Shear (min.) |
| --- | --- | --- | --- | --- | --- | --- |
| Ex. 32 | 129 | 54 | 3.2 | 0.2 | NM | NM |
| Ex. 33 | 111 | 44 | 1.6 | 0.4 | NM | NM |
| Comp. L | 137 | 58 | 0.4 | 0.1 | NM | NM |
| Ex. 34 | 147 | 64 | 3 | 3.2 | NM | NM |
| Ex. 35 | 147 | 64 | 0.8 | 0 | NM | NM |
| Comp. M | 137 | 58 | 1.4 | 1.1 | NM | NM |
| Ex. 36 | 117 | 47 | 4.1 | 4.2 | 0.9 | NM |
| Comp. N | 129 | 54 | 4.4 | 4.2 | 1.9 | NM |
| Comp. O | 115 | 46 | 3.4 | 4.1 | 0.9 | NM |
| Comp. P | 191 | 88 | 4.9 | 3.6 | NM | NM |
| Comp. Q | 104 | 40 | 6.6 | 6.5 | 6.3 | NM |
| Ex. 37 | 153 | 67 | 3.2 | 0.8 | 0 | NM |
| Comp. R | 132 | 56 | 3 | 2.8 | 0 | NM |
| Comp. S | 140 | 60 | 0.8 | 0.7 | 0 | NM |
| Ex. 38 | 104 | 40 | 5.8 | 4.1 | 9.5 | NM |
| Comp. T | 125 | 52 | 7 | 6.7 | 0.9 | NM |
| Comp. U | 101 | 38 | 2.4 | 1.8 | 3.9 | NM |
| Ex. 39 | 131 | 55 | 6.9 | 6.9 | 0.5 | NM |
| Comp. V | 116 | 47 | 6.8 | 5.7 | 2.5 | NM |
| Comp. W | 99 | 37 | 3.6 | 3.1 | 6.3 | NM |
| Comp. Z | 180 | 82 | 6.9 | NM | NM | >5000 |
| Comp. AA | 153 | 67 | 0.33 | NM | NM | >5000 |
| Comp. AB | 134 | 57 | 0.27 | NM | NM | >5000 |
| Ex. 60 | 130 | 54 | 0.24 | NM | NM | >5000 |
| Comp. AC | 155 | 68 | 0.2 | NM | NM | >5000 |
| Comp. AD | 87 | 31 | <0.1 | NM | NM | <1 |
| Comp. AE | 81 | 27 | <0.1 | NM | NM | <1 |
| Ex. 65 | 89 | 32 | <0.1 | NM | NM | 2 |

In some embodiments, the SAFT of the adhesive compositions are greater than or equal to 90° F., greater than or equal to 110° F., greater than or equal to 130° F. or greater than or equal to 150° F. In general, the adhesive compositions having a high SAFT can be used at high temperatures.

In other embodiments, the 180 degree peel adhesion of the adhesive compositions to SS are greater than 0.1 lb, greater than 1.5 lb, or greater than 3 lb. Examples 37 and 39 show good combination of high SAFT and high peel adhesion to SS.

In other embodiments, the 180 degree peel adhesion of the adhesive compositions to polypropylene (PP) are greater than 0.1 lb, greater than 1.5 lb, or greater than 3 lb. Example 39 shows good combination of high SAFT and high peel adhesion to SS as well as high peel adhesion to PP. This peel adhesion to PP is much higher than that of the KRATON®-based formulation (Comparative Example P*) with a slightly different formulation.

In other embodiments, the loop tack of the adhesive compositions are greater than 0.5 lb, greater than 1 lb, or greater than 2 lb. Example 38 has a surprisingly high loop tack of 9.5 lb, greater than any other adhesive examples tested.

Hot Melt Adhesive

Table 14 shows the density, Brookfield viscosity, $M_w$, $M_n$, $M_w/M_n$ ratio, heat of fusion, $T_m$, $T_{m2}$, $T_c$, $T_{c2}$, tensile strength and % elongation at break of Examples 25-26, AFFINITY® GA 1950 and AFFINITY® GA 1900. The tests have been described earlier. Example 26 has a density, Brookfield viscosity, $M_w$, $M_n$, and $M_w/M_n$ ratio similar to those of AFFINITY® GA 1950. Similarly, Example 25 has a density, Brookfield viscosity, $M_w$, $M_n$, and $M_w/M_n$ ratio similar to those of AFFINITY® GA 1900. AFFINITY® GA 1950 and AFFINITY® GA 1900 are produced using a single site catalyst. Having similar values in density, Brookfield viscosity, $M_w$, $M_n$, or $M_w/M_n$ ratio, Examples 25-26 show much higher melting temperatures (110° C.) than the corresponding comparative examples, i.e., AFFINITY® GA 1950 (72° C.) and AFFINITY® GA 1900 (67° C.).

Examples 25-26, AFFINITY® GA 1950 and AFFINITY® GA 1900 were formulated into hot melt adhesives by the addition of a tackifier and a wax according to the formulations listed in Table 15. The resultant adhesives (i.e., Examples 66-67 and Comparatives AF and AG) were tested for Brookfield viscosity, PAFT, SAFT, and fiber tear. The Brookfield viscosity, PAFT, SAFT have been described earlier. The percent fiber tear test is described below. The Brookfield viscosity, PAFT, SAFT, and fiber tear test results are listed in Table 15.

Percent Fiber Tear

The percent fiber tear test was conducted with a corrugated board stock according to a standard industry test. The adhesive sample to be tested was heated to 177° C./350° F. and was applied on the board stock cut into 1×3 inch (25×76 mm) rectangular sheets with the corrugated flutes running lengthwise. The adhesive sample was applied, running lengthwise, as about a 5 mm (i.e., 0.2 inch) wide strip and could be drawn down with a spatula or hot melt applicator. Next a second strip was applied within 2 seconds and held, with moderate pressure, for 5 seconds to laminate. Laminated samples were conditioned for at least 24 hours at temperatures (i.e., 0, 35, 77 and 140° F.) selected for testing. For each selected temperature, a laminated sheet was held near one corner and using a spatula, one corner of one of the laminated sheets was folded back to form a hand hold. With the laminate held as near as possible to the source of heating or cooling in order to maintain the conditioning temperature, the folded corner was manually pulled as rapidly as possible at roughly a 45 to 90 degree angle relative to each sheet's lengthwise axis to tear the adhesive bond. The percent of torn fiber was estimated (fiber tear or FT) in 25% increments: i.e., 0%, 25%, 50%, 75% and 100%. Unless otherwise stated, the FT test was repeated on five replicate samples and the average of these five runs was reported.

In some embodiments, the PAFT of the hot melt adhesive compositions is greater than 130° F., greater than 140° F., or greater than 150° F. In other embodiments, the SAFT of the hot melt adhesive compositions is greater 180° F., greater than 190° F., or greater than 200° F.

In some embodiments, the rating of the Fiber Tear of the hot melt adhesive compositions is 100% at 77° F.-140° F. In other embodiments, the rating of the Fiber Tear of the hot melt adhesive compositions is 50% or greater at 35° F. and 100% at 35° F.-140° F. In further embodiments, the rating of the Fiber Tear of the hot melt adhesive compositions is 50% or greater at 0° F. and 100% at 35° F.-140° F.

Example 66 shows good high temperature PAFT and SAFT, as well as fiber tear over a wide temperature range. Therefore, Example 66 may perform well over a wide temperature range.

TABLE 14

The Properties of Examples 25-26, AFFINITY ® GA 1950 and AFFINITY ® GA 1900.

| Sample | Density ($g/cm^3$) | Brookfield Viscosity @ 177° C. (cP) | $M_w$ (g/mol) | $M_n$ (g/mol) | $M_w/M_n$ | Heat of Fusion (J/g) | $T_m$ (° C.) | $T_{m2}$ (° C.) | $T_c$ (° C.) | $T_{c2}$ (° C.) | Tensile Strength (MPa) | Elongation at Break (%) |
|---|---|---|---|---|---|---|---|---|---|---|---|---|
| Ex. 26 | 0.8771 | 15,757 | 22,400 | 9,720 | 2.3 | 60 | 110 | 96 | 95 | 20.3 | 2.1 | 190 |
| AFFINITY ® GA 1950[1] | 0.8755 | 15,237 | 22,500 | 10,100 | 2.2 | 64 | 72 | NA | 53 | 33 | 2.3 | 262 |
| Ex. 25 | 0.8707 | 7,168 | 19,800 | 8,810 | 2.2 | 14 | 110 | 92 | 95 | 10.4 | 1.2 | 72 |
| AFFINITY ® GA 1900[2] | 0.8714 | 7.873 | 19,500 | 9,020 | 2.2 | 57 | 67 | NA | 50 | 30 | 1.7 | 137 |

NM: Not Measured
NA: Not Applicable
[1]AFFINITY ® GA 1950 is a polyolefin plastomer obtained from The Dow Chemical Co., Midland, MI.
[2]AFFINITY ® GA 1900 is a polyolefin plastomer obtained from The Dow Chemical Co., Midland, MI.

TABLE 15

The Formulations and Properties of Hot Melt Adhesives from Examples 25-26, AFFINITY ® GA 1950 and AFFINITY ® GA 1900.

| Hot Melt Adhesive Example[5] | Polymer | Polymer wt % | Tackifier[3] ( ) wt % | Wax[4] (Paraflint H1) wt % | Brookfield Viscosity 177° C. (cP) | PAFT (° F.) | PAFT (° C.) | SAFT (° F.) | SAFT (° C.) | FT 0° F. | FT 35° F. | FT 77° F. | FT 140° F. |
|---|---|---|---|---|---|---|---|---|---|---|---|---|---|
| Ex. 66 | Ex. 26 | 34.5 | 35 | 30 | 15,757 | 165 | 74 | 211 | 99 | 50 | 100 | 100 | 100 |
| Comp. AF | AFFINITY ® GA 1950[1] | 34.5 | 35 | 30 | 15,237 | 160 | 71 | 201 | 94 | 0 | 50 | 100 | 100 |
| Ex. 67 | Ex. 25 | 29.5 | 35 | 35 | 7,168 | 149 | 65 | 195 | 91 | 0 | 0 | 100 | 100 |
| Comp. AG | AFFINITY ® GA 1900[2] | 29.5 | 35 | 35 | 7.873 | 156 | 69 | 204 | 96 | 0 | 0 | 100 | 100 |

[1]AFFINITY ® GA 1950 is a polyolefin plastomer obtained from The Dow Chemical Co., Midland, MI.
[2]AFFINITY ® GA 1900 is a polyolefin plastomer obtained from The Dow Chemical Co., Midland, MI.
[3]The tackifier was EASTOTAC ® H142R obtained from Eastman Company, Kingsport, Tennessee.
[4]The wax was PARAFLINT ® H1, a synthetic wax having a softening point of 104° C.
[5]All the samples contained 0.5 wt % IRGANOX ® I1010, a hindered phenolic antioxidant from Ciba Specialty Chemicals, Tarrytown, NY.

EXAMPLES 68-75

Hot Melt Adhesives

Interpolymers of Examples 22, 27-31, 31a and 31b were used in preparation of hot melt adhesives and their potential for use in pressure sensitive adhesives (PSA) and graphic arts was evaluated.

First 25/50/25 (polymer/tackifier/oil) blends were prepared with each of the eight polymers. The tackifier used was a Hydrogenated DCPD tackifier with a 100° C. softening point from Eastman Chemical (i.e., EASTOTAC® H-100R). The oil used was a white mineral oil from Sonneborn (i.e., Kaydol oil). These formulations and results for this series of formulations can be found in Table 16.

The formulated products (Examples 68-75) were made in each case by melting everything but the polymer together in a one point can in a forced air oven set at 177° C. Once this part of each formulation was molten the containers were transferred to a Glas-Col heating mantle set at 177° C. and stirred with a Caframo mixer. The polymer was then added slowly and mixed until completely smooth.

Coated Sample Preparation

All adhesive samples were coated as hot melts by hand onto 2 mil Mylar film using a P.G. & T. CO. #1 applicator which was preheated to the adhesive application temperature of 350° F. Just prior to drawing down the adhesives onto the Mylar film, the coating edge of the applicator was heated briefly over a Bunsen burner to help facilitate obtaining as smooth and streak free coating as possible. The adhesive coat weight for all samples was approximately 25 gsm (gram per square meter).

Tensile and Elongation Sample Preparation

Each product was melted at 120° C. Using a glass rod shimmed to 20 mils, a film of each material was made by pouring a puddle of adhesive onto silicone release paper and drawing the glass rod over the adhesive. After cooling the films were removed from the silicone release liner and in some cases talced to reduce surface tack. A Carver press and an ASTM D-638-4 die were used to cut dog bones for tensile and elongation testing.

Bleed Testing @ 120° F.

Coated samples of each formulation were laminated to 20 lb, 88 brightness copy paper and placed in an incubator set at 120° F. for two weeks. At the end of two weeks the back side of the paper was visually inspected for oil staining and assigned a number between 1 and 5 with 1 being no evidence of staining and 5 being complete staining of the paper stock. Formulation and properties for adhesive Examples 68-75 are summarized in Table 16.

Resistance to Plasticizer Migration at 120° F.

Coated samples of each formulation were laminated to 25 mil embossed vinyl fabric and conditioned at 120 F for a period of one week. At the end of one week, the laminates were removed from the incubator and allowed to cool back to room temperature. The coated films were then peeled off the vinyl fabric and visually inspected for evidence of contamination of the adhesive due to migration of plasticizer. Contamination usually results in softening of the adhesive and in severe cases the total loss of cohesive strength. The adhesives were assigned a number between 1 and 5 with 1 being no evidence of migration of the plasticizer into the adhesive and 5 being severe migration resulting in total loss of cohesive strength.

TABLE 16

Formulation and Properties for Adhesive Examples 68-75

| Ingredients | Example 68 | Example 69 | Example 70 | Example 71 | Example 72 | Example 73 | Example 74 | Example 75 |
|---|---|---|---|---|---|---|---|---|
| Polymer Ex. 27 | 25% | | | | | | | |
| Polymer Ex. 28 | | 25% | | | | | | |
| Polymer Ex. 29 | | | 25% | | | | | |
| Polymer Ex. 30 | | | | 25% | | | | |
| Polymer Ex. 31 | | | | | 25% | | | |
| Polymer Ex. 22 | | | | | | 25% | | |
| Polymer Ex. 31a | | | | | | | 25% | |
| Polymer Ex. 31b | | | | | | | | 25% |
| Kaydol oil | 25% | 25% | 25% | 25% | 25% | 25% | 25% | 25% |
| EASTOTAC ® H-100R | 50% | 50% | 50% | 50% | 50% | 50% | 50% | 50% |
| IRGANOX ® 1010 | 0.5% | 0.5% | 0.5% | 0.5% | 0.5% | 0.5% | 0.5% | 0.5% |
| Tests | | | | | | | | |
| Viscosity @ 350 F. (cps) | NA | 97500 | 86000 | 18400 | 17500 | 8450 | 6880 | 3100 |
| SAFT$^1$ (F.) | 155 | 139 | 105 | 159 | 131 | 127 | 130 | 125 |
| SAFT$^2$ (F.) | | | | 160 | 134 | 129 | 127 | 125 |
| Loop Tack$^1$ (pli) | 1.9 | 0.5 | 1.3 | 3.3 | 0.3 | 0.4 | 0.4 | 1.6 |
| Loop Tack$^2$ (pli) | | | | 4.1 | 0.7 | 1.3 | 1.2 | 4 |
| 180 degree peel to SS$^1$ (pli) | 4.1 | 2.7 | 0.4 | 6.0 | 4.2 | 4.1 | 3.8 | 6.2 |
| Aged peel to SS*$^{,1}$ (pli) | 5.08 | 0.44 | 0.6 | 6.05 | 0.92 | 2.9 | 0.57 | 5.9 |
| 180 degree peel to SS$^2$ (pli) | | | | 1.9 | 0.3 | 0.4 | 2.6 | 4.1 |
| 180 degree peel to PE$^2$ (¼" thick PE) | | | | 1.3 | 0.3 | 0.1 | 0.2 | 0.3 |
| 180 degree peel to PP$^2$ (¼" thick rigid PP) | | | | 2.8 | 1.7 | 1.9 | 0.7 | 2.7 |
| Bleed testing @ 120 F. for one week | 1 | 4 | 5 | 1 | 4 | 4 | 3 | 3 |
| 3 days on Vinyl at 120 F. | 2 | | | 3 | | | | |

*Measured after aging films at 120 F. for two weeks and equilibrating back to room temperature before testing.
$^1$When coated as hot melt by hand.
$^2$When machine coated using an Acumeter bench top slot die coater.

EXAMPLES 76-80

Hot Melt Adhesives

Based on the results of the polymer screening formulations (Examples 68-75), polymer of Example 30 was chosen for further adhesive formulations of Examples 76-78 designed to study the effect of
i) increasing the melt point of the tackifier and
ii) a tackifier with the same melt point that is produced from a slightly different feed stream.

Various tackifiers were tried in the formulations to see if there was any difference in compatibility. The tackifiers chosen were a blend of EASTOTAC® H-130 and H-100 to produce a 115 softening point and ESCOREZ™ 5415 for the higher softening point tackifiers. ESCOREZ™ 5400 was used as slightly different feed stream tackifier. The results of these formulations compared to a high performance, high heat resistance SBC based PSA (HL-2081 and HL-2053 from H. B. Fuller Company, St. Paul, Minn.) are provided in Table 17.

Polymer Example 31b was selected for testing in two standard Graphic Arts formulations (one with a blend of rosin ester and hydrogenated DCPD resin and the other with all DCPD resin). An Industry Standard adhesive used for comparative purposes (HM-948) and results can also be found in Table 17.

TABLE 17

Formulations and properties for adhesive examples 76-80.

| | Example 76 | Example 77 | Example 78 | Example 79 | Example 80 | HM-948 | HL-2081 | HL-2053 |
|---|---|---|---|---|---|---|---|---|
| Polymer Example 31 | 25% | 25% | 25% | | | | | |
| Polymer Example 31b | | | | 40% | 40% | | | |
| Kaydol | 25% | 25% | 25% | | | | | |
| EASTOTAC ® H-100R | 25% | | | 35% | | | | |
| EASTOTAC ® H-130R | 25% | | | | | | | |
| ESCOREZ ® 5400 | | 50% | | | | | | |
| ESCOREZ ® 5415 | | | 50% | | | | | |
| 155 paraffin | | | | 25% | 25% | | | |
| SYLVALITE ® RE-100L | | | | | 35% | | | |
| IRGANOX ® 1010 | 0.5% | 0.5% | 0.5% | 0.5% | 0.5% | | | |
| Brookfield Viscosity @ 350 F. (cps) | 20190 | 19760 | 23000 | 10670 | 10460 | 6625 | 13750 | 3160 |
| SAFT[1] (F.) | 171 | 162 | 175 | | | | | 152 |
| SAFT[2] (F.) | 167 | 155 | 169 | | | | 200 | 149 |
| Loop Tack[1] (pli) | 4.2 | 6.4 | 6.7 | | | | | 6.3 |
| Loop Tack[2] (pli) | 3.2 | 4 | 4.4 | | | | 3.2 | 6.3 |
| 180 degree peel to stainless steel[1] (pli) | 6.4 | 5.1 | 5.2 | | | | 6.9 | 6.5 |
| Aged peel to stainless[1] (pli) | 5.9 | 5 | 5.7 | | | | | |
| Loop Tack[2] (pli) | 3.2 | 4 | 4.4 | | | | | 6.3 |
| 180 degree peel to stainless steel[1] (pli) | 6.4 | 5.1 | 5.2 | | | | | 6.5 |
| 180 degree peel to stainless steel[2] (pli) | 1.4 | 1.8 | 2.7 | | | | 6.9 | 3.7 |
| 180 degree peel to PE[2] (pli) | 1.2 | 1.2 | 1.4 | | | | | 2.3 |
| 180 degree peel to PP[2] (pli) | 2 | 2.1 | 2.6 | | | | | 3.0 |
| Cold Crack @ 0 degrees F. | | | | Pass | Pass | Fail | | |
| PAFT Kraft/Kraft (F.) | | | | 115 | 130 | 138 | | |
| SAFT Kraft/Kraft (F.) | | | | 210 | 211 | 154 | | |
| Peak Stress (psi) ASTM D638-4 | | | | 350 | 568 | 605 | | |
| Elongation @ break (%) ASTM D638-4 | | | | 529 | 152 | >1000 | | |
| Bleed testing at one week 120 F. | 1 | 2 | 2 | | | | | 3 |
| 3 days on vinyl at 120 F. | 2 | 2 | 1.5 | | | | | 5 |

[1]When coated as hot melt by hand.
[2]When machine coated using an Acumeter bench top slot die coater.

As demonstrated above, in certain embodiments, increasing the melt point of the tackifier has a positive effect on loop tack and on SAFT. In certain embodiments, ESCOREZ™ 5400 and 5415 give slightly higher loop tack and SAFT as compared to their EASTOTAC® counterparts. In certain embodiments, polymers with less hard segments (blockiness) bleed less, have higher SAFT's and age better than polymers with medium to high levels of blockiness. The formulations show good aged properties. The adhesive formulations based on polymer Example 30 have properties close to and in certain embodiments, superior to HL-2081 which is considered to be a high performance, high heat resistance SIS based PSA.

The two graphic arts products based on polymer of Example 31b are comparable to the industry standard HM-948. In certain embodiments, the graphic art formulations provided herein have superior low temperature flexibility. In certain embodiments, the low temperature flexibility is useful in making freezer grade adhesives. In certain embodiments, these polymers find utility where plasticizer resistance is required (like bonding vinyl substrates).

Elastic Attachment Test Procedure

For the examples in Table 18, 2000 gram batches of each adhesive were prepared in a high shear sigma blade mixer set at 325° F. The adhesives were then transferred to a melter set at 325° F. and applied with a Nordson spiral spray system onto three strands of Lycra thread (Decitex 940 type 151) using the method described in U.S. Pat. No. 4,842,666. After equilibrating to room temperature the laminations were then stretched to 95% of full extension and fastened to a rigid piece of cardboard. The ends of the elastic were then cut through the polyethylene film and the test board placed in an incubator set at 100° F. After a period of four hours the test board was removed and the percent creep calculated using the formula: Initial length minus final length divided by initial length times 100. This method is described more fully in U.S. Pat. No. 6,531,544. In Table 18, Comparative Example AF and HL-8128 (from H. B. Fuller Company, St. Paul, Minn.) are used to compare to the construction adhesive Examples 81-83 and HL-1486 (from H. B. Fuller Company, St. Paul, Minn.) is used to compare to the elastic attachment Examples 84 and 85.

Pressure sensitive adhesives based on Polymer Examples 27 and 30 are more resistant to bleeding at 120° F. for one week than the standard SBC based adhesive HL-2053. Examples 76-78 were less affected by plasticizer migration when placed in contact with 25 mil vinyl fabric for three days at 120° F. than the standard SBC based adhesive HL-2053. Examples 76-78 maintained good adhesion to the vinyl and only suffered slight loss of cohesive strength. The HL-2053 SBC based adhesive lost all of its cohesive strength and became extremely gummy after only one day in this test.

Construction Adhesive Bond Preparation

Substrates and Equipment

Clopay DH-203 1.0 mil embossed polyethylene
BBA Style 717D (16.9 gsm) spunbond nonwoven
Acumeter model 3900 10 PG melter
Nordson model CWEO5-M2RCXE Spray System
Nordson single module 0.018 spiral spray nozzle
May Coating CLS-300 coater laminator A 2000 gm sample of each adhesive formulation was prepared in a sigma blade high shear mixer set at 325° F. The products were then transferred to an Acumeter Model 3900 10 PG melter for spiral spray application between polyethylene film and nonwoven fabric. All of the adhesives were applied onto the polyethylene backsheet and then laminated using 30 psi nip pressure to the nonwoven fabric. The web speed was adjusted based on the adhesive through put to obtain a coat weight of 6.2 gsm at approximately 500 ft/minute. The air flow and nozzle height was adjusted for each adhesive until the best possible 20 mm wide spiral pattern was obtained. The spiral patterns were then rated on a 1-10 scale with 10 being a perfectly concentric pattern with good edge control and 1 being a very poor spiral pattern that appears to look more like melt blown than spiral. A SIS based industry standard adhesives (HL-8128) along with Comparative AF based are included with the inventive samples.

Spiral Spray Bond Testing

The poly/nonwoven laminations were peeled apart using an I-Mass slip peel tester set at a peel rate if 12 inches/minute and the average force recorded over a 20 second time period. For each product 6 constructs were peeled and the average of the 6 averages recorded along with the standard deviation. Initial peel means peeled at room temperature after equilibrating at room temperature for 24 hours. Aged peel means aging the bonds at room temperature for 24 hours then 50° C. for two weeks and then equilibrating at room temperature for 24 hours and then peeling. The 37° C. peel means conditioning the bonds for 24 hours at RT and then placing the constructs in a chamber set at 37° C. for one hour and peeling them at 37° C.

TABLE 18

Formulations and properties for adhesive examples 81-85.

| | Example 81 | Example 82 | Example 83 | Comp. AF | HL-8128 | Example 84 | Example 85 | HL-1486 |
|---|---|---|---|---|---|---|---|---|
| Polymer Example 30 | | 20 | 5 | | | 20 | | |
| Polymer Example 31b | 20 | | | | | | 25 | |
| Affinity GA-1900 | | | 55 | 60 | | | | |
| Kaydol oil | 20 | 25 | | | | 25 | 15 | |
| EASTOTAC ® H-100R | 60 | 55 | | | | 55 | 60 | |
| EASTOTAC ® H-130R | | | 40 | | | | | |
| ESCOREZ ® 5637 | | | | 40 | | | | |
| IRGANOX ® 1010 | 0.5 | 0.5 | 0.5 | 0.5 | | 0.5 | 0.5 | |
| Brookfield Viscosity at | | | | | | | | |
| 300° F. (cP) | 4850 | 20000 | 15000 | 7125 | 3050 | 20000 | 12200 | 5725 |
| 325° F. (cP) | | 12200 | 9820 | 5100 | 1575 | 12200 | 7210 | 2850 |
| 350° F. (cP) | | | 6700 | 3125 | 1050 | | | 1840 |
| Coat Weight (gsm) | 6.2 | 6.2 | 6.2 | 6.2 | 6.2 | 30 | 30 | 30 |

TABLE 18-continued

Formulations and properties for adhesive examples 81-85.

| | Example 81 | Example 82 | Example 83 | Comp. AF | HL-8128 | Example 84 | Example 85 | HL-1486 |
|---|---|---|---|---|---|---|---|---|
| Pattern Width (mm) | 20 | 20 | 20 | 20 | 20 | 6.4 | 6.4 | 6.4 |
| Target adhesive flow (gms/min) | 18 | 18 | 18 | 18.9 | 18 | 30 | 30 | 30 |
| Actual adhesive flow (gms/min) | 18.8 | 20.4 | 18.8 | 18.3 | 19.4 | 22 | 25.2 | 25 |
| Web speed (ft/min) | 522 | 567 | 522 | 485 | 513 | 366 | 420 | 417 |
| Nip Pressure (psi) | 30 | 30 | 30 | 30 | 30 | 30 | 30 | 30 |
| Temperature (C.) | 150 | 165 | 165 | 150 | 150 | 150 | 165 | 165 |
| Air Pressure (psi) | 6 | 21 | 10 | 13 | 17 | 6 | 8 | 6 |
| Nozzle Height (mm) | 50 | 50 | 50 | 35 | 25 | 25 | 25 | 25 |
| Pump (RPM) | 2.4 | 2.4 | 2.4 | 2.2 | 2.3 | 3.2 | 3.4 | 3.4 |
| Pump pressure (psi) | 194 | 185 | 397 | 388 | 108 | 228 | 282 | 190 |
| Pattern Rating (1-10) | 10 | 7 | 8 | 9 | 9 | 9 | 8 | 9 |
| 1 | 189 | 281 | 265 | 187 | 240 | | | |
| 2 | 165 | 191 | 280 | 199 | 205 | | | |
| 3 | 183 | 185 | 196 | 189 | 199 | | | |
| 4 | 213 | 183 | 238 | 230 | 252 | | | |
| 5 | 200 | 170 | 279 | 206 | 297 | | | |
| 6 | 193 | 153 | 409 | 220 | 188 | | | |
| Average Initial Peel PE to Nonwoven (g) | 191 | 194 | 278 | 205 | 230 | | | |
| 1 | | | | | | 100 | 59 | 24 |
| 2 | | | | | | 100 | 48 | 21 |
| 3 | | | | | | 90 | 60 | 24 |
| 4 | | | | | | 88 | 49 | 18 |
| 5 | | | | | | 100 | 52 | 21 |
| 6 | | | | | | 87 | 49 | 20 |
| Average % Creep | | | | | | 94 | 53 | 21 |
| 1 | 120 | 132 | 139 | 92 | 155 | | | |
| 2 | 122 | 155 | 402 | 176 | 130 | | | |
| 3 | 137 | 157 | 161 | 177 | 186 | | | |
| 4 | 130 | 149 | 153 | 168 | 135 | | | |
| 5 | 154 | 161 | 569 | 159 | 178 | | | |
| 6 | 128 | 165 | 457 | 134 | 190 | | | |
| Average Peel @ 100 F. PE to Nonwoven (g) | 132 | 153 | 314 | 151 | 162 | | | |

Figure 10:
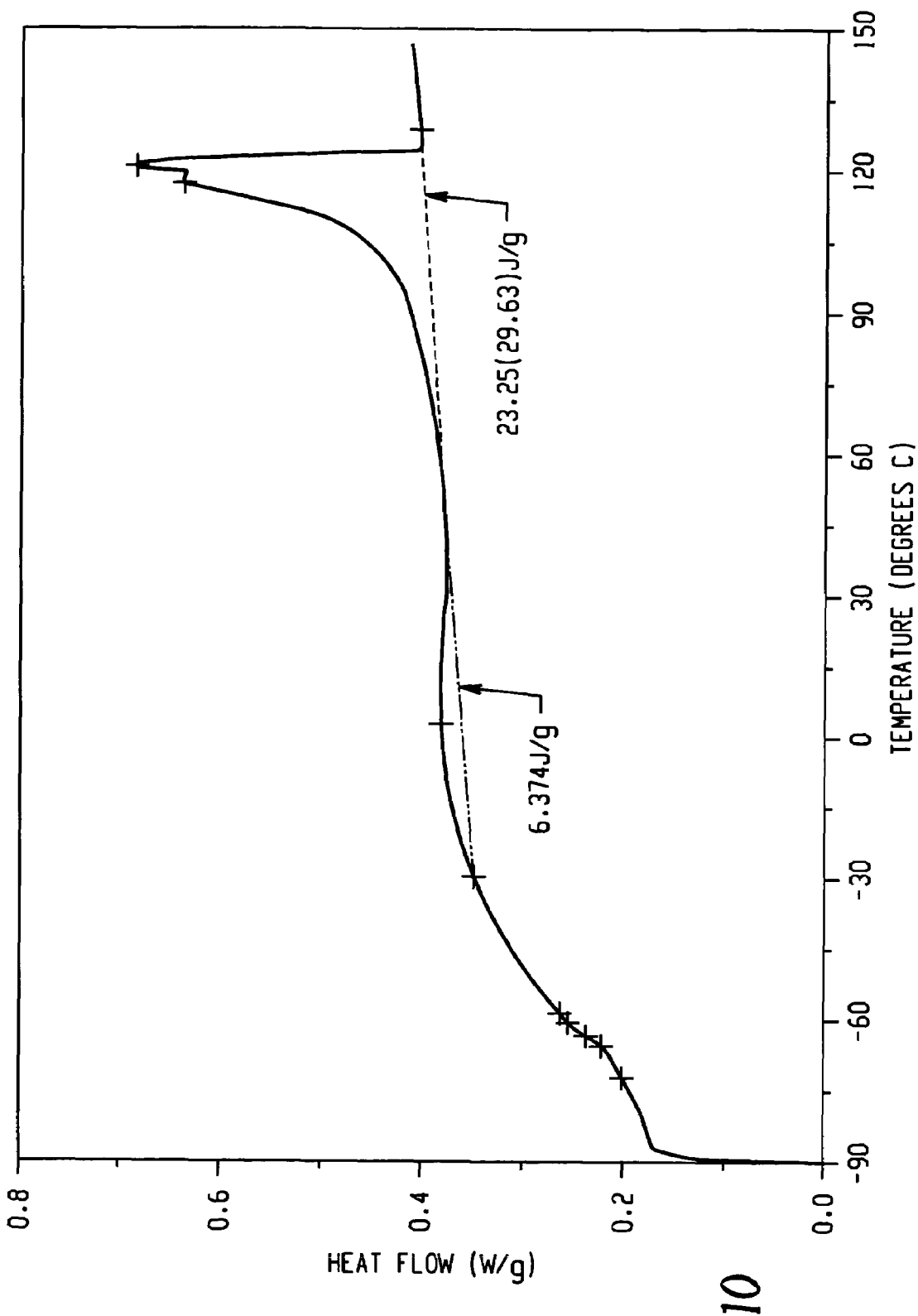
FIG. 10 shows a DSC second heating curve for Polymer Example 30.

As demonstrated above, Examples 81-83 all exhibited good viscosity, sprayability, pattern rating (10 being the highest) and good average and aged peels at 100° F. as compared to Comparative Example AF and HL-8128, indicating that these materials would be good construction adhesives. Example 83 also showed unexpected and favorable behavior in that the peel increased with aging at 100° F. indicating that it may be more advantageous for use at both room temperature and higher temperatures such as 100° F. FIG. 10 is a DSC curve showing the melting behavior of Polymer Example 30.

TABLE 19

Formulations and properties for adhesive examples 86-87.

| | Example 86 | Example 87 |
|---|---|---|
| Polymer Example 31c | 25 | |
| Polymer Example 31d | | 25 |
| Kaydol oil | 25 | 25 |
| EASTOTAC ® H-100R | 50 | 50 |
| EASTOTAC ® H-130R | | |
| IRGANOX ® 1010 | 0.5 | 0.5 |
| Brookfield Viscosity @ 300 F. (cps) | 16900 | 15800 |
| @ 325 F. (cps) | 10500 | 9400 |
| @ 350 F. (cps) | 7310 | 6880 |
| Loop Tack[1] (Pli) | 2.3 | 2.1 |
| 180 degree peel to SS[1] (Pli) | 2.2 | 4.1 |
| 180 degree peel to PE[1] (Pli) | 0.9 | 1.9 |
| 180 degree peel to PP[1] (Pli) | 2 | 0.2 |
| SAFT[1] (F) | 147 | 156 |

[1] When machine coated using an Acumeter bench top slot die coater.

When machine coated using an Acumeter bench top die coater.

Figure 11:
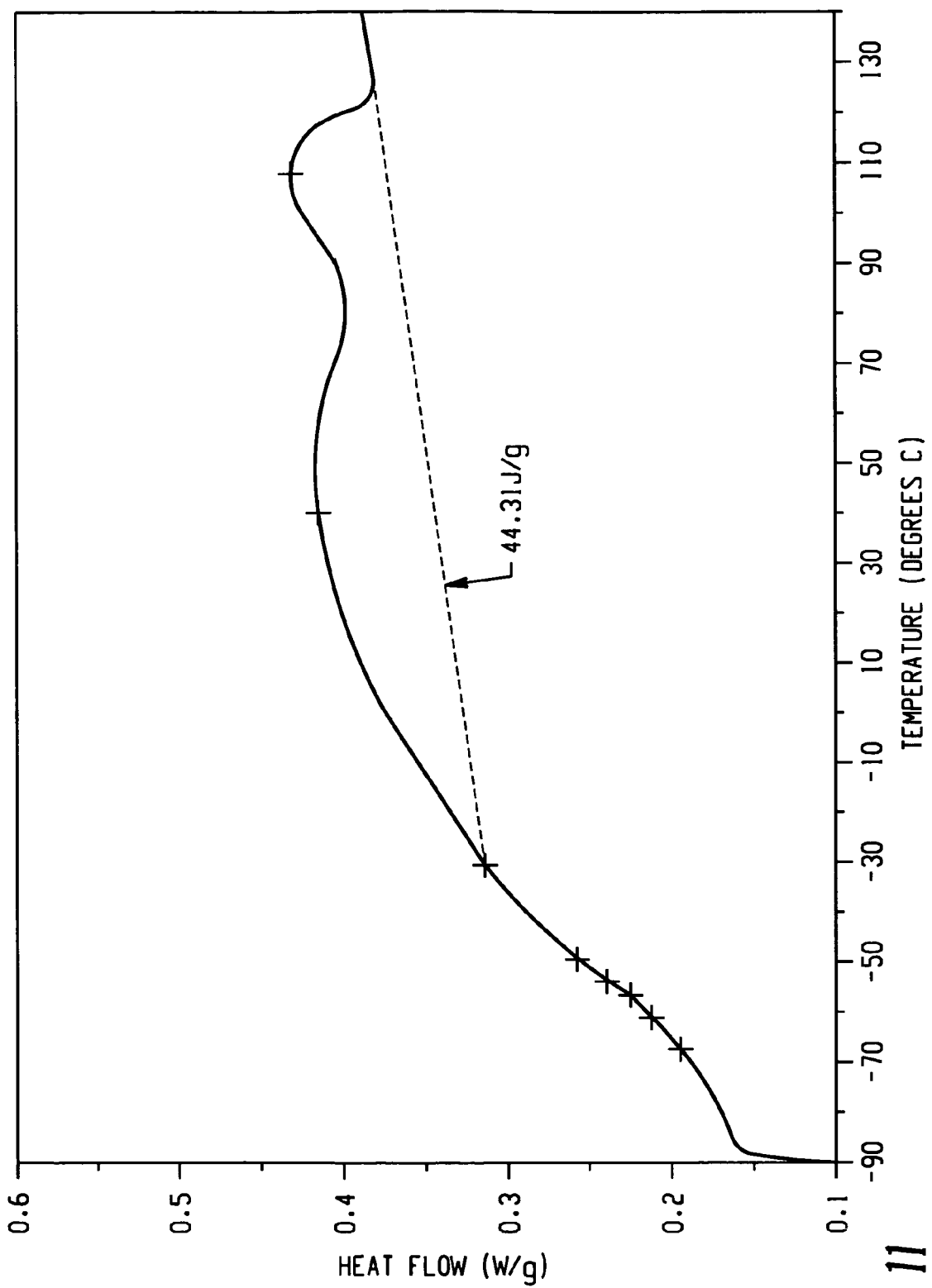
FIG. 11 shows a DSC second heating curve for Polymer Example 31c.
Figure 12:
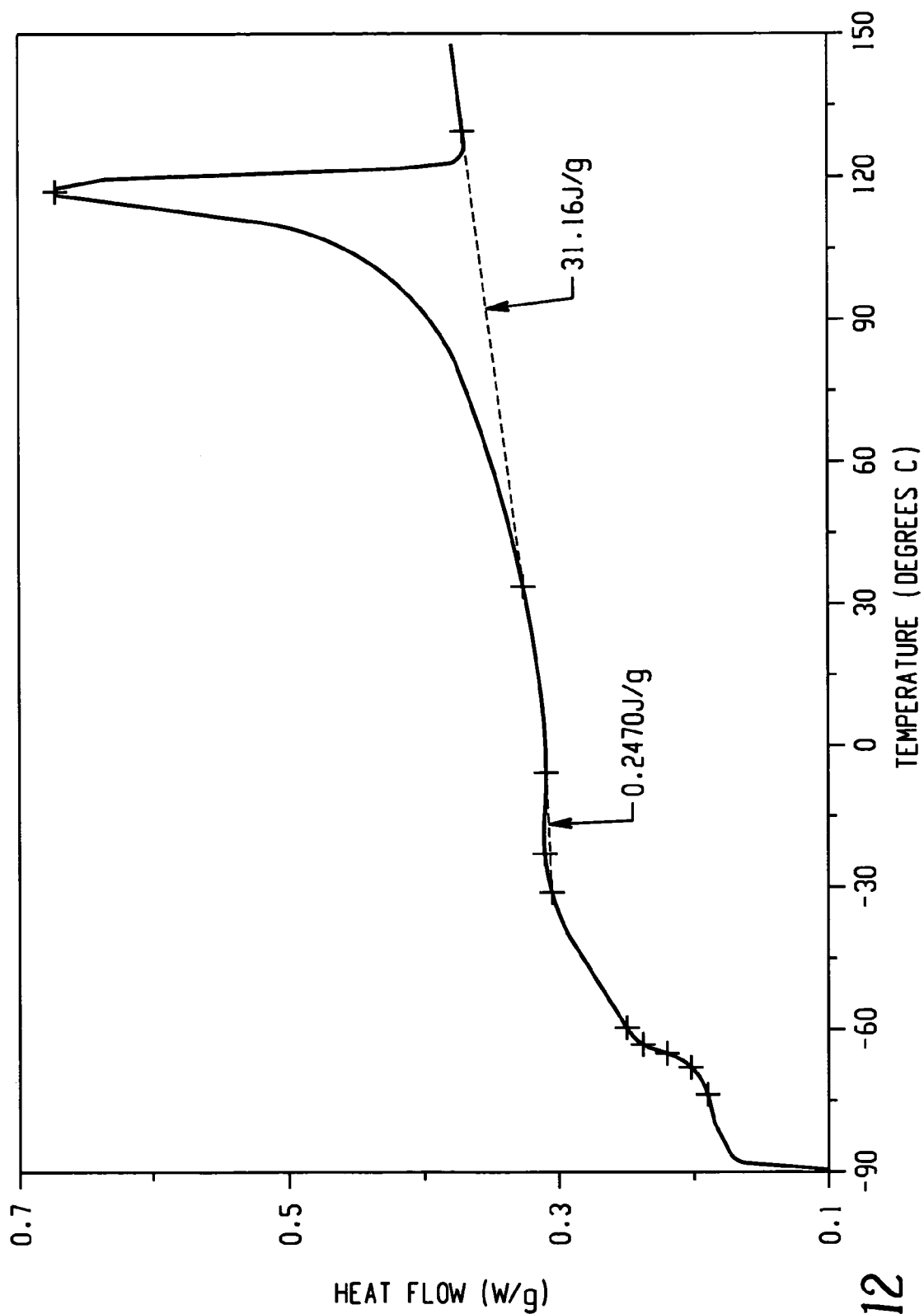
FIG. 12 shows a DSC second heating curve for Polymer Example 31d.

Table 19 shows that the adhesive properties using two polymers with the same overall density but with different melting behavior as shown in FIGS. 11 and 12; with Polymer Example 31c having a broad melting curve with peaks at 108° C. and 40° C. and Polymer Example 31d having sharper melting behavior with a melting point at 117° C. Both samples, when formulated, showed good viscosity, indicating the ability to be applied at the application temperature of 300° F.-350° F. and good loop tack, peel to various substrates and SAFT.

As demonstrated above, embodiments of the invention provide adhesive compositions which can be used as a hot melt adhesives or pressure sensitive adhesives. Some adhesives may have relatively high SAFT temperatures; other adhesives may have relatively high peel adhesion; still other adhesives may have relatively good temperature resistance. Consequently, the adhesives can be used to make labels, tapes, diapers, decals, cases, cartons, or trays, medical devices, bandages, hygiene products, etc. They can also be used for book binding. In certain embodiments, the pressure sensitive adhesives are freezer grade pressure sensitive adhesives.

While the invention has been described with respect to a limited number of embodiments, the specific features of one embodiment should not be attributed to other embodiments of the invention. No single embodiment is representative of all aspects of the invention. In some embodiments, the compositions or methods may include numerous compounds or steps not mentioned herein. In other embodiments, the compositions or methods do not include, or are substantially free of, any compounds or steps not enumerated herein. Variations and modifications from the described embodiments exist. Finally, any number disclosed herein should be construed to mean approximate, regardless of whether the word "about" or "approximately" is used in describing the number. The appended claims intend to cover all those modifications and variations as falling within the scope of the invention.

What is claimed is:

1. A composition comprising:
   (i) at least one ethylene/α-olefin interpolymer, wherein the ethylene/α-olefin interpolymer:
      (a) has a $M_w/M_n$ from about 1.7 to about 3.5, at least one melting point, $T_m$, in degrees Celsius, and a density, d, in grams/cubic centimeter, wherein the numerical values of $T_m$ and d correspond to the relationship:

$$T_m > -2002.9 + 4538.5(d) - 2422.2(d)^2, \text{ or}$$

(b) has a $M_w/M_n$ from about 1.7 to about 3.5, and is characterized by a heat of fusion, ΔH in J/g, and a delta quantity, ΔT, in degrees Celsius, defined as the temperature difference between the tallest DSC peak and the tallest CRYSTAF peak, wherein the numerical values of ΔT and ΔH have the following relationships:

$$\Delta T > -0.1299(\Delta H) + 62.81 \text{ for } \Delta H \text{ greater than zero and up to 130 J/g,}$$

$$\Delta T \geq 48° \text{ C. for } \Delta H \text{ greater than 130 J/g,}$$

wherein the CRYSTAF peak is determined using at least 5 percent of the cumulative polymer, and if less than 5 percent of the polymer has an identifiable CRYSTAF peak, then the CRYSTAF temperature is 30° C.; or (c) is characterized by an elastic recovery, Re, in percent at 300 percent strain and 1 cycle measured with a compression-molded film of the ethylene/α-olefin interpolymer, and has a density, d, in grams/cubic centimeter, wherein the numerical values of Re and d satisfy the following relationship when ethylene/α-olefin interpolymer is substantially free of a cross-linked phase:

$$Re > 1481 - 1629(d); \text{ or}$$

(d) has a molecular fraction which elutes between 40° C. and 130° C. when fractionated using TREF, characterized in that the fraction has a molar comonomer content of at least 5 percent higher than that of a comparable random ethylene interpolymer fraction eluting between the same temperatures, wherein said comparable random ethylene interpolymer has the same comonomer(s) and has a melt index, density, and molar comonomer content (based on the whole polymer) within 10 percent of that of the ethylene/α-olefin interpolymer; or (e) has a storage modulus at 25° C., G'(25° C.), and a storage modulus at 100° C., G'(100° C.), wherein the ratio of G'(25° C.) to G'(100° C.) is in the range of about 1:1 to about 9:1; and
   (ii) at least one tackifier.

2. The composition of claim 1, wherein the ethylene/α-olefin interpolymer has a $M_w/M_n$ from about 1.7 to about 3.5, at least one melting point, $T_m$, in degrees Celsius, and a density, d, in grams/cubic centimeter, wherein the numerical values of $T_m$ and d correspond to the relationship:

$$T_m \geq 858.91 - 1825.3(d) + 1112.8(d)^2.$$

3. The composition of claim 1, wherein the ethylene/α-olefin interpolymer has a $M_w/M_n$ from about 1.7 to about 3.5 and is characterized by a heat of fusion, ΔH in J/g, and a delta quantity, ΔT, in degrees Celsius defined as the temperature difference between the tallest DSC peak and the tallest CRYSTAF peak, wherein the numerical values of ΔT and ΔH have the following relationships:

$$\Delta T > -0.1299(\Delta H) + 62.81 \text{ for } \Delta H \text{ greater than zero and up to 130 J/g,}$$

$$\Delta T \geq 48° \text{ C. for } \Delta H \text{ greater than 130 J/g,}$$

wherein the CRYSTAF peak is determined using at least 5 percent of the cumulative polymer, and if less than 5 percent of the polymer has an identifiable CRYSTAF peak, then the CRYSTAF temperature is 30° C.

4. The composition of claim 1, wherein the ethylene/α-olefin interpolymer is characterized by an elastic recovery, Re, in percent at 300 percent strain and 1 cycle measured with a compression-molded film of the ethylene/α-olefin interpolymer, and has a density, d, in grams/cubic centimeter, wherein the numerical values of Re and d satisfy the following relationship when ethylene/α-olefin interpolymer is substantially free of a cross-linked phase:

$$Re > 1481 - 1629(d).$$

5. The composition of claim 4, wherein the numerical values of Re and d satisfy the following relationship:

$$Re > 1491 - 1629(d).$$

6. The composition of claim 4, wherein the numerical values of Re and d satisfy the following relationship:

$$Re > 1501 - 1629(d).$$

7. The composition of claim 4, wherein the numerical values of Re and d satisfy the following relationship:

$$Re > 1511 - 1629(d).$$

8. The composition of claim 1, wherein the ethylene/α-olefin interpolymer has a molecular fraction which elutes between 40° C. and 130° C. when fractionated using TREF, characterized in that the fraction has a molar comonomer content of at least 5 percent higher than that of a comparable random ethylene interpolymer fraction eluting between the same temperatures, wherein said comparable random ethylene interpolymer has the same comonomer(s) and has a melt index, density, and molar comonomer content (based on the whole polymer) within 10 percent of that of the ethylene/α-olefin interpolymer.

9. The composition of claim 1, wherein the ethylene/α-olefin interpolymer has a storage modulus at 25° C., G'(25° C.), and a storage modulus at 100° C., G'(100° C.), wherein the ratio of G'(25° C.) to G'(100° C.) is in the range of about 1:1 to about 9:1.

10. The composition of claim 1, wherein the composition is a hot melt adhesive composition, or a thermoplastic marking composition.

11. The composition of claim 1, wherein the α-olefin is styrene, propylene, 1-butene, 1-hexene, 1-octene, 4-methyl-1-pentene, norbornene, 1-decene, 1,5-hexadiene, or a combination thereof.

12. The composition of claim 1, wherein the tackifier is present in the range from about 5% to about 70% by weight of the total composition.

13. The composition of claim 1, wherein the tackifier has a R&B softening point equal to or greater than 80° C.

14. The composition of claim 1, further comprising an additive selected from the group consisting of plasticizers, oils, waxes, antioxidants, UV stabilizers, colorants or pigments, fillers, flow aids, coupling agents, crosslinking agents, surfactants, solvents, and combinations thereof.

15. The composition of claim 1, wherein the composition has a shear adhesion failure temperature (SAFT) of at least 32° C.

16. The composition of claim 1, wherein the composition has a 180° peel adhesion to a polyester substrate of at least about 100 N/dm.

17. The composition of claim 1, wherein the composition is a hot melt adhesive and the G'(25° C.) of the hot melt adhesive composition is from about $1\times10^3$ to about $1\times10^6$ Pa.

18. The composition of claim 17, wherein the ratio of G'(25° C.) to G'(75° C.) of the hot melt adhesive composition is from about 1:1 to about 110:1.

19. The composition of claim 1, wherein the ethylene/α-olefin interpolymer has a density of about 0.85 to about 0.88 g/cc.

20. The composition of claim 1, wherein the ethylene/α-olefin interpolymer has a density of about 0.86 to about 0.875 g/cc.

21. The composition of claim 1, wherein the ethylene/α-olefin interpolymer has a melt index of about 5 to about 50 g/10 minutes.

22. The composition of claim 1, wherein the ethylene/α-olefin interpolymer has a melt index of about 10 to about 30 g/10 minutes.

23. The composition of claim 1, wherein the ethylene/α-olefin interpolymer is present in a range from about 10% to abut 50% by weight of the total composition.

24. The composition of claim 14, wherein the additive is a plasticizer which is a mineral oil, liquid polybutene, or a combination thereof.

25. A composition comprising:
(i) at least one ethylene/α-olefin interpolymer, wherein the ethylene/α-olefin interpolymer has:
(a) a molecular fraction which elutes between 40° C. and 130° C. when fractionated using TREF, characterized in that the fraction has a block index of at least 0.5 and up to about 1; or
(b) an average block index greater than zero and up to about 1.0 and a molecular weight distribution, Mw/Mn, greater than about 1.3; and
(ii) at least one tackifier.

26. The composition of claim 25, wherein the ethylene/α-olefin interpolymer has a molecular fraction which elutes between 40° C. and 130° C. when fractionated using TREF, characterized in that the fraction has a block index of at least 0.5 and up to about 1.

27. The composition of claim 25, wherein the ethylene/α-olefin interpolymer has an average block index greater than zero and up to about 1.0 and a molecular weight distribution, Mw/Mn, greater than about 1.3.

28. The composition of claim 25, wherein the composition is a hot melt adhesive composition, or a thermoplastic marking composition.

29. The composition of claim 25, wherein the α-olefin is styrene, propylene, 1-butene, 1-hexene, 1-octene, 4-methyl-1-pentene, norbornene, 1-decene, 1,5-hexadiene, or a combination thereof.

30. The composition of claim 25, wherein the tackifier is present in the range from about 5% to about 70% by weight of the total composition.

31. The composition of claim 25, wherein the tackifier has a R&B softening point equal to or greater than 80° C.

32. The composition of claim 25, further comprising an additive selected from the group consisting of plasticizers, oils, waxes, antioxidants, UV stabilizers, colorants or pigments, fillers, flow aids, coupling agents, crosslinking agents, surfactants, solvents, and combinations thereof.

33. The composition of claim 25, wherein the composition has a shear adhesion failure temperature (SAFT) of at least 32° C.

34. The composition of claim 25, wherein the composition has a 180° peel adhesion to a polyester substrate of at least about 100 N/dm.

35. The composition of claim 25, wherein the composition is a hot melt adhesive and the G'(25° C.) of the hot melt adhesive composition is from about $1\times10^3$ to about $1\times10^6$ Pa.

36. The composition of claim 35, wherein the ratio of G'(25° C.) to G'(75° C.) of the hot melt adhesive composition is from about 1:1 to about 110:1.

37. The composition of claim 33, wherein the composition is a hot melt adhesive and the SAFT of the hot melt adhesive composition is greater than 82° C.

38. The composition of claim 25, wherein the ethylene/α-olefin interpolymer has a density of about 0.85 to about 0.88 g/cc.

39. The composition of claim 25, wherein the ethylene/α-olefin interpolymer has a density of about 0.86 to about 0.875 g/cc.

40. The composition of claim 25, wherein the ethylene/α-olefin interpolymer has a melt index of about 5 to about 50 g/10 minutes.

41. The composition of claim 25, wherein the ethylene/α-olefin interpolymer has a melt index of about 10 to about 30 g/10 minutes.

42. The composition of claim 25, wherein the ethylene/α-olefin interpolymer is present in a range from about 10% to abut 50% by weight of the total composition.

43. The composition of claim 32, wherein the additive is a plasticizer which is a mineral oil, liquid polybutene, or a combination thereof.

44. An article comprising a substrate coated with the composition of claim 10.

45. The article of claim 44, wherein the article is a medical device, a bandage, or a hygiene article.

46. An article comprising a substrate coated with the composition of claim 28.

47. The article of claim 46, wherein the article is a medical device, a bandage, or a hygiene article.

* * * * *